United States Patent
Snyder et al.

(10) Patent No.: US 9,384,327 B2
(45) Date of Patent: Jul. 5, 2016

(54) SEMANTIC INTEROPERABILITY SYSTEM FOR MEDICINAL INFORMATION

(75) Inventors: Tim Snyder, Basel (CH); Alan Peter Honey, Walnut Creek, CA (US)

(73) Assignee: Clinerion Ltd., Basel (CH)

( * ) Notice: Subject to any disclaimer, the term of this patent is extended or adjusted under 35 U.S.C. 154(b) by 565 days.

(21) Appl. No.: 13/395,946

(22) PCT Filed: Sep. 13, 2010

(86) PCT No.: PCT/US2010/048625
§ 371 (c)(1),
(2), (4) Date: Oct. 2, 2012

(87) PCT Pub. No.: WO2011/032086
PCT Pub. Date: Mar. 17, 2011

(65) Prior Publication Data
US 2013/0030827 A1    Jan. 31, 2013

Related U.S. Application Data

(60) Provisional application No. 61/242,252, filed on Sep. 14, 2009.

(51) Int. Cl.
*G06N 5/00* (2006.01)
*G06F 19/00* (2011.01)

(52) U.S. Cl.
CPC .......... *G06F 19/345* (2013.01); *G06F 19/324* (2013.01); *G06N 5/00* (2013.01)

(58) Field of Classification Search
CPC .................................................. G06F 17/2527
USPC ........................................................ 706/62
See application file for complete search history.

(56) References Cited

U.S. PATENT DOCUMENTS

2006/0206883 A1* 9/2006 Sabbouh .................. 717/146
2009/0259459 A1* 10/2009 Ceusters et al. ............ 704/9

FOREIGN PATENT DOCUMENTS

WO    WO 03/030025    4/2003

OTHER PUBLICATIONS

A. El Fadly et al., "Electronic Healthcare Record and Clinical Research in Cardiovascular Radiology", AMIA 2007 Symp. Proc. pp. 216-220.*

(Continued)

*Primary Examiner* — Kakali Chaki
*Assistant Examiner* — Vincent Gonzales
(74) *Attorney, Agent, or Firm* — King & Spalding LLP

(57) ABSTRACT

A system for managing and exchanging electronic information provides a rules management component for executing conceptual rules, an ontology management component, an information model management component, and a system configuration management component. The ontology management component manages at least one ontology and mappings between members of different ontologies. The ontologies may include a code system and a terminology. The ontology management component may manage a value set that is a subset of the terminology. The information model management component manages one or more information model schemas, each defining an information model and comprising information defining at least one slot within the information model. The system configuration management component manages configuration information on the configuration of each system component. The system configuration component utilizes services of the rules management component, information model management component and ontology management component to dynamically bind value sets to slots of the information model.

25 Claims, 41 Drawing Sheets

(56) References Cited

OTHER PUBLICATIONS

S. Nimmagadda et al., "Ontology Based Data Warehouse Modeling and Managing Ecology of Human Body for Disease and Drug Prescription Management" 2d IEEE Int'l Conf. on Digital Ecosystems and Technologies, 2008, pp. 212-220.*

M. O'Connor et al., "Supporting Rule System Interoperability on the Semantic Web with SWRL", The Semantic Web—ISWC 2005, pp. 974-986.*

V. Kashyap, "From the Bench to the Bedside: The Role of Semantic Web and Translational Medicine for Enabling the Next Generation Healthcare Enterprise", Proc. Int'l Joint Conf. on Biomedical Engeineering Sys. and Tech., Jan. 28-31, 2008, pp. 35-56.*

Choi, N. et al. "A survey on ontology mapping", ACM Sigmod Record 35.3, 2006, pp. 34-41.*

International Search Report from PCT/US2010/048625, issued Mar. 22, 2011.

Kohler et al. "Using XML Technology for the Ontology-based Semantic Integration of Life Science Databases," IEEE Transactions on Information Technology, vol. 8, No. 2, Jun. 1, 2014, p. 154-160.

Communication (Office Action) issued for corresponding European Patent Application No. 10755285.3, Jan. 5, 2016.

* cited by examiner

SEMANTIC INTEROPERABILITY SYSTEM FOR MEDICINAL INFORMATION

CROSS REFERENCE TO RELATED APPLICATIONS

This application is a United States national phase filing under 35 U.S.C. §371 of International Application No. PCT/US2010/048625, filed Sep. 13, 2010, which claims priority to U.S. Provisional Patent Application No. 61/242,252, filed Sep. 14, 2009, the entire contents of each of which is hereby fully incorporated herein by reference.

The present application relates to a system for managing and exchanging electronic information, and in particular to a system providing semantic interoperability between similar or related medicinal terminology concepts.

BACKGROUND OF THE INVENTION

A plurality of terms and expressions has been established within the domain of healthcare and medicinal terminologies. For example, there are many different names for one and the same disease. While someone prefers the Latin expression for a disease, someone else may use the English expression for the same disease. Although these two persons would understand each other, a computer system needs to know that those expressions define the same disease. The same problem occurs in the field of medicinal products, such as drugs, apparatuses or instruments. For this and other reasons, standardizations of healthcare and medicinal terminologies have been established. For instance, the Systematized Nomenclature of Medicine (SNOMED) was designed as a comprehensive nomenclature of clinical medicine. This nomenclature has the function of accurately storing and retrieving records of clinical care. It provides a common language enabling a consistent manner of communicating and storing healthcare and medicinal terms.

A further standard which has been developed is the so called Health Level Seven (HL7), which provides a framework for the exchange, integration, sharing and retrieval of electronic health information. The HL7 standard allows different computer systems to communicate and exchange healthcare or medicinal information on a standardized platform. A particular conceptual standard of HL7 is the Reference Information Model (RIM) that expresses the data content needed in a specific clinical or administrative context. RIM also provides an explicit representation of the semantic and lexical connections that exist between the information carried in the fields of HL7 messages.

Although standardization of terminologies has been established in recent years, a plethora of terms is in use, where some of the terms have an identical meaning. In addition, different countries may have different standards. Thus, the plurality of different concepts and terminologies used in the healthcare and medicinal domain requires a system that accounts for these difficulties. Thus, there is a need for an application providing semantic interoperability between different standards.

Further to the above, huge volumes of healthcare information are locked in islands divided by disparate technologies, disparate representations, such as format or syntax, disparate semantics and levels of semantic richness. On the other hand, there is a need for the effective exchange of healthcare information. For example Electronic Health Record data needs to be exchanged to support effective treatment of mobile patients that see multiple providers, such as when suffering chronic co-morbidities, such as diabetes or heart disease. A further aspect is the order management of laboratories, radiology etc. and the referral processing that would profit from an effective exchange of healthcare information.

Moreover, current healthcare information systems do not provide for analytic aggregation, such as for disease registries, for treatment efficiency, signal detection, clinical protocol improvement and real-time feedback into evidence based medicine. A further aspect is the regulatory reporting, which suffers from the disadvantages of current systems.

For instance, a great deal of medical processes and information are currently still paper based. However, even when healthcare information is captured in an electronic form, it is often textual or at best in a very basic syntactic format or the same information is represented in many different ways. The work to extract information and transform in a meaningful way to make it useful for disease management, drug efficiency analysis, signal detection and real-time clinical decision making is huge.

As mentioned above, technology and syntactic interoperability challenges have been solved using integration engines and horizontal and vertical integration standards. Such industry standards include common domain models, such as HL7 RIM and BRIDG, and clinical terminologies, such as SNOMED, and have provided some improvement to the understanding.

However, there are many competing and overlapping standards and standards organizations. The standards themselves are typically consensus-based cooperative efforts resulting in the least common denominator and often leave a great deal of room for interpretation. Moreover, the architectural and technical quality of standards is often driven and influenced by people and organizations with their own commercial agendas or carriers at heart. Thus, in some cases the standard itself becomes the goal rather than the real improvement in healthcare.

BRIEF SUMMARY OF THE INVENTION

The present invention overcomes these disadvantages by using semantically robust systems with rigorously defined terminologies coupled with ontological reasoning and inferencing, i.e. using semantic disambiguation.

As will be outlined in more detail below, the present invention relates to a system to achieve deterministic computable semantics and then deliver interoperability based on them. The information is captured and managed in a truly semantically rich and robust fashion in the first place.

In accordance with principles of the present invention, a system for managing and exchanging electronic information provides a plurality of system components. These components include a rules management component for executing conceptual rules, an ontology management component, an information model management component, and a system configuration management component. The ontology management component manages at least one ontology and mappings between members of different ontologies, where each of the ontologies include at least one code system and at least one terminology, and where the ontology management component may further manage at least one value set that is a subset of the at least one terminology. The information model management component manages one or more information model schemas. Each of these information model schemas defines an information model and comprises information defining at least one slot within the information model. The system configuration management component manages configuration information on the configuration of each system component. Further, the system configuration component utilizes services of the rules management component, information model management component and ontology management component to dynamically bind one or more value sets to one or more of the at least one slot of the information model.

In accordance with an embodiment of the invention, the system comprises a rules repository that is included in the rules management component. The rules repository stores the conceptual rules. The system also comprises an ontology repository, an information model repository and a metadata registry. The ontology repository is include in the ontology management component and that stores the at least one value set, the at least one ontology and the mappings between members of different ontologies. Further, the information model repository is included in the information model management component and stores the information models. The metadata registry is included in the system configuration management component and stores the configuration information.

In accordance with another embodiment of the present invention, the mappings between members of different ontologies stored in the ontology repository contain pointers to the members of different ontologies stored in the ontology repository.

According to an embodiment of the present invention the at least one slot within the information model stored in the information model repository includes a pointer pointing to at least one rule stored in the rules repository. This at least one rule includes one or more pointers to value sets stored in the ontology repository to accomplish the dynamically binding of the one or more value sets to the one or more of the at least one slot.

In accordance with another embodiment of the present invention, the system configuration management component comprises a service configured for managing registration and query of information from the metadata registry.

In accordance with another embodiment of the present invention, the system configuration management component comprises a service configured for querying the information models, where the querying includes execution of terminology binding operations utilizing services of the rules management component and the ontology management component.

According to a further embodiment, the system configuration management component comprises a service configured for querying configuration information from the metadata registry.

According to yet another embodiment, the rules management component may provide a concept resolution service that resolves differences and ambiguities between different representations of the same underlying concept both within and across terminologies that are stored in the ontology repository. The ontology management component may employ the concept resolution service.

In accordance with an embodiment of the present invention, the ontology management component comprises an ontology authoring component configured for authoring the at least one ontology and the at least one value set to be stored in the ontology repository.

In accordance with another embodiment of the present invention, the ontology management component comprises a service configured for querying the ontology repository.

According to a further embodiment, the information models stored in the information model management repository comprise data representing at least one of the group of the model of Health Level Seven, HL7, the Reference Information Model, RIM, the Biomedical Research Integrated Domain Group, BRIDG, model, the OpenEHR Reference Model and the ISO-21090 data types.

According to a further embodiment, the ontology management component is configured for managing a domain of terms representing at least one of the group of Systematized Nomenclature of Medicine, SNOMED, terminology, the Medical Dictionary for Regulatory Activities, MedDRA, terminology, and an organization specific terminology.

According to a further embodiment, a service employed by the ontology management component is a medicinal product management service creating and maintaining identification information identifying terminologies associated with a medicinal product.

In accordance with another embodiment of the present invention, the medicinal product management service may further map between medicinal product terms and particular terms stored as members of the at least one ontology.

According to a another embodiment of the present invention the system may further comprise a reasoning engine configured for reasoning across the at least one ontology to draw inferences.

In accordance with another aspect of the present invention, a system for managing and exchanging electronic information provides a rules management component, a terminology management component and an information model management component. The rules management component may execute conceptual rules, while the terminology management component maps between different terminologies. The information model management component binds to the terminology management component and the rules management component. It may further be configured for storing value sets including electronic information comprising particular terms. Each of the three above mentioned components employs a plurality of services collaborating with each other as consumers and providers of their respective functionality. The terminology management component further utilizes services of the information model management component to map between different terminologies of the stored information value sets.

In accordance with an embodiment of the present invention, the rules management component, terminology management component and information model management component include a rules repository, terminology repository and information model repository, respectively. As an example of the present invention, the terminology repository stores mapping value sets, which are pointers to the information value sets stored in the information model repository.

In accordance with another embodiment of the present invention, the mapping value sets stored in the terminology repository may include a tuple of pointers, one pointing to an information value of the information value sets stored in the information model repository and one pointing to an information value stored in the rules repository. Thus, mapping between the information model repository and the rules repository is accomplished.

According to a further embodiment, a concept resolution service may be employed by the rules management component to identify relationships between concepts and/or terminologies associated with at least one concept. Further, a conceptual rule may define at least one concept of terminologies representing a domain of terms. Such domain of terms may represent, for example, the above mentioned SNOMED terminology, the Medical Dictionary for Regulatory Activities, MedDRA, terminology or a terminology being specific to an organization.

A further aspect of the present invention employs a medicinal product management service which creates and maintains identification information identifying terminologies associated with a medicinal product. Further, the medicinal product management service may map between medicinal product terms and the particular terms stored as value sets in the information model management component.

In accordance with an embodiment of the present invention, data stored in the information model management component may represent the model of Clinical Data Interchange Standards Consortium (CDISC), the model of Health Level Seven (HL7), the Reference Information Model (RIM) of HL7, the Biomedical Research Integrated Domain Group (BRIDG) model, and/or the data types specified by ISO 21090.

In an embodiment of the present invention, the terminology management component may register for events of one or both of the other two components. Each event may be triggered by a service of the respective other component.

In a further aspect of the present invention, a rules repository provides for storage of conceptual rules. These conceptual rules may, for example, reflect differences in the ontologies, hierarchies and structure of terminologies according to a particular standard. Such standard terminologies may be SNOMED or MedDRA. Representing these rules correctly in the system prevents ambiguous use and coding of concepts using different terminologies.

According to an embodiment of the present invention, a terminology repository stores mapping value sets. For instance, such a mapping value set may include pointers to information value sets and/or pointers to the rules repository to accomplish a mapping between the information value sets and the rules repository.

In accordance with another embodiment of the present invention, an information model repository stores information value sets. For example, the information value sets comprise data sets according to the Clinical Data Interchange Standards Consortium (CDISC) or the Health Level Seven (HL7).

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which.

DETAILED DESCRIPTION OF THE INVENTION

The present invention provides a high level semantic interoperability system with a common model across all domains of interest. Such domains of interest may include the HL7 RIM, SNOMED or BRIDG standards. HL7 is a leading Standard development organization for the Lifescience Domain. The present invention offers a model bound to a robust data type specification, such as ISO data types, and a methodology for binding terms from concept-based terminologies. For instance, the ISO DT standard is semantically isomorphic to HL7 Abstract Data Types R2.

The existing healthcare and lifescience standards provide abstract concepts (e.g., HL7 RIM, BRIDG and IHE), structures for data exchange (e.g., HL7, IHE and X12), structures for organization (e.g., CCR, CDA and CCD). However, existing standards do not fully define content. Clinical data definitions, on the other had, define a specific instance of an object (e.g., Pulse), primary attribute, data types and constraints (e.g., Rate), and a terminology (e.g., SNOMED code or other code translation).

As mentioned above, current healthcare information systems provide the same information in many different ways, which makes the exchange of data and electronic information cumbersome, if not impossible. The present invention therefore provides a platform for computable semantics and interoperability (CSI) that will be able to meet the needs of many participants in the healthcare community, both consumer organizations, such as hospitals, payers, pharmaceuticals as well as other software development organizations supplying those consumers. As will be further outlined below, the CSI capabilities are based on a service-oriented architecture (SOA) approach and technology to deliver the platform.

Figure 1A:
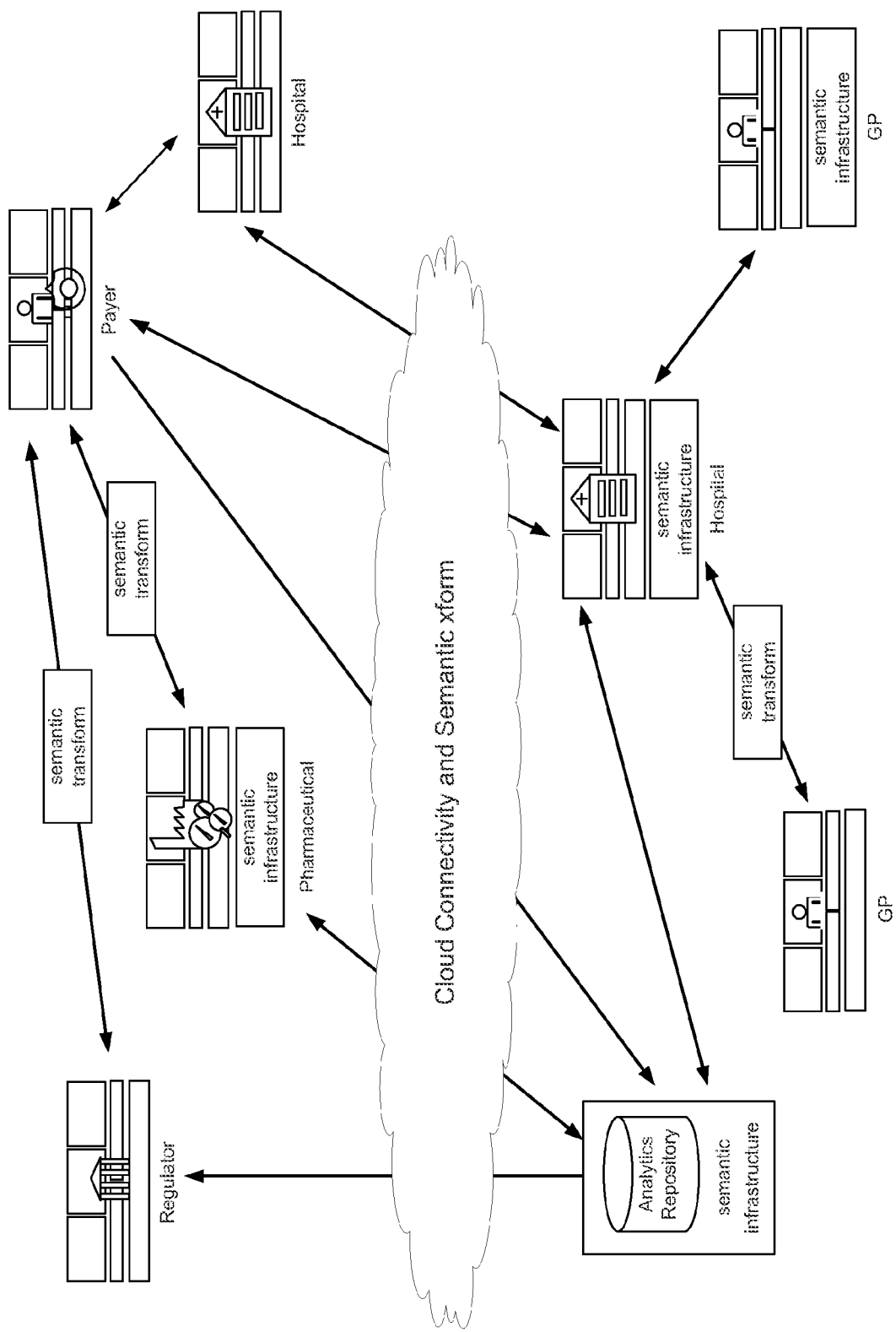
FIG. 1a depicts a high level positioning of software within a healthcare interoperability space.

Referring to FIG. 1a, a high level positioning of such a platform within the healthcare interoperability space is depicted. The consumer organizations would run one or more applications on the CSI platform. e.g. as shown for the pharmaceutical and hospital. In other cases, organizations running other software would interoperate with organizations using the platform of the present invention with transformations. Such transformations can be provided and performed by particular services of the CSI platform.

As will be appreciated by the person skilled in the art, the applications of consumer organizations will run on a computing device of the consumer organization, such as the pharmaceutical or hospital. The invention is however not restricted to a particular kind or number of computer systems. Indeed, the present invention comprises all combinations of numbers of computers and types of computers, such as desktop computers, server computers, laptops, notebooks, netbooks, handheld devices, e.g. PDA, MDA, smart-phones etc. The CSI platform may run on one or more server computer systems or other computer systems, which can be accessed by the computers of the consumer organizations. Such accessing may take place via a network, such as a local area network (LAN) or wide area network (WAN), such as the Internet. It has to be noted that the present invention is not restricted to a particular type of network, but may also include wireless networks.

Additionally, one or more analytics repositories are created using the platform to provide the ability to aggregate and analyze information from multiple different organizations. Such analytics repositories as well as the above discussed applications and services can communicate via a "cloud", which is a set of hosted infrastructure and connectivity services to enable organizations to exchange information in a secure, robust fashion, and make use of semantic transformations, which enable the transformation of a message from a format used by one organization into the format used by another in such a way that full meaning is retained an in some cases even enhanced.

Thus, the key feature of the platform is the ability to represent and store information that is semantically robust and that the rich semantics are computable and not just information for direct human consumption. As will be outlined in more detail further below, this is achieved by the use of a set of semantically aware services within a service oriented architecture (SOA) framework supported by ontological reasoning. A core set of services is provided to enable healthcare applications to manage and share information in an open and extendable manner. To improve data integration, interoperability and analysis, robust, static and dynamic semantics are provided based on an information model, a semantic infrastructure and well defined data types.

Figure 1B:
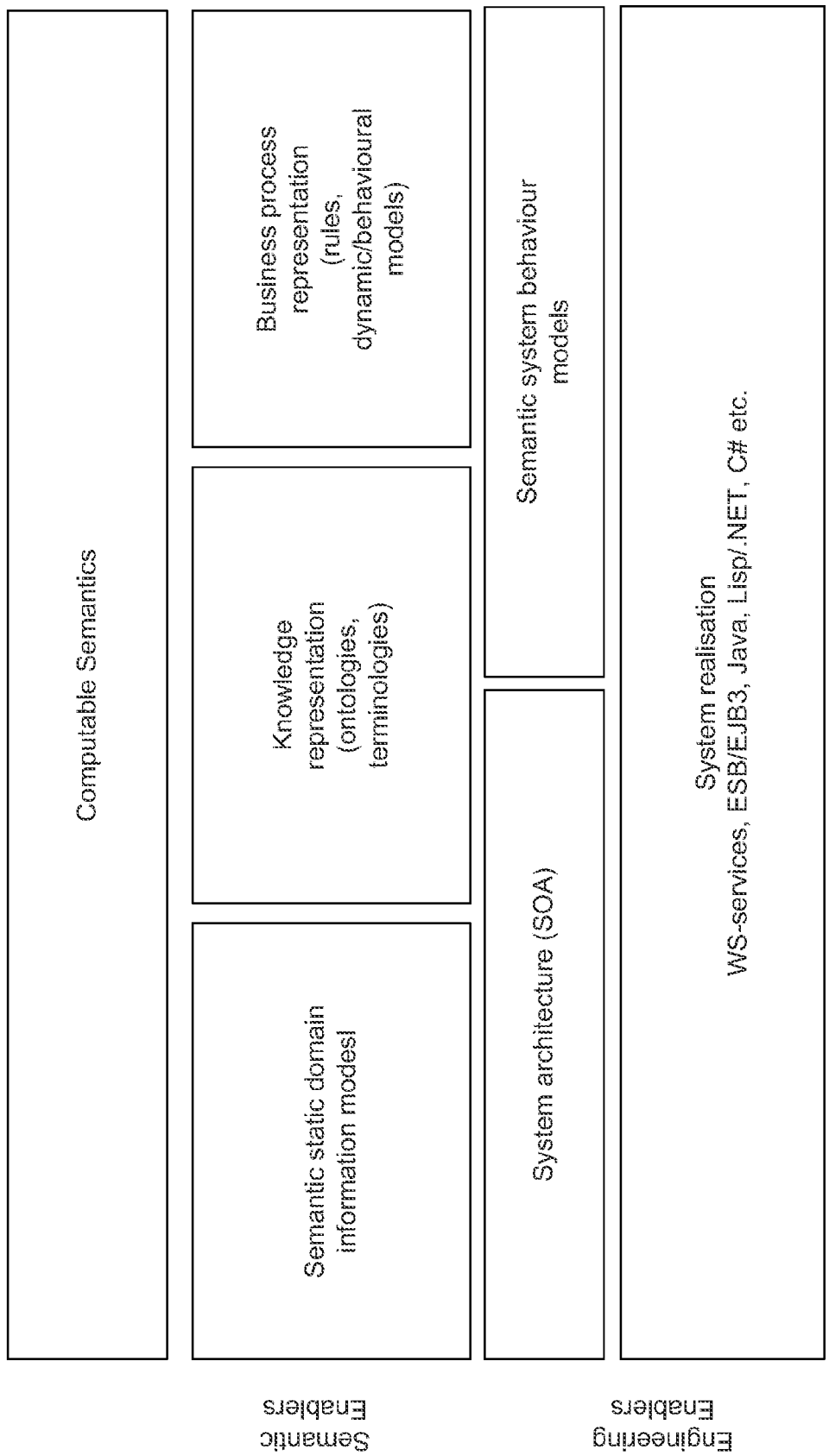
FIG. 1b illustrates components to realize computable semantics in accordance with an embodiment of the present invention.

A further general overview is provided by FIG. 1b depicting the main elements that are needed at a conceptual level. The provided set of services for computable semantics and interoperability include three semantic enablers. These are the static domain information models, e.g. HL7 RIM V3, knowledge representation, such as ontologies and terminologies, and dynamic models, such as business process and behavioral models.

For example, information models may comprise data representing the HL7 model (Health Level Seven model), the RIM (Reference Information Model), the BRIDG model (Biomedical Research Integrated Domain Group model), the OpenEHR Reference Model and/or the ISO-21090 data types.

Further, the semantic enablers require a flexible underlying platform consisting of a set of services within the service oriented architecture. The platform of the present invention provides both a coherent set of services to manage ontologies as well as a rule-based mechanism for binding between information models and those ontologies. The system of the present invention therefore allows domain models to be bound to a robust data type specification, e.g. ISO21090. Moreover, the information models can be bound to the knowledge representation models.

Figure 2A:
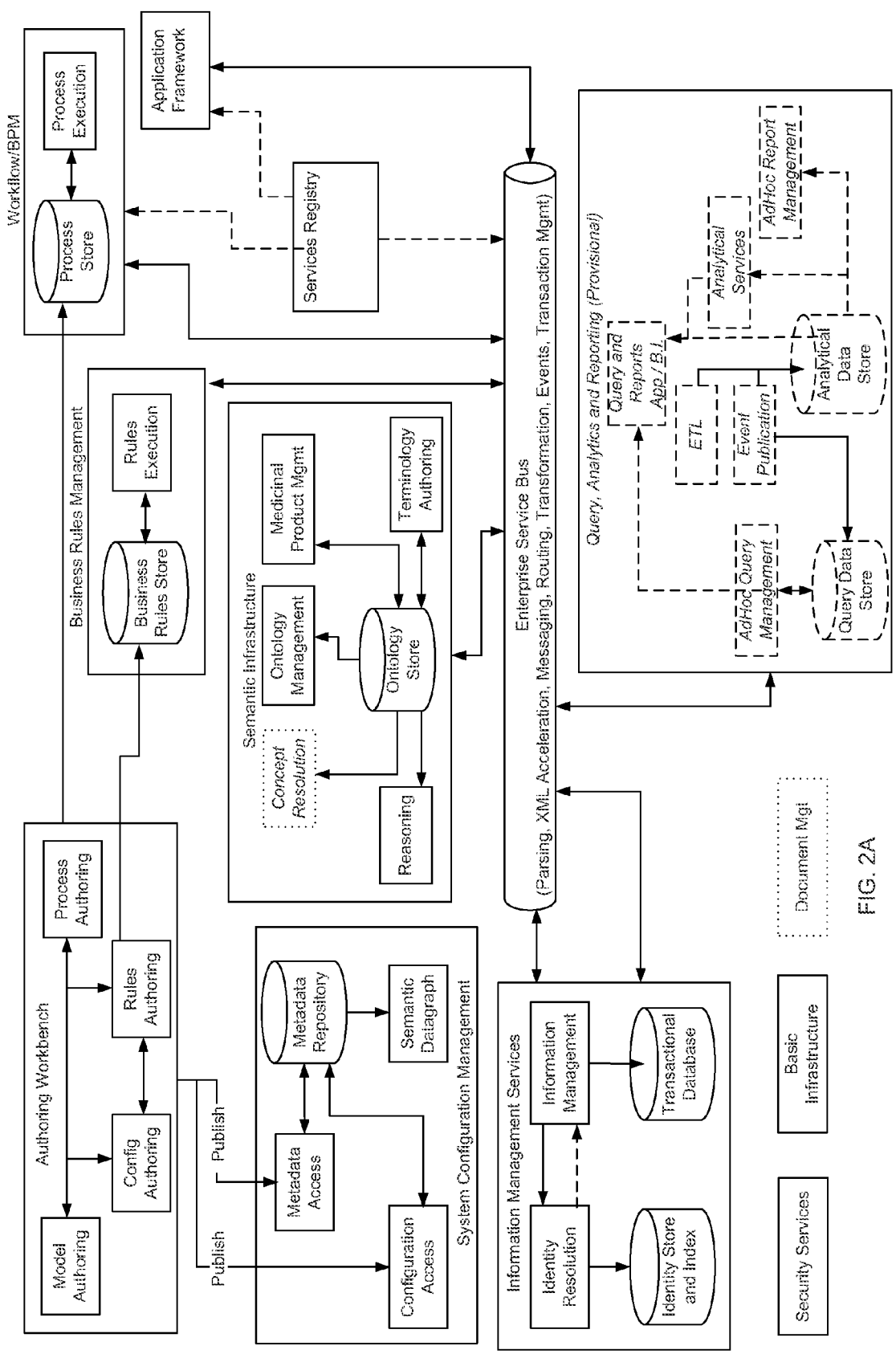
FIG. 2a depicts the logical sub-system components and their relationships of the computable semantics and interoperability (CSI) platform in accordance with an embodiment of the present invention.

Turning now to FIG. 2a, exemplary sub-systems and their respective services of the platform of the present invention are illustrated. The platform is a system for managing and exchanging electronic information suitable for healthcare and lifescience applications. The system includes a plurality of components, some of which are depicted in FIG. 2a. In an embodiment the platform includes a rules management component, an ontology management component, an information model management component and a system configuration management component. It has to be noted that the platform according to the present invention is not limit to these components. In a different aspect of the invention it may include only some of the depicted components. Further, a platform comprising more components then the ones depicted is also within the scope of the present invention.

The sub-systems, components and respective services of the platform can be implemented using an object-oriented approach. Thus, the components or sub-systems are built as an object or set of objects, which can be instantiated during runtime to provide the particular services defined by each sub-system or each component. A component may be seen as one or more programming objects, while the service is provided by this programming object during run-time using interfaces. As will be appreciated by the person skilled in the art, other programming approaches instead of an object-oriented approach can be used to implement the CSI-SOA platform and all of its sub-systems, components and services.

As indicated above, the primary goal of the CSI-SOA platform is to enable development of interoperable semantically robust applications across the full healthcare spectrum. Thus, the CSI-SOA platform has a plurality of components providing the following key capabilities. The sub-systems of the platform provide for dynamic authoring and management of terminologies, information models, terminology bindings of the information models, work flows, business rules and system configurations. These capabilities are provided for example by the authoring workbench, semantic infrastructure and system configuration management components depicted in FIG. 2a.

Further, capabilities for managing and reasoning across ontologies are provided with the semantic infrastructure component. This semantic infrastructure component will be described in more detail below.

A further aspect is a set of generic capabilities to support development of applications that provide integration with document management, workflow management, business rules execution and underlying semantic services. Thus, healthcare software providers as well as healthcare companies can use the CSI-enabled SOA platform in accordance with the present invention.

Returning to FIG. 2a, a workbench component is depicted, which comprises at least four applications for model authoring, configuration authoring, rules authoring and process authoring. For example, the rules and process authoring applications each provide an integrated set of tooling that creates and manages business rules and process definitions, which can be stored in a business rules store and process store within the corresponding sub-systems respectively. The model authoring application allows for the creation and management of information models, semantic data graphs, rule-based binding of information models to terminologies, while the configuration authoring allows for the creation and management of system configuration information. The results of such authoring processes can be published to a Meta data registry or Meta data repository that is part of the system configuration management component.

One of the core components of the platform is the semantic infrastructure component. This component includes a terminology authoring application to create and manage terminologies and more generally any ontologies. The authored ontologies and terminologies can be stored in the ontology store, also referred to as an ontology repository. Based on the stored information regarding terminologies and ontologies, the semantic infrastructure component provides for reasoning of ontologies and ontology management, as will be outlined further below.

A component falling within the semantic infrastructure is a concept resolution service that resolves differences and ambiguities between different representations of the same underlying concept both within and across terminologies.

The platform as illustrated in FIG. 2a further comprises a rules management component for executing conceptual rules.

Moreover, the platform includes an information management service component including information management, identity resolution services and corresponding data stores, as well as a component for querying analytics and reporting.

Figure 2B:
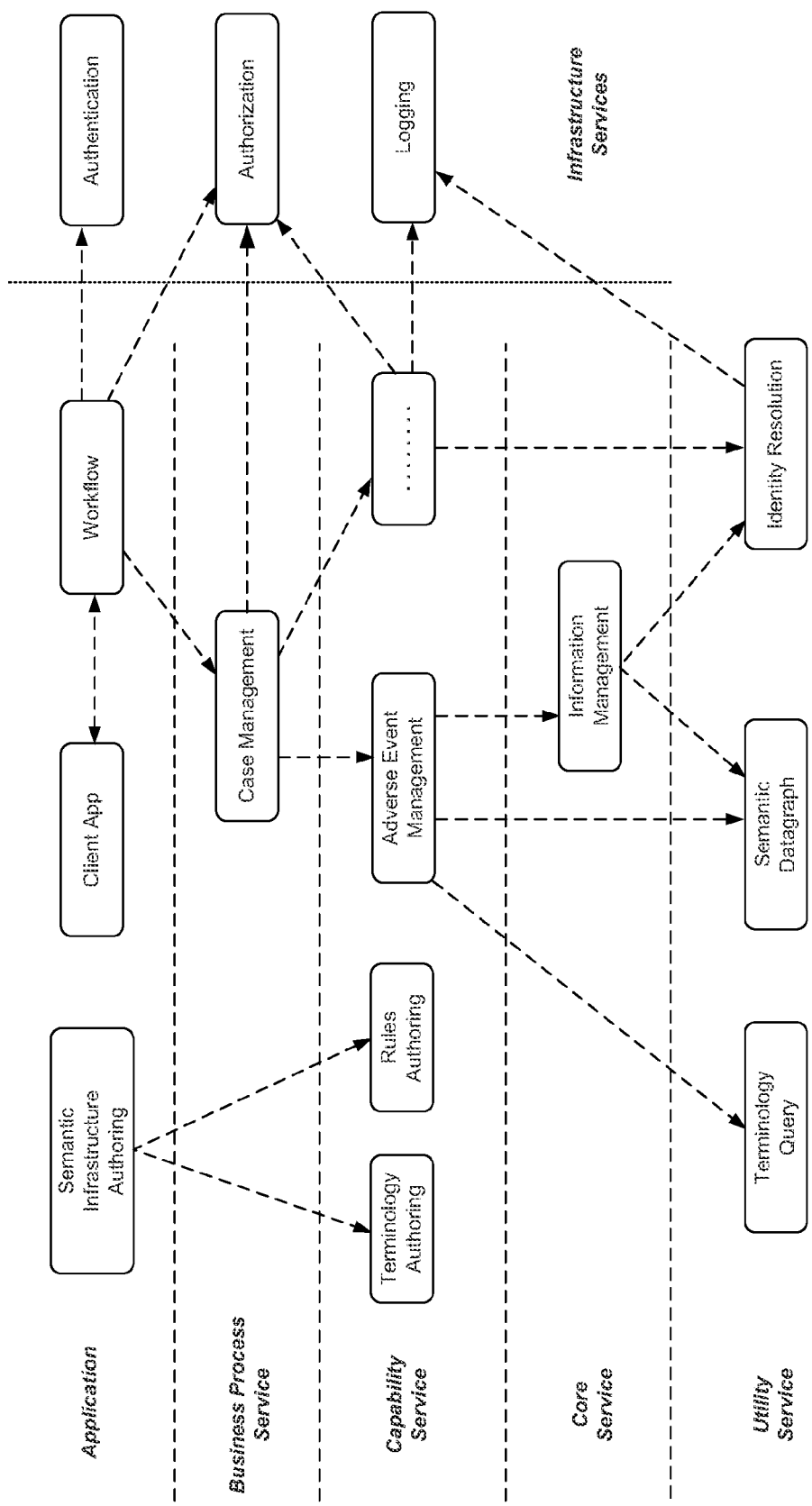
FIG. 2b illustrates the service framework and service inventory identified in various layers of the CSI platform in accordance with an embodiment of the present invention.

According to an embodiment of the present invention, FIG. 2b illustrates exemplary services of the platform as depicted in FIG. 2a in accordance with an overall service taxonomy.

As can be seen from FIG. 2b, particular layers of services are identified, i.e. an application layer, business process service layer, capability service layer, core service layer and utility service layer.

The application layer manages presentation concerns and manual workflow tasks. The business process service layer manages sequencing, flow of control and process state in managed processes, i.e. where there is a predefined flow and where the concept of a processed instance makes sense. The capability service layer has the main functional logic and behavior. Services in this layer are generally stable with respect to changes in the business process and reflect an equivalent collection of related functions at the business level. Exemplary services of the capability service layer are the terminology authoring and rules authoring services. Further, adverse event management service may also be part of the capability service layer.

The core (data) service layer provides controlled access to persistence functionality, i.e. repository or database access. This service layer isolates service consumers from details of the database itself.

Finally, the utility service layer is a special type of business capability service that provides a reusable set of functionality that is not specific to any particular business transaction, i.e. it does not use core data services. Exemplary services of the utility service layer are the terminology query service, semantic data graph service or identity resolution service.

Returning back to FIG. 2a, exemplary components of the platform will now be described in more detail.

The semantic infrastructure depicted in the middle of FIG. 2a provides the ability to manage and use information in the form of ontologies. It uses technologies commonly referred to as "semantic web" technologies, such as RDF (Resource Description Framework), RDFS (RDF Schema), OWL (Web Ontology Language) etc, to provide intelligent management of medical terminologies and other ontologies. It further provides the ability to "reason" across those ontologies to draw inferences, which uses pre-defined axioms and assertions in those ontologies to establish new facts without the need to define explicit rules.

According to an embodiment of the present invention, the semantic infrastructure provides for authoring of terminologies and ontologies. This authoring tool allows the definition of an ontology and the managing of the content of an ontology. Such content of an ontology may be stored in a Tbox and Abox. A Tbox is a set of data comprising atomic concepts, complex concepts, which consist of recursive combinations of atomic concepts as well as bottom and top concepts.

An exemplary Tbox may include the following concepts:
A general concept defines that it has either the value of male or female.
The concept of a person is defined by all males and all females.
The concept of a sibling is defined by the concept of a person, where the person is either a brother or a sister of another person.

The Abox includes instances of the concepts provided by the Tbox as well as their relations to each other.

The result of such an ontology authoring process will then be stored in the ontology store or ontology repository.

The above mentioned concept resolution service is capable of resolving such concepts stored in the ontology repository to detect differences and ambiguities between different representations of the same underlying concept both within and across terminologies. In other words, the concept resolution service may determine whether a particular entity of an ontology, such as a term or concept, is in contradiction to the remaining ontology. The concept resolution service may also perform such a determination regarding an entity of one ontology within a different ontology to find ambiguities between the two ontologies.

Figure 3A:
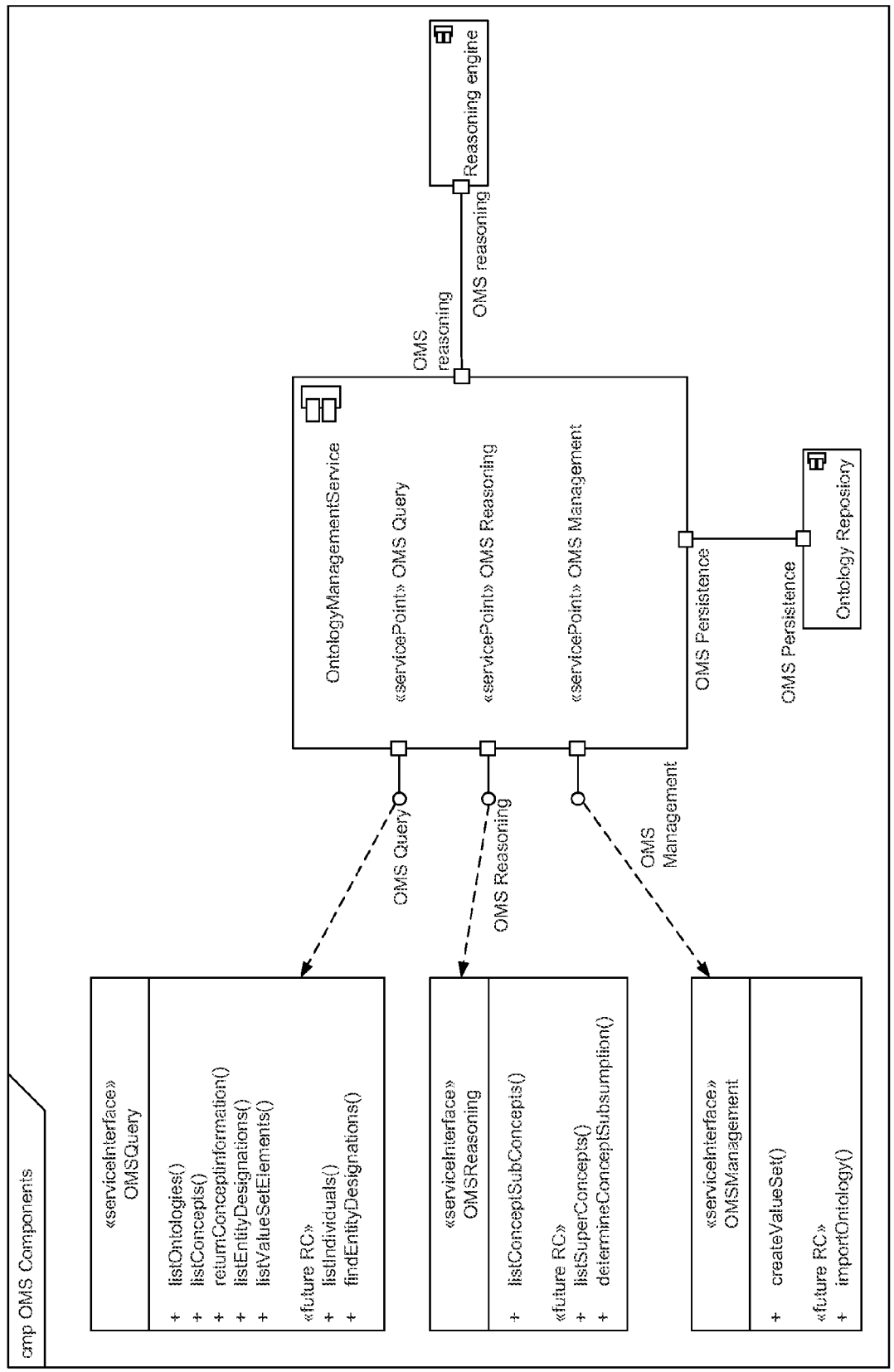
FIG. 3a illustrates the basic structure and purpose of the ontology management service of FIG. 2a in more detail according to an embodiment of the present invention.

According to an embodiment of the present invention and depicted in FIG. 3a, the semantic infrastructure further comprises an ontology management component, also referred to as ontology management service (OMS). This ontology management component provides a standardized service for managing at least one ontology and mappings between members of different ontologies. In particular, the ontology management component provides services for managing, querying and reasoning across ontologies.

According to the embodiment illustrated in FIG. 3a, the ontology management service provides access to the ontology repository and associated functionality for managing ontologies and terminologies, such as code systems. These code systems may be large externally supplied standards, such as SNOMED, or small locally configured code sets, i.e. a list of enumerated values (e.g. Male, Female, Unknown for Gender).

The ontology management component further provides for the creation and management of a value set which is a sub-set of one or more terminologies, or more general one or more ontologies.

In a preferred embodiment, a value set is a sub-set of a particular terminology, such as SNOMED or MedDRA. For example, a value set may comprise terms and relationships between the terms for a particular area of information. Such a value set may include a sub-set of a terminology relating to, for example, medicine prescribed normally for a particular disease. Another example of a sub-set of a terminology may include terms and its relations for possible diagnoses of, for example, headache.

Thus, when interpreting a terminology as a tree of nodes, a value may define a particular node and all its sub-nodes. In a further embodiment a value set may comprise a first node of the tree and a predetermined set of nodes connected to this first node directly or via other nodes. Thus, a value set reflects a sub-group or sub-set of a terminology.

In a further embodiment of the present invention, a value set includes more than one value set of different terminologies. For instance, a value set may comprise all medicinal products against headache from a plurality of the terminologies. It has to be noted that the present invention is not restricted to a particular value set, as outlined above. Moreover, the present invention includes all combinations of values or notes or terms or relations within one or more ontologies or within one or more terminologies. Thus, a person skilled in the art will be aware of the variety of possible value sets that can be built from one or more ontologies.

Referring back to FIG. 3a, the ontology management component or service (OMS) creates such a value set by providing an ID identifying this particular value set, and storing this ID and corresponding information on the at least one sub-set of at least one terminology within the ontology repository. As an example only, the OMS may store a value set ID and IDs of the nodes and relations from the terminologies making up the value set, or the ID of a node and a subsetting expression that may be evaluated at run time to a discrete set of individuals or concepts.

In an embodiment of the present invention, the ontology management component or service further provides for terminology mappings between members of different ontologies. Such a mapping may be made between a pair of nodes, one from a first ontology and one from a second ontology. As an example only, such terminology mappings may be made between MedDRA and SNOMED or any other standardized ontology. As an example, the ontology management component can manage a domain of terms representing the SNOMED terminology (Systematized Nomenclature of Medicine terminology), or the MedDRA terminology (Medical Dictionary for Regulatory Activities terminology).

As will be appreciated by a person skilled in the art, a terminology does not need to be a standards terminology, but may also be a local terminology, for example from a particular organization. The OMS allows for managing all of these terminologies as well as for mapping between these terminologies.

A further functionality provided by the OMS as depicted in FIG. 3a, is a query service. Such query service allows to list one or more of the ontologies stored in the ontology repository or to list concepts of the stored ontologies. A further query service may provide a list of value sets which have been authored and stored in the ontology repository. This service may also provide the elements of each value set.

According to a further embodiment, the OMS provides a reasoning interface to communicate with a reasoning engine. Amongst others the reasoning engine provides services to reason across one or more ontologies to draw inferences. Such reasoning may determine whether specific elements match an ontology or are in contradiction to that ontology. For example, the prescription of a particular medicine against a diagnosed disease may be checked against an ontology. If the reasoning engine finds for example a side effect of the prescribed medicine which is in contradiction of the diagnoses, the OMS allows for reporting such contradictions with the underlying ontology.

Again, with respect to FIG. 3a, the ontology repository provides for storage of value sets, ontologies and mappings between the members of different ontologies. The ontology repository may be part of the ontology management component or may be an independent component. In any case, such an ontology repository may be implemented as a data base. As will be appreciated by the person skilled in the art, a database of the ontology repository may be an object-oriented storage model. In a further embodiment, the ontology repository is a relational database system. In any case, the ontology repository is capable of storing items such as terms, relations between terms, complete terminologies, ontologies, sub-sets of terminologies, and value sets, as outlined above.

In accordance with an embodiment of the present invention, the ontology repository allows for storage of mappings between members of different ontologies. Such mapping may be accomplished by pointers to a member of one or more ontologies stored in the ontology repository. A member of an ontology may be a particular node or relation within the tree-like structure of the ontology. Thus, a member of an ontology may be a particular term of an underlying terminology, a particular concept or an identification value identifying a term or concept. A member of an ontology may also be a value set, i.e. a sub-set of an underlying terminology.

Figure 3B:
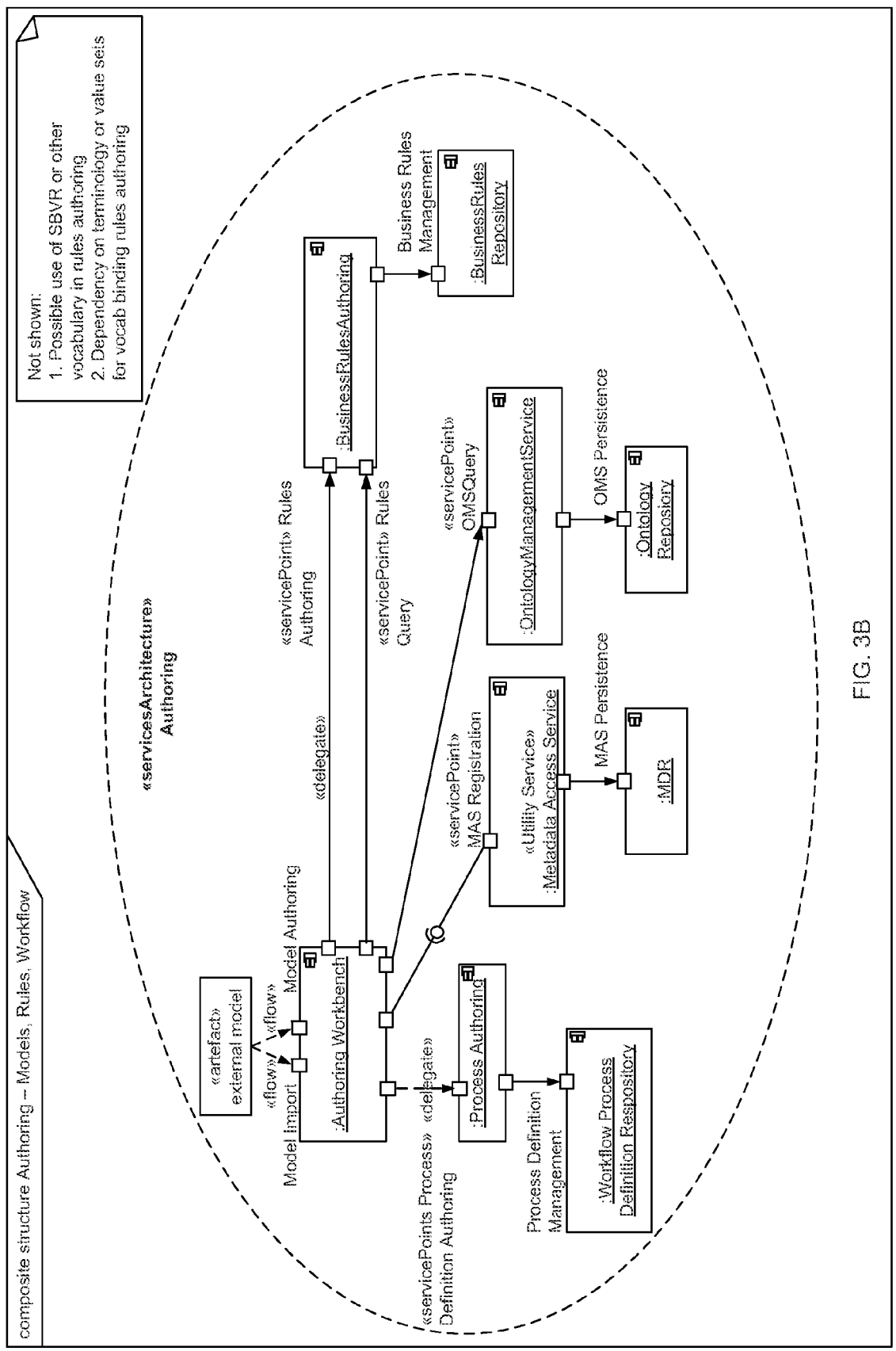
FIG. 3b depicts the service architecture of the authoring sub-system of FIG. 2a according to an embodiment of the present invention.

Turning now to a further component depicted in FIG. 2a, i.e. the authoring work bench. As briefly mentioned above, the authoring work bench provides an integrated tooling environment for definition and management of information models, rules, processes, rule-based terminology binding, and system configuration data. This plurality of services and components is illustrated in FIG. 3b.

The authoring work bench provides a flexible, configurable design time environment to support various domains and applications at runtime. In other words, while the authoring is performed during design time, the results of the authoring are stored in a way to support domains and applications at runtime. While newly created rules and workflow processes are stored in native repositories, as outlined above, the information models and system configuration information are published to and registered with a meta data repository or meta data registry. A meta data access service (MAS) provides for access to the meta data repository or meta data registry (MDR).

With respect to an embodiment of the present invention, the platform includes an information model management component that is utilized for managing information model schemas. These information model schemas are created using the authoring work bench. Such an information model schema defines an information model for a particular domain. For instance, the authoring work bench can be used to define models based on the H7 standard.

According to an embodiment of the invention the platform includes an information model repository for storing information model schemas. The information model schemas may be stored during the authoring process. Further, the information model repository can also store the information models instead of or in addition to the MDR. In an embodiment, the information model repository is included in the information model management component. However, the present invention is not restricted to such an information model repository, but also comprises an information model repository which is part of the MDR or which is an independent component.

As an example only, an information model may be employed with a hospital application to reflect the information regarding a particular patient within the hospital or during a clinical observation. Thus, parts of such an information model would include objects such as a patient object, an object for clinical observations, and/or an object for suspected diagnosis. As an example, the patient object may include a particular field for the gender of the patient. This field may then be linked to a gender object which comprises particular options of the gender of the patient. Examples of these gender options are male, female, unknown, hermaphrodite.

As can be seen from the example above, an information model represents an ontology of a particular domain model for using an object-oriented approach. It has to be noted that the present invention is not limited to object-oriented models, but also includes information model definitions using other database types such as relational databases.

Referring back to FIG. 2a, the information models are used to generate executable templates such as semantic data graphs which then can be used to generate example object instances, such as instance data graphs, to validate runtime instances and to automatically transform between different formats. Examples of these formats are XML, XMI or Java objects. Sources for models may be from industry standard domain models, such as the HL7 or created for specific applications or domains for an organization.

An important aspect of defining models is to define the vocabulary constraints for coded information model slots. These slots use "value sets" which are anything from a small simple enumerated list of codes to a complete terminology such as SNOMED-CT.

As outlined in the examples above, an information model may comprise a patient object which further points to the gender object of that model. However, the present invention is not restricted to these flat ontology relations.

Figure 3C:
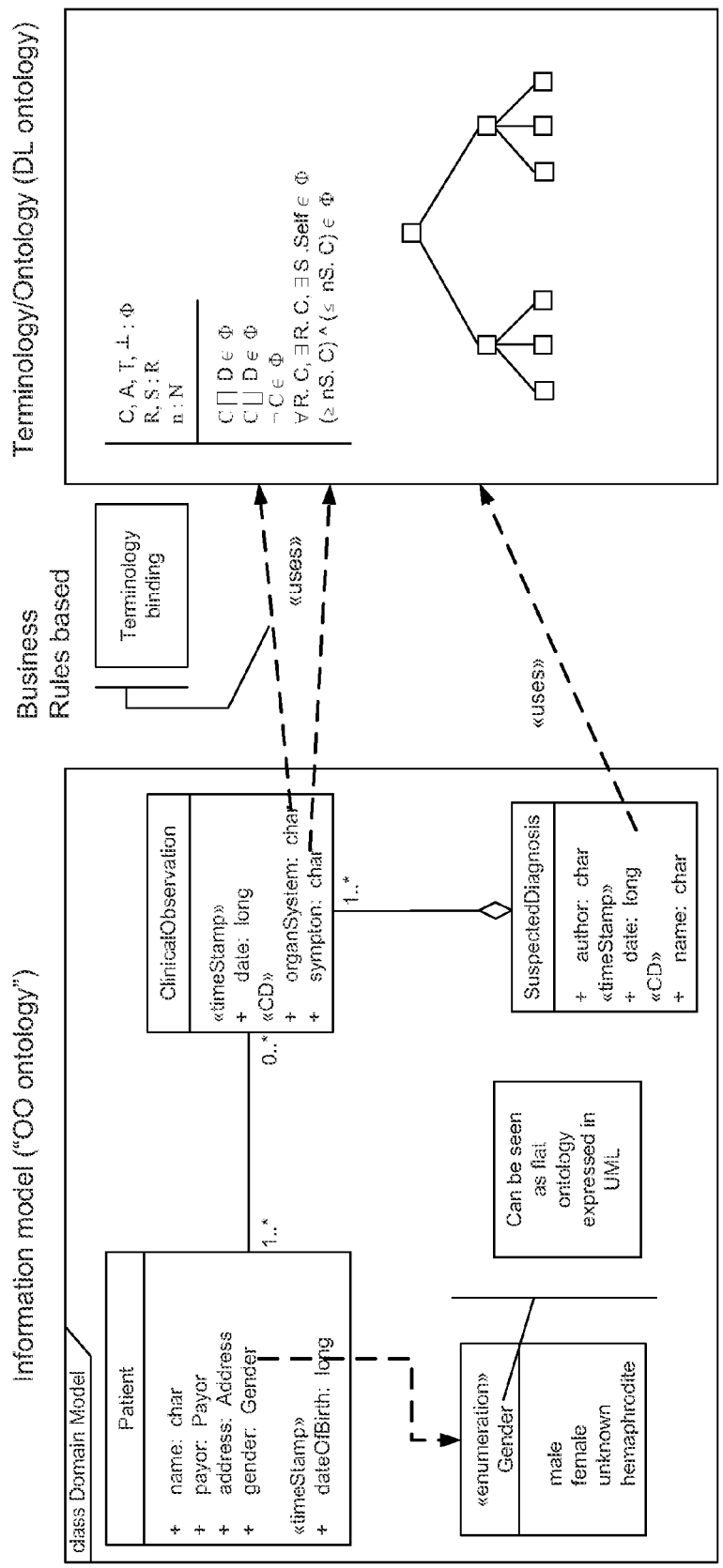
FIG. 3c illustrates the rules based mechanism for binding between information models and ontologies in accordance with an embodiment of the present invention.

Referring to FIG. 3c, an exemplary information model is depicted that may be bound to a terminology or ontology of the semantic infrastructure and stored in the ontology store.

Again, with respect to the above example of the information model for a clinical observation, the clinical observation object may provide slots or coded slots to which a particular value set or sub-set of a terminology and/or ontology can be bound. For instance, such a slot may refer to an organ system, while another slot may refer to a symptom identified with the patient. These slots can be bound to the terminology via business rules which will be explained in more detail below.

In accordance with an embodiment, each slot within an information model may include a pointer pointing to a rule stored in a rules repository. The rule itself may include one or more pointers to value sets stored in the ontology repository. Thus, a dynamic binding of particular value sets to a slot can easily be accomplished. In particular, during design time, the slots of the information model are bound to a particular business rule or element of the business rules which itself has a link to the terminology of the ontology repository. In an embodiment of the present invention, the business rules repository stores conceptual rules. Such a conceptual rule can include a pointer to a value set stored in the ontology repository.

During runtime, an instance of the above discussed information model for clinical observations will then arrive at the coded information or coded slot of a particular object instance. Since the coded slot is bound to a conceptual rule, a rules management component, such as the business rules management component of FIG. 2a, can be utilized for executing the linked conceptual rule. Such a rule execution may involve querying the rules repository or business rule store to retrieve pointers to the value sets stored in the ontology repository and then to retrieve value set data from the ontology repository. Thus, one or more value sets can be dynamically bound to one or more slots in the information model.

As an example only, if a member of the staff of the clinical observation uses the platform of the present invention, a new entry in the instance of the clinical observations object will be necessary. The system of the present invention allows for retrieving value set data from a terminology or ontology to fill out the clinical observation data. Thus, an application running on the platform of the present invention retrieves a particular conceptual rule via the rule binding of the information model slot. The rule itself is bound to the value set of the terminology. In an embodiment of the present invention, the medical staff will retrieve a list of choices to fill in particular data into the slot of the clinical observation data. The list of possible values is retrieved from the ontology repository and is defined by a particular value set stored therein. Utilizing a value set identifier, a value set can be identified within the ontology repository that is obtainable from the ontology management service. In a very simplified form, the slot of the information model refers to an ID (identification) of a business rule or conceptual rule in the rules repository which itself includes an ID to a particular value set within the ontology store.

Referring back to FIG. 2a, a further component is the system configuration management component which manages configuration information on the configuration of each system component, i.e. each platform component. Further, the system configuration component utilizes services of the rules management component, information model management component and ontology management component to dynamically bind one or more value sets to one or more of the slots of an information model. In particular, as mentioned above during runtime the system configuration component, for example the meta data access service thereof, may access an information model stored in the MDR. When interpreting the model the system configuration component recognizes a slot in the information model and accesses the services of the information model management component, rules management component and ontology management component to perform the above discussed binding of a value set to the slot.

In accordance with another embodiment it is the information model management component which utilizes the rules management component and ontology management component to perform the binding of a value set to the slot.

A further aspect of the system configuration management component is a service for querying the information models. Thereby terminology binding operations utilizing services of the rules management component and the ontology management component are executed.

The system configuration management component further provides the capabilities for managing the configuration of both the platform and applications that may be built on the platform. This provides mechanisms to store and dynamically manage and use configuration information that enables very flexible approaches to be taken to application development and deployment. The system configuration management component consists of a meta data access service and the meta data registry and repository. The creation of configuration information has been mentioned above with respect to the authoring work bench sub-system which also includes configuration information authoring functionality. After creation of configuration information it may be published to the meta data registry and is stored in the meta data repository.

Further, the system configuration management provides a service configured for querying configuration information from the meta data registry. In particular, the system configuration management consists of a configuration management service which provides a service interface that enables components to obtain details about their configuration which enables a dynamic management of the platform and applications. It also provides a common access mechanism for querying configuration information stored in the meta data registry and/or other sources.

Finally, a semantic data graph service is part of the system configuration management that provides a service interface specifically for obtaining semantic data graphs which are also authored in the authoring work bench sub-system and registered in the meta data registry as outlined above. The system configuration management provides a configuration service that provides a common interface for accessing configuration data for all components of the computational semantics and infrastructure platform and any application components built on that platform. A system component will generally access the configuration service in order to obtain relevant configuration data during system initialization. A component that interacts with the users may also obtain user-specific configuration data when a user logs on. Finally, the configuration service also provides an interface that allows for components to subscribe for notification of configuration data changes to enable dynamic re-initialization during system operation.

The configuration service further does not actually store configuration data itself, but provides a consistent means for accessing such data that may be obtained from various backend sources. Meta data on the sources for various areas of configuration data are stored in the meta data repository (MDR). The configuration service accesses the MDR via the meta data access service (MAS) as necessary to obtain configuration meta data. Such a meta data access service as well as further interfaces and services of that MAS are depicted in FIG. 3d.

The MAS uses the meta data information in order to obtain the actual meta data from backend sources and construct a response to a client configuration query. The editing of configuration data is handled externally to the configuration service via the authoring work bench. However, the configuration service provides an interface to be used by the authoring work bench to publish a notification that the configuration data in a certain area has been changed. This notification is then forwarded by the configuration service to all client components that have subscribed for notification of changes to that configuration area.

In an embodiment of the present invention, the meta data registry provides an ISO11179-based registry and repository for managing overall meta data. The meta data registry and repository provide a data base for storing and retrieving meta data about the system. It is based on ISO11179 meta data registry standards. It can act as both a registry of meta data but also as a repository of information such as the system configuration information authored using the authoring work bench. Entities that are registered in the MDR can either include actual physical artifacts or location references to where these artifacts are stored.

Figure 3D:
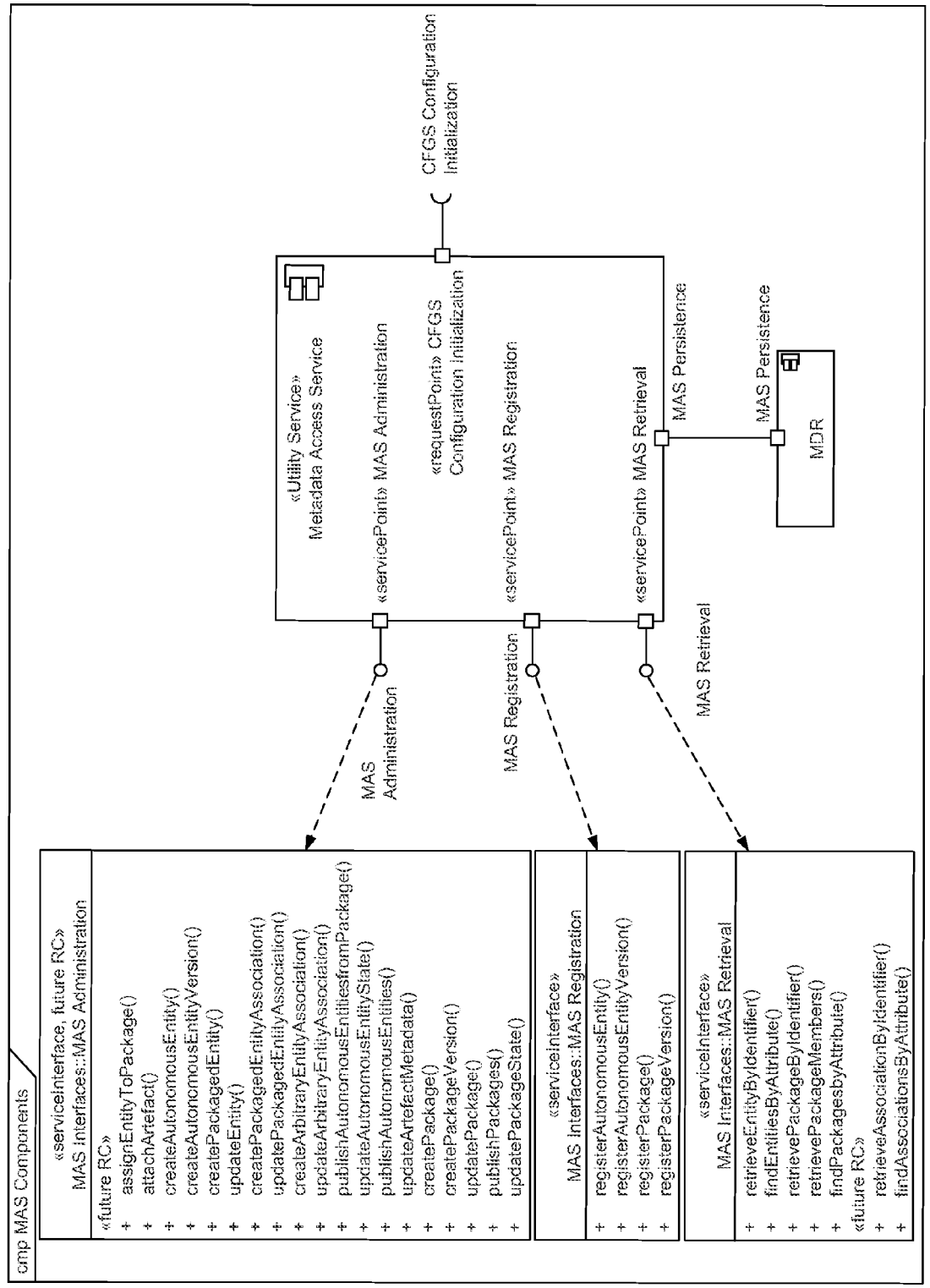
FIG. 3d depicts the components of the Meta data access service and Meta data registry according to an embodiment of the present invention.

The meta data access service as depicted in FIG. 3d provides a set of service interfaces for managing and retrieving the information and the MDR. The retrieval interface provides query capabilities. The registration interface provides the ability to publish information to the MDR that is authored elsewhere, while the administration interface provides the ability to author content directly in the MDR and provide curation.

Again, with respect to FIG. 2a, the depicted semantic data graph service provides capabilities for retrieving, transforming, and validating semantic data graphs. Such semantic data graphs are information model templates which define the information structures that are used by components and services to instantiate and/or validate individual instances, e.g. an instance data graph.

Figure 3E:
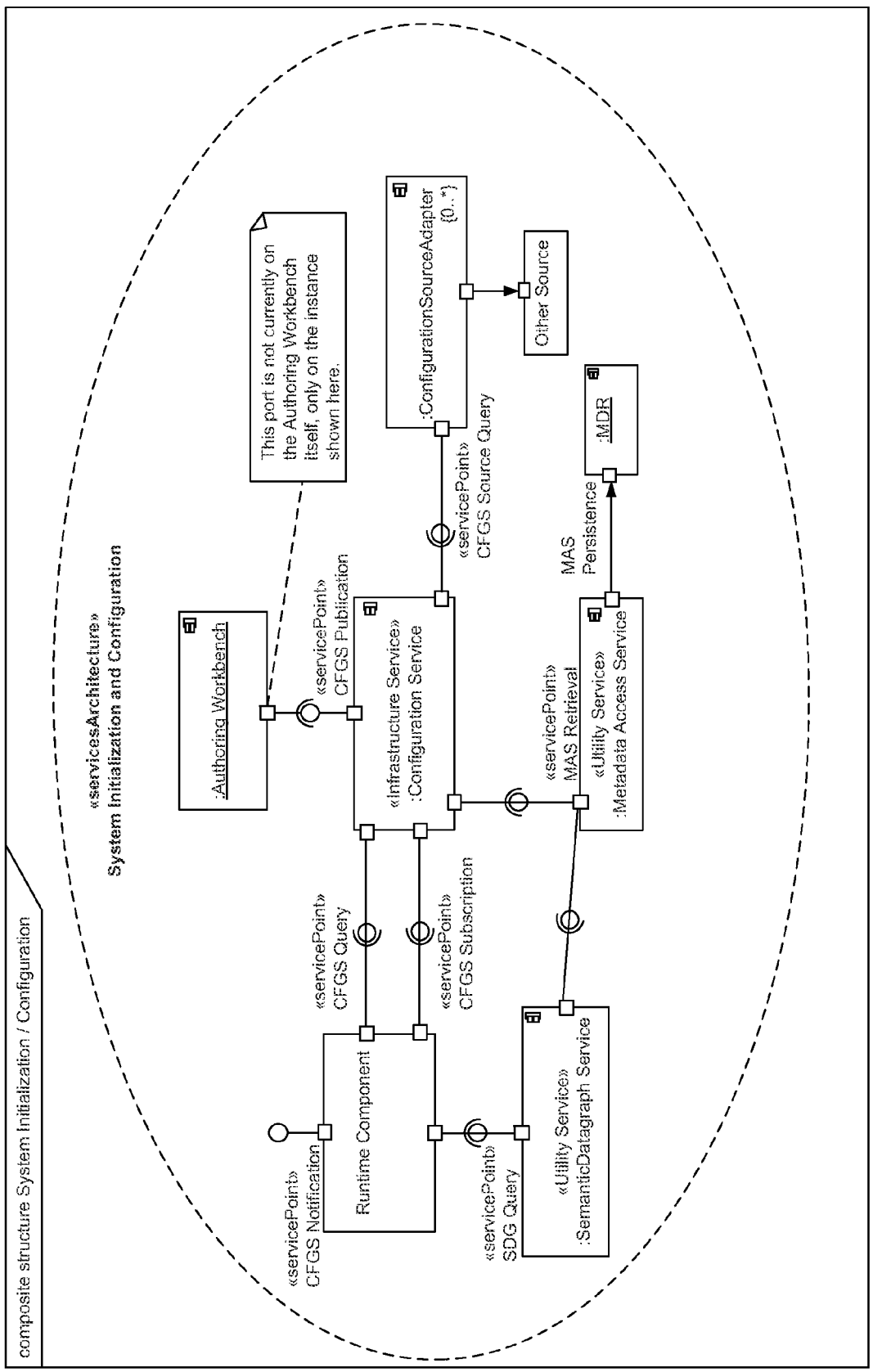
FIG. 3e illustrates the services and components for system configuration and initialization of services and application components in accordance with an embodiment of the present invention.

The instantiation of data graphs and other objects takes places at the initialization of the components or sub-systems of the platform. Therefore, configuration and initialization services are depicted in FIG. 3e which are employed during initialization of services and application components. This is supported by a set of capabilities, which are able to support multiple organizations and domains. The interrelation of the configuration and initialization services is also depicted in FIG. 3e. As can be seen, the authoring workbench services and metadata access services, which have been described above, are also involved during configuration and initialization.

During design time the configuration data is defined, i.e. configuration information is authored in potentially a number of places, such as directly into the Meta data registry using the authoring workbench, in LDAP directory for user specific items, into XML configuration files using IDE tooling etc. In all cases location information is entered into the MDR via the authoring workbench so that it has a complete picture of all the relevant configuration information for a component.

When a system, subsystem or even only a specific service or component is brought up a call is made to the configuration management service to retrieve the appropriate configuration settings for that component. The configuration management service firstly queries the MDR via the metadata access service to retrieve the locations of all of the relevant configuration settings including the actual settings, where they are held in the MDR itself. The configuration management service then accesses other sources through appropriate adapters and compiles all of the information for return to the calling component. The settings are then used to complete the initialization of the component. If the settings include identification of one or more semantic data graphs then an additional call is made by the component to retrieve the semantic data graph definitions. Such semantic data graph definitions provide information model templates for instantiating specific information structures for use by the component. A semantic data graph service also retrieves the actual semantic data graph definitions from the Meta data registry.

At various times a component maybe reinitialized, which would result in a repeat of the above sequence. The configuration management service also supports a publish and subscribe mechanism, which enable components to request to be notified when certain configuration settings change so that the re-initialization can be triggered.

Finally, a user may have user-specific configuration settings which are loaded at session start. Again a similar set of interactions occurs, except that the main source for the actual settings will usually be a LDAP (Lightweight Directory Access Protocol) Directory Referring now to the information management services depicted in FIG. 2a. The information management sub-system provides the capability for persisting transactional information in a standardized extendable fashion. This includes two services, the information management service (IMS) and the identity resolution service (IRS).

Figure 3F:
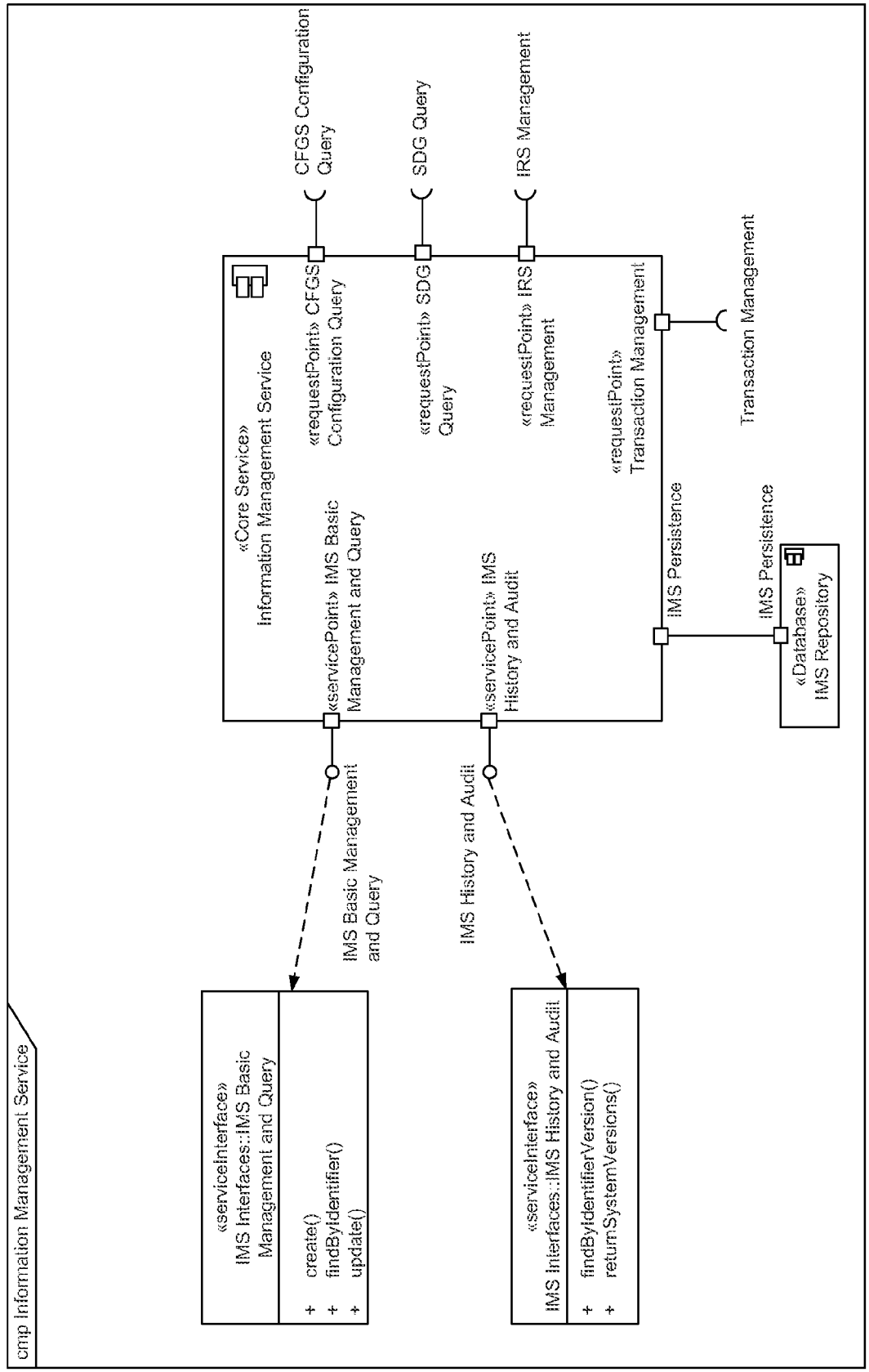
FIG. 3f depicts the components of the information management service in accordance with an embodiment of the present invention.

The information management service is depicted in FIG. 3f in more detail. The IMS provides a very simple persistence model for storing semantic data graphs. It provides operations for storing and retrieving graphs and provides transactional management of indexes to the graphs using IRS. Further, the interface is configurable to be able to store and retrieve any type of information. Physically the information is stored as a BLOB or CLOB and so can easily be modified or extended. IMS provides only identified-based retrieval while attribute-based searching is provided by the IRS.

The IRS provides identity management and an indexing and search capability for semantic data graphs stored by the IMS. When a new or updated semantic data graph is to be persisted by the IMS, it extracts a configurable set of attributes from the graph and passes them to IRS, which generates an identifier and persists the attributes as a set of name value pairs. In an exemplary embodiment of the present invention the initial physical implementation uses Lucene.

Coupled with the information management service, this provides an extremely flexible and configurable solution for persisting and very fast searching and retrieval of transactional information.

Figure 3G:
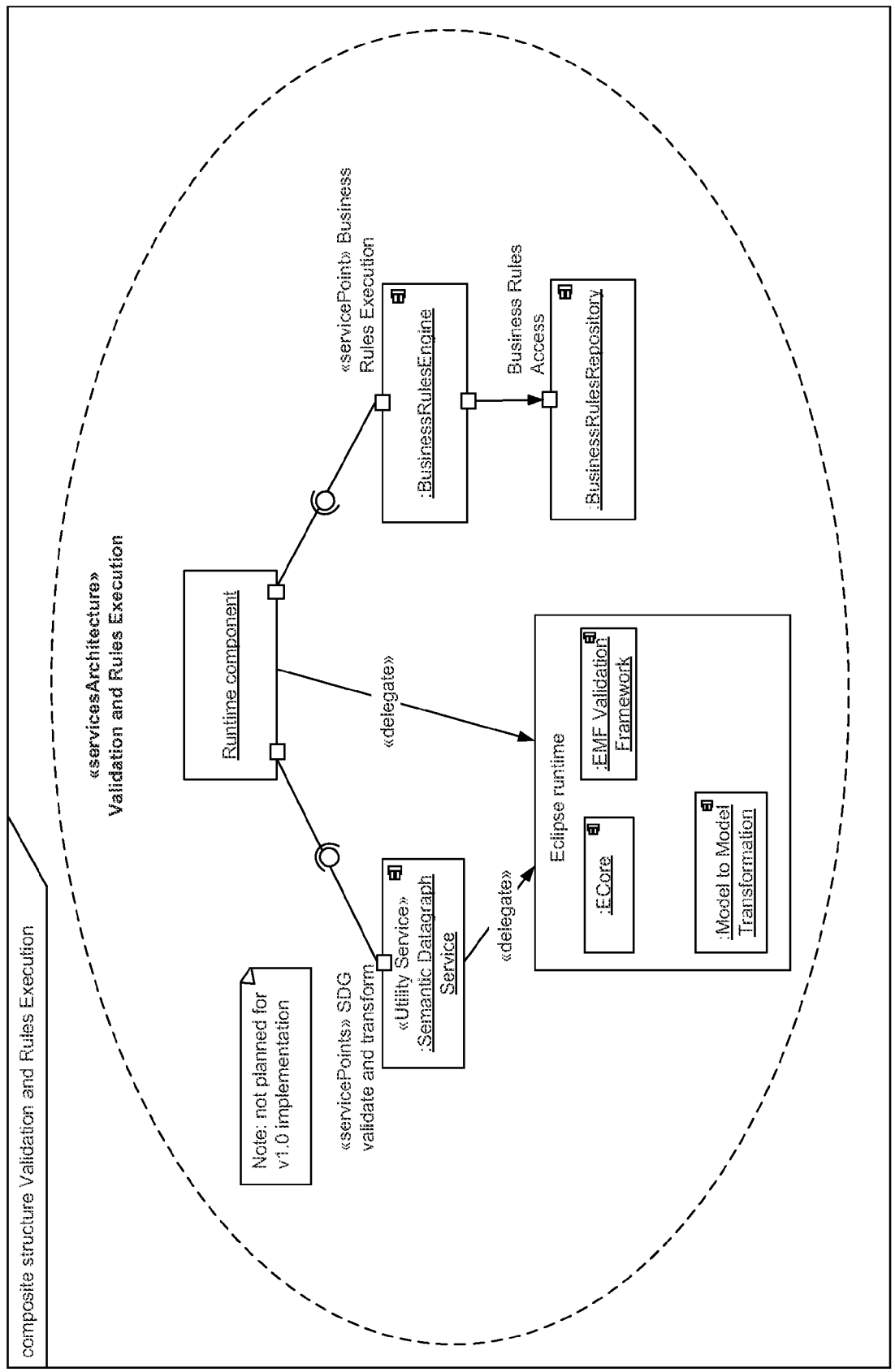
FIG. 3g depicts the services and components provided for validation and logic rules execution in accordance with an embodiment of the present invention.

Referring now to FIG. 3g, a very generic abstracted view is illustrated to describe the general capabilities provided for validation and logic rules execution. The runtime component could be any application or service component which triggers any validation. Hard coding of validation or other logic is strongly discouraged and two mechanisms are used to provide more declarative behavior. The first is the eclipse ECore engine, which provides validation and transformation of IDGs. The second is through the use of a commodity business rules engine, such as a JBoss rules. The semantic data graph service also provides a validate operation, which provides a service facade to allow for remote execution of IDG validation or transformation. In addition to validation, a business rules engine provides general rules execution capabilities, i.e. a mechanism to provide business logic actions, e.g. identifying and prompting the user of the need to enter death certificate information in the event of a patient death or setting a higher priority for treatment of specific classes of patients.

Referring back to FIG. 2a, the semantic infrastructure also includes the medicinal product management service (MPMS) employed by the ontology management component. The medicinal product management service creates and maintains identification information identifying terminologies associated with a medicinal product. The MPMS is based on the ontology management service and ontology store. The MPMS provides capabilities for managing and querying information about medicinal products. This information is being persisted as an ontology to allow for reasoning to be applied to medicinal product information. It basically provides a coarse grain wrapper for the ontology management system that is specialized to the medicinal product ontology.

Further, the MPMS provides services for mapping between medicinal product terms and particular terms stored as members of one or more ontologies. As noted above such mapping may be accomplished by pointers to a member of a particular ontology stored in the ontology repository.

Figure 3H:
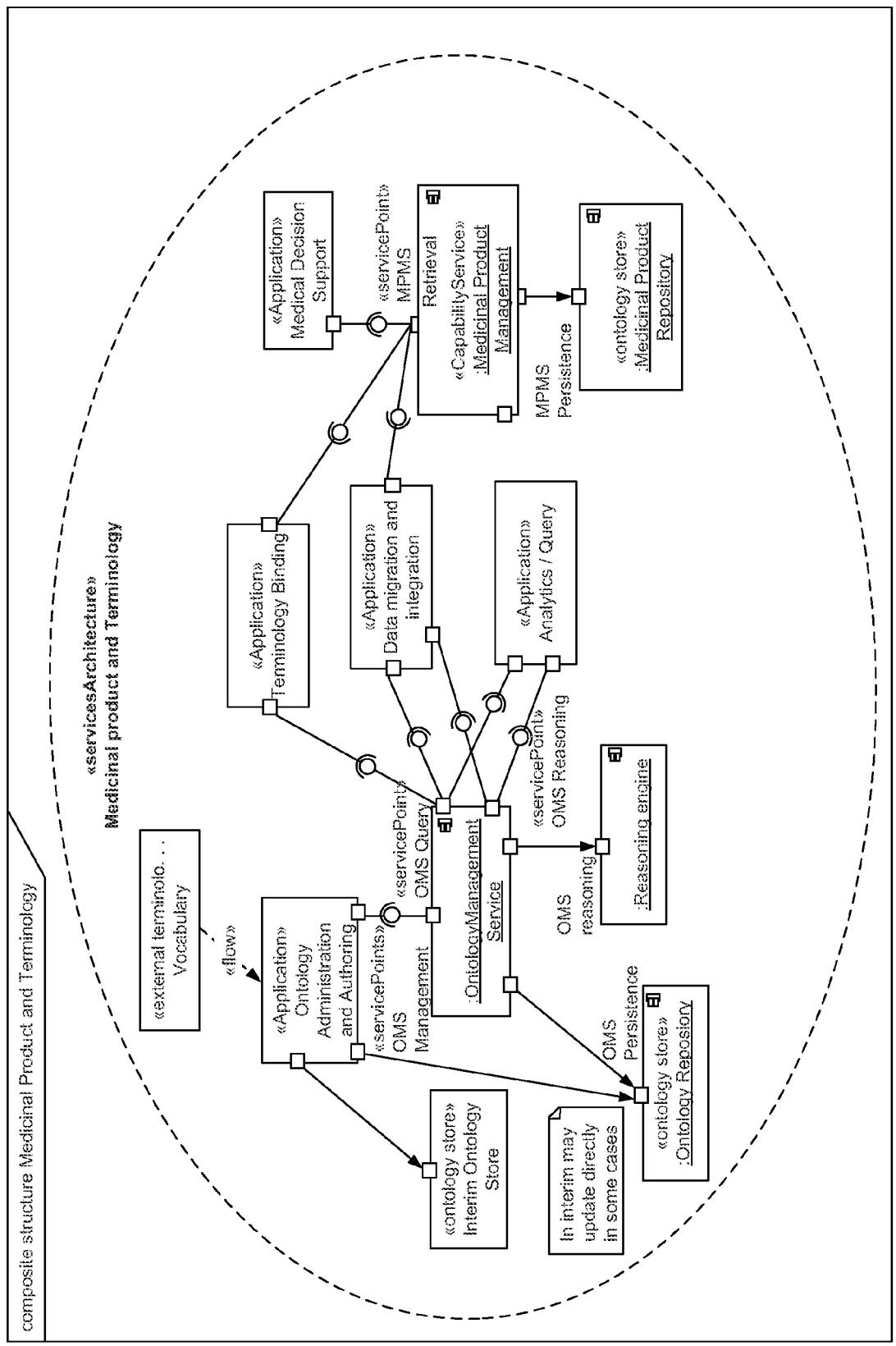
FIG. 3h illustrates the components and services employed for the semantic infrastructure in view of medicinal products and terminologies according to an embodiment of the present invention.

FIG. 3h illustrates the composite structure of medicinal product and terminology services. The medicinal product and terminology services provide the ability to manage and use information in the form of ontologies. This uses "semantic web" technologies to provide intelligent management of medical terminologies and other ontologies as well as the ability to "reason" across those ontologies to draw inferences.

The platform provided by the present invention provides two key capabilities, i.e. the ontology management service and the medicinal product management service. These services are relatively stand alone, although they use some of the same technology for implementation and those are deployed on the main core infrastructure of the system of the present invention.

According to a different embodiment, the present invention provides a system for efficient and robust data exchange and transfer of unambiguous medicinal and drug safety concepts independent of the underlying terminology standard. An embodiment of the present invention relates to a formally defined process for defining specific structures to be exchanged between machines, i.e. a "data exchange standard".

Figure 4:
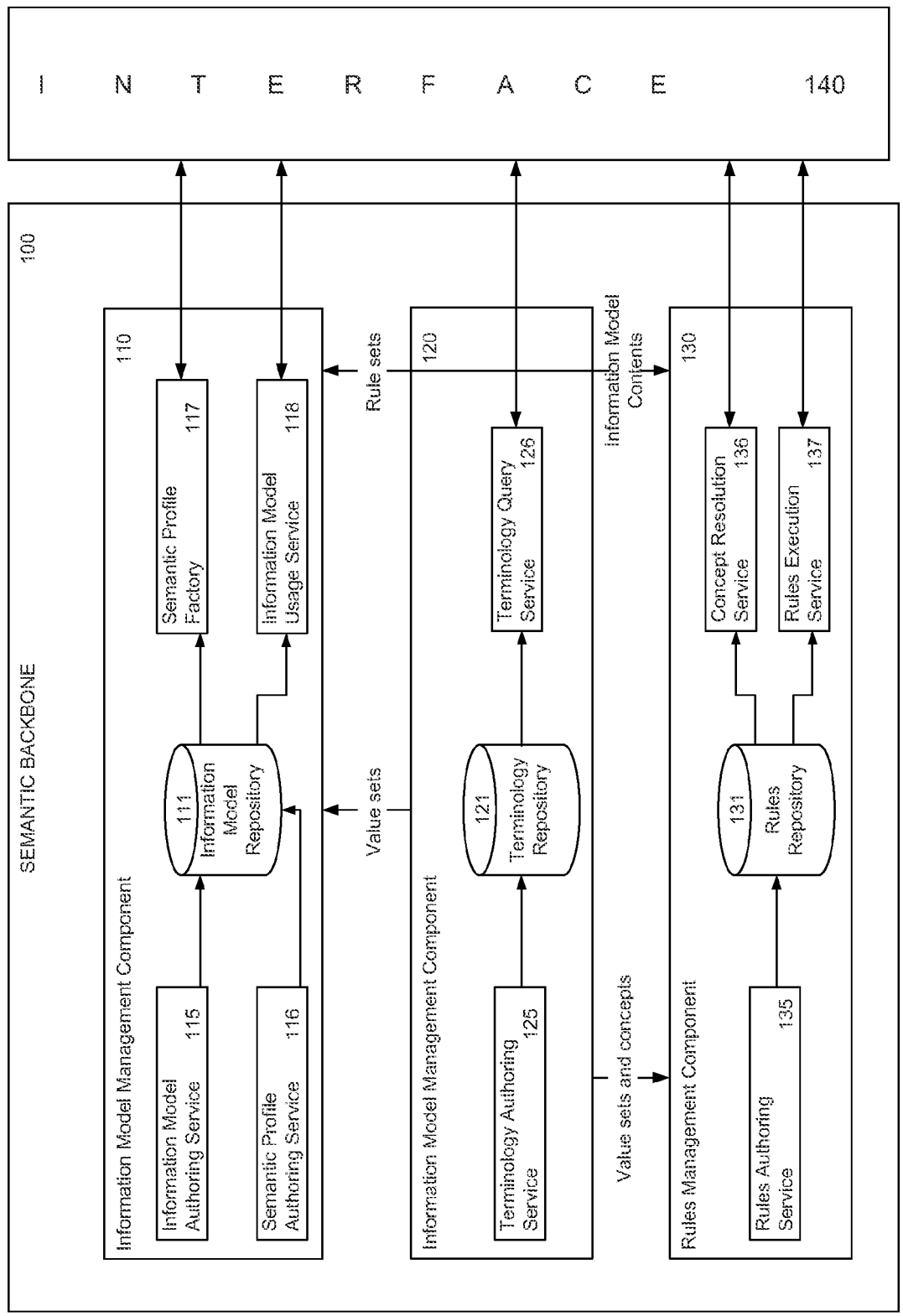
FIG. 4 depicts the 3 tier architecture of a semantic backbone in accordance with an embodiment of the present invention.

According to FIG. 4, the system of the present invention provides a core service having a three tier architecture. As depicted in FIG. 4, the core service is divided into three components of functionally similar services. The skilled person will appreciate that the core service may be implemented using a different architecture than the depicted three tier layers. For instance, the services of the present invention maybe implemented in a single layer system.

Returning to FIG. 4, a semantic backbone 100 is shown which includes at least three components. These components include an information model management component 110, a terminology management component 120 and a rules management component 130. Each of these components is capable of instantiating services, which collaborate with one another, either as a consumer or as a provider of the functionality of the respective service.

According to an embodiment of the present invention, these services are implemented as objects of Java classes. The Java environment provides for object oriented programming and the instantiation of objects from classes. The classes may further inherit behaviour, data types and other properties from other classes, allowing a simple programming scheme while improving interoperability of object instances. As will be appreciated by those skilled in the art, any other available programming scheme may be used to implement the services described in more detail below.

As an example, the information model authoring service 115 may represent a provider of functionality. In particular, a user, such as an information management specialist, may be provided with the functionality of creating, editing and/or deleting an information model by the information model authoring service 115. On the other hand, the concept resolution service 136 may be a consumer of functionality. For example, when requesting value sets from the terminology management component 120 via a terminology query service 126, the concept resolution service 136 is a consumer of the service 126. Moreover, the concept resolution service 136 may also be a provider of functionality, such as providing data relating to a particular concept or business rule to another service.

Further, the terminology management component 120 and the rules management component 130 may also include a terminology authoring service 125 and a rules authoring service 135, respectively, providing similar functionality as service 115 above. These services provide a user with functions, such as authoring, i.e. creating, editing and/or deleting, terminologies or particular terms, and business rules or concepts, respectively.

The information model management component 110 may further include a semantic profile authoring service 116 and a semantic profile factory 117. These services allow for constructing, employing and requesting semantic profiles representing groups of semantically similar terms of at least one model. Moreover, a semantic profile may group terminologies of multiple information models which are semantically similar. However, the present invention is not restricted to such semantic profiles, and additional profiles may be built and stored within the scope of the invention.

Continuing with the description of FIG. 4, the component 110 may further include an information model usage service 118. The service 118 provides functionality to other services for requesting information model data. For instance, the service 118 may be used to retrieve particular data regarding data types of the ISO 21090. Other data of the information model management component that could be requested may relate to other standards, such as BRIDG or HL7 RIM. Each of these standards specifies a particular information model of healthcare or medicinal terminologies representing a particular model of a domain of terms.

With respect to the terminology management component 120, a terminology query service 126 can be employed to retrieve a particular mapping. Any service of the information model management component or the rules management component may call this service to request a term or terminology based on information of another standard, information model, business rule, concept etc. As will be outlined in more detail further below, the terminology management component allows for "translating" between different standards, concepts, terminologies etc. It is to be understood that within the scope of the present invention, other services may also use the terminology query service 126, such as services of the components 110, 120 and 130 not being depicted in FIG. 4 or even services of additional components (not shown) of the system.

Further, the rules management component 130 may comprise a rules execution service 137 that allows for realization of each of the rules or concepts provided by the rules management component 130. As an example, such a concept may be provided by the SNOMED standard. SNOMED provides a hierarchical terminology which can be scanned vertically or horizontally. A vertical scan may, for example, begin with a generic term or superordinate concept followed by an infraordinate term, subtopic or particular term of the SNOMED dictionary. In other words, a concept or rule specifies the path on how to retrieve a particular item within the respective concept, such as a particular term of a dictionary. The rules execution service 137 can therefore be called by other services to request the path for deriving an item within a particular concept.

Another provider of concepts may be a pharmaceutical company or other producer of medicinal relevant substances, apparatuses, instruments etc. As will be explained in more detail below, each company may provide its own "standard" on how to define drugs, their ingredients or their field of application. This will make up a concept which can be maintained in the rules management component 130 via rules authoring service 135.

According to an embodiment of the present invention, each of the three components 110, 120 and 130 comprises a repository for storing corresponding data. Thus, the information model management component 110 comprises an information model repository 111 for storing value sets including information comprising particular terms. As mentioned above, the stored information models may be based on standards such as BRIDG, HL7 RIM or ISO data types. Each of these standards provides its own "dictionary" of healthcare related or medicinal terms which may be represented by an information model created via the information model authoring service 115. Further examples of such dictionaries are the SNOMED dictionary, the MedDRA dictionary or the HL7 Common Terminology Service (CTS II) dictionary.

The terminology repository 121, on the other hand, stores information which helps to map between all different concepts or standards. As an example of the present invention, the terminology repository 121 may contain data tuples consisting of two pointers. One pointer is directed to a term of the HL7 RIM stored in the information model repository 111, while the second pointer is directed to a term of the SNOMED model, where both terms have the same meaning.

For instance, in a preferred embodiment the terminology repository includes a standards based implementation (HL7 CTS II), terminology mappings (initially SNOMED to MedDRA), standard and local (organization specific) terminologies, and a terminology Browser (SNOMED, LOINC, ICD-9/10, etc). The terminology repository has, for example, capabilities, such as authoring, querying (high performance runtime provision of value sets), supporting simple and complex, well formed and badly-behaved terminologies, and may require additional functionality to support more complex navigation capabilities.

Further, the terminology repository 121 may also provide pointers to a particular concept stored in the rules repository 131 and to an entry in the information model repository 111 to link a concept to a particular terminology. It will be apparent for the skilled person that other pointer tuples are possible than the two provided in the above examples.

It is also to be noted that the terminology repository 121 may further be adapted to store other data than tuples of pointers to provide a mapping between the repositories. All of these mapping combinations and data types used to store information in the terminology repository 121 fall within the scope of the present invention. In addition, in an embodiment of the present invention the terminology repository may store dictionaries instead of or in addition to the information model repository. In such a case, the mapping implemented by the terminology management component 120 can be realized by storing data pointing to a model in the information model repository 111 or in the rules repository 131 together with a term of a dictionary. On the other hand, the tuples may again include two pointers, where one is directed to a data item of the terminology repository 121.

As will be appreciated by those skilled in the art, each of the repositories 11, 121 and 131 is implemented as a database system according to an embodiment of the present invention. Such database systems may be implemented by any available database. The database may be accessible via a direct bus connection of a computer system implementing the invention. On the other hand, the repositories 111, 121, and 131 may run on a network computer system, such as a peer-to-peer device. In this case, the services of components 110, 120, and 130 will connect to the repositories 111, 121, and 131 via a network connection, such as a local area network (LAN) or wide area network (WAN) or using any other suitable network technology.

Since the components 110, 120 and 130 are bound to each other via their respective services, the semantic backbone 100 allows for semantic interoperability as well as translation between different dictionaries and a plurality of information models. While conventional systems were only based on one particular standard and may employ one particular dictionary, the present invention provides an efficient and robust terminology management independent of any standard. Thus, the semantic backbone 100 may be employed by any computer system independent of the underlying standard for healthcare data communication and storage. In its simplest implementation, the semantic backbone 100 comprises only one information model and one terminology repository. Nevertheless, the advantage of the present invention lies in the mapping and translation capabilities and the employment of a plurality of information models, the terminology repository 121, and the rules repository 131.

In other words, different organizations or different individuals within organizations invariably use different codes and coding schemes to represent the same "real world" concepts. In order to provide computational semantic interoperability (CSI) for pharmacovigilance, it is necessary to identify and resolve such differences. The present invention provides, for example, the concept resolution service 136 within the rules management component 130. This concept resolution service 136 provides the ability for applications and services to query a terminology repository using core functionality of, for example, common terminology services to retrieve the appropriate data needed to resolve similarities and differences between representations of similar or related concepts. Further, the concept resolution service 136 provides the capability to search information model repositories to identify instances of stored information graphs that contain specific or related concept representations.

The implementation of the concept resolution service 136 contains a number of algorithmic query mechanisms and ontological-based reasoners to identify and discover implicit relationships between concepts and between stored business data that include those concepts. The reasoning process may also include a learning capability to persist implied relationships so that future queries can be resolved with increased efficiency.

Further, the rules repository 131 may, in accordance with a preferred embodiment of the present invention, include rules of types, such as cross-validation, mapping, notifications (alerts, additional information requests, etc.), complex model constraints, etc. The rules repository 131 also provides for execution of pre-defined rules, provides reasoning capabilities, such as concept resolution (Terminfo) or foundation for analytics.

As an example only, a user of a computer system may be interested in a particular medication for a disease. The used computer system will then couple to the semantic backbone 100, for example, via interface 140. Such an interface may include public methods of the services described above which the computer system of the user is made aware of. Further, the above described services may be web services which can be made available using standard network technologies. The interface 140 is not further specified in this application, since the skilled person will be aware of the plurality of possibilities of implementing an appropriate interface.

Returning to the above example, the user's computer system is usually compliant with one particular standard or information model. The computer system may couple to the information model management component 110, for example via the information model usage service 118. Further systems connecting to the semantic backbone 100 may communicate on the basis of a different standard. The information model management component 110 provides all necessary information models in the information model repository 111 to allow for a correct communication with each of these systems. In another embodiment of the present invention, the ability of communicating with multiple systems compliant with different standards may also be implemented in the interface 140.

After connecting to the semantic backbone 100, the computer system then requests information regarding a specific medication. While the information model management component 110 is aware of the underlying information model (or standard), the terminology management component 120 and the rules management component 130 may be employed to correctly retrieve the requested data item. The rules management component 130 will provide the concepts of multiple producers of the medication, where each concept uses different terminologies with respect to the disease. The terminology management component 120, on the other hand provides for mapping between the different concepts, as well as between the information model management component 110 and the rules management component 130.

While using a plurality of healthcare system standards and organization's medicinal concepts, the user's computer system can be provided with a selection of drugs of multiple producers, which are all related to the disease specified in the request.

In conclusion, while each standard provides different information models, the present invention provides a universal interface for a plurality of information models, i.e. data communication and storage standards, and a plurality of conceptual rules or business rules.

A further aspect of the present invention relates to a medicinal product management service (MPMS). This MPMS may be instantiated and maintained by the terminology management component 120. In detail, managing information on organization's medicinal products is at the heart of any pharmacovigilance operation. Basic information on medicinal products may be managed using common terminology services. However, for an organization's own products, there is a significant amount of additional processing and information that is necessary to manage them as "products". Examples include managing marketing authorizations, core data sheets, a history of known adverse events (AE) associated with a given product, etc. None of these collections of data are effectively managed by conventional terminology services. In addition, "pre-marketing" products, e.g. during clinical trials, usually do not even appear in any of the standard terminologies.

The MPMS will provide a core set of operations for managing and retrieving information associated with medicinal products. The service will interact with an underlying terminology service to ensure consistency, which may require an orchestration or choreography capabilities.

A particular service may include a medicinal product query interface which itself may include the identification items sourced from terminologies, but the update of those items would need to be controlled to ensure that data integrity is not compromised. The service may provide functionality for creating and maintaining temporary identification information for pre-marketing products directly through one of two strategies. Firstly, direct maintenance via the MPMS itself may be employed with the assurance of underlying source terminology stability. Secondly, the terminology identification information may be created and maintained using an internal terminology maintenance interface. In both cases there will be a need to replace the temporary values as and when the product is included in the "official" terminology.

In addition, to support adverse event processing for clinical trials, products may need to be identified down to the instance level, e.g. lot or vial number. The MPMS may support this functionality, if required.

It is the terminology management component 120, which provides this medicinal product management service. As an example, the terminology repository 121 may further include terminology data with respect to a particular product. The terms used and stored for the particular product may be part of a standardized dictionary. However, these standardized dictionaries, as described above, may not take into account that a product differs from country to country and with respect to its composition of ingredients. On the other hand, one product may be produced by several companies, which provide the product under the same name, but where each company uses different ingredients or a slightly modified composition than another company.

The present invention provides all such varieties of products within the terminology repository. In addition, the business rules repository 131 may also comprise a concept with respect to a particular product and/or with respect to a particular producer of such product.

Such a concept specifies the interrelation between the plurality of different products, which are all carried under the same name. The concept may include the path on how to determine the product's name depending on the country or region. The terminology repository on the other hand may provide information regarding the number of different products and countries in which the different products are in stock having the same name.

Figure 5:
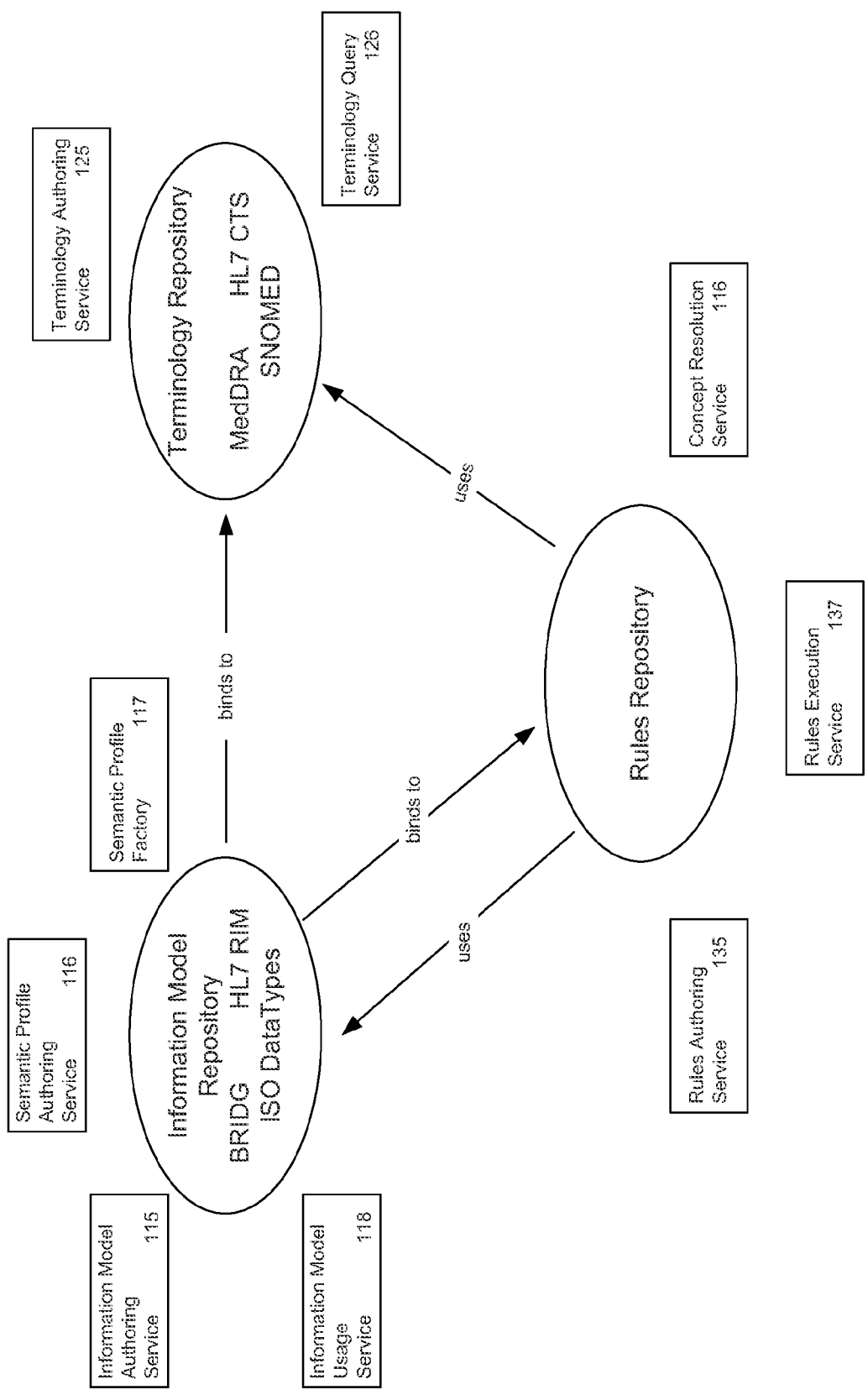
FIG. 5 illustrates the relationship between elements of the semantic backbone of FIG. 4 in accordance with an embodiment of the present invention.

Referring to FIG. 5, the interrelation of the three repositories, information model repository, terminology repository and business rules repository is depicted. As apparent from FIG. 5, the information model repository binds to the business rules repository and the terminology repository. Such binding may be implemented by a service of the information model management component requesting event notifications of services of the terminology management component and/or the rules management component. Thus, the services of the business rules repository and the terminology repository may, for example, register the service of the information model management component as a "listener" of events. In case such an event is triggered, the respective component will notify the ("listening",) registered service of the information model management component 110. As a consequence, the service triggering the event may communicate information to the registered service. On the other hand, the registered service may execute a sequence of methods in response to the event notification.

Figure 6:
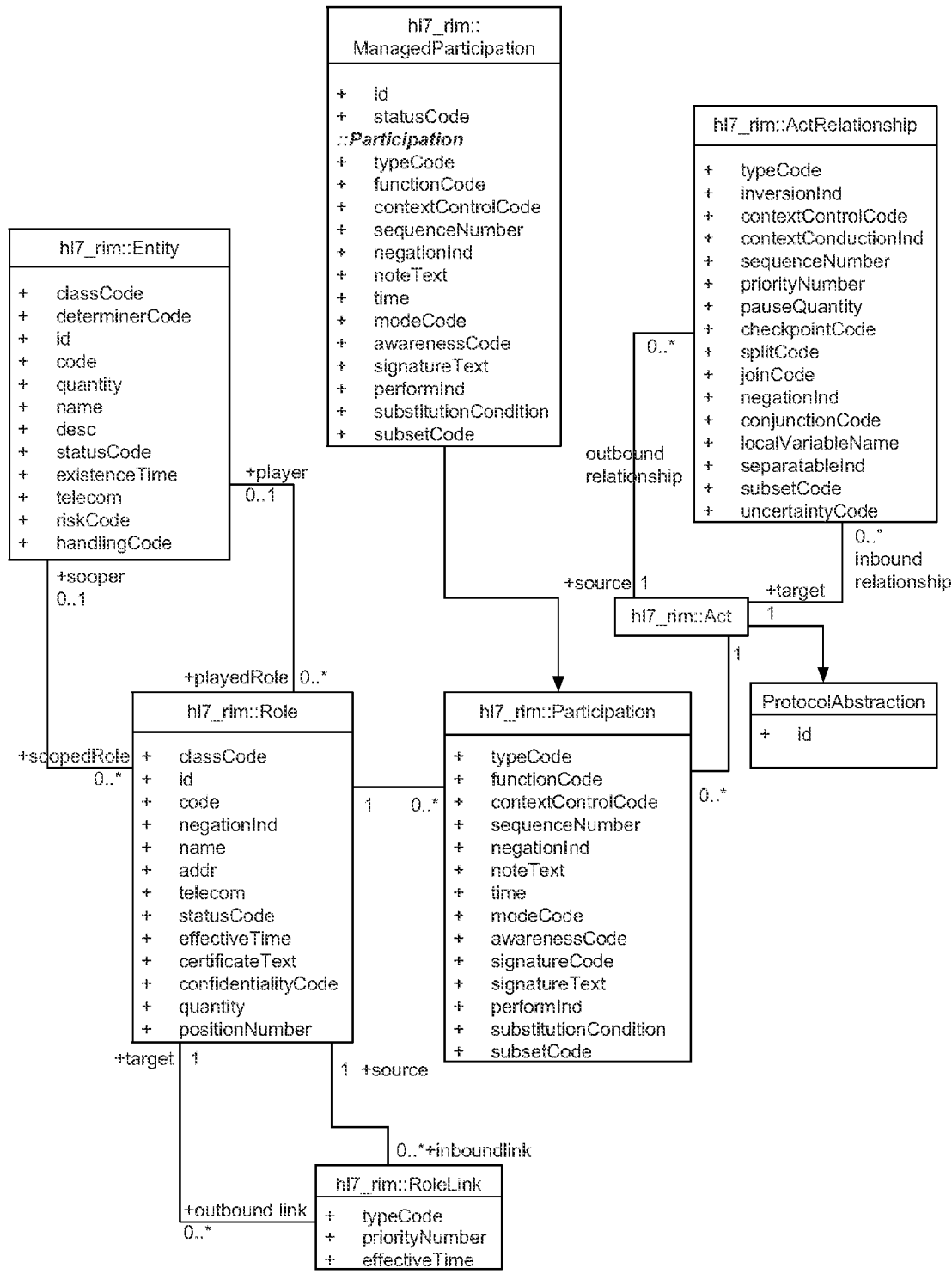
FIG. 6 depicts the HL7 Core RIM Information Model according to an embodiment of the present invention.
Figure 7A:
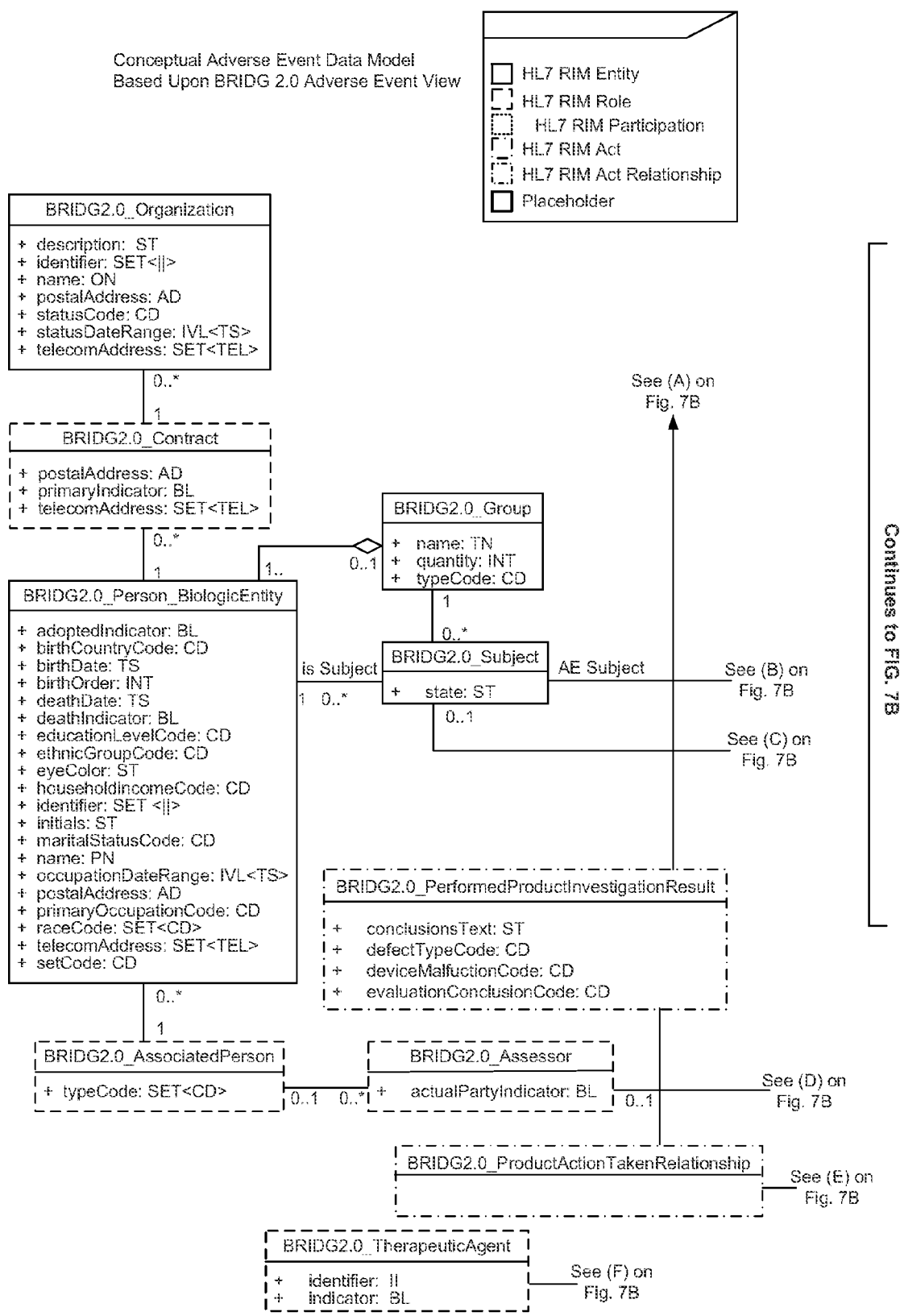
FIG. 7 depicts a common model across domain of BRIDG 2.0 according to an embodiment of the present invention.
Figure 7B:
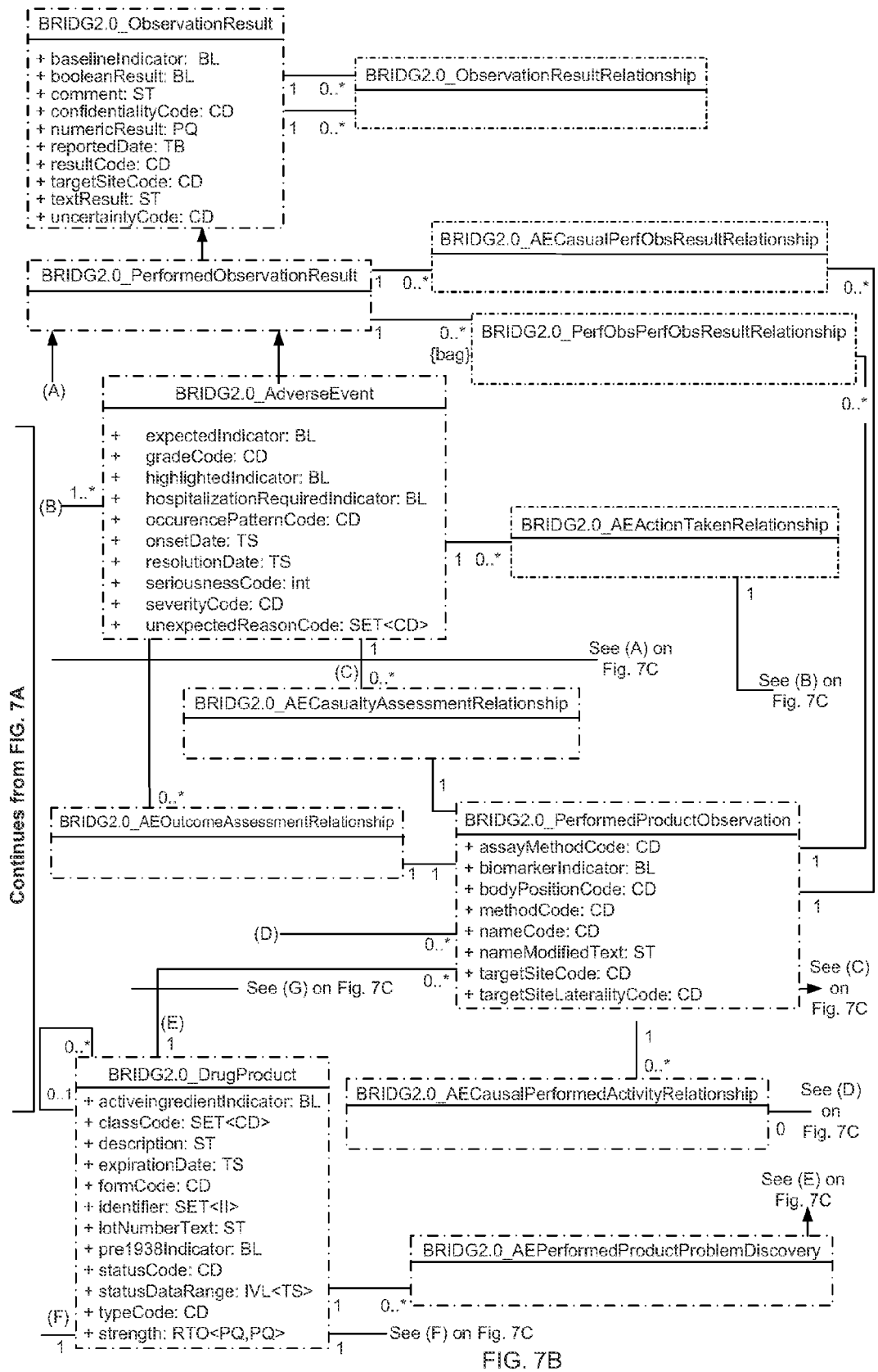
Figure 7C:
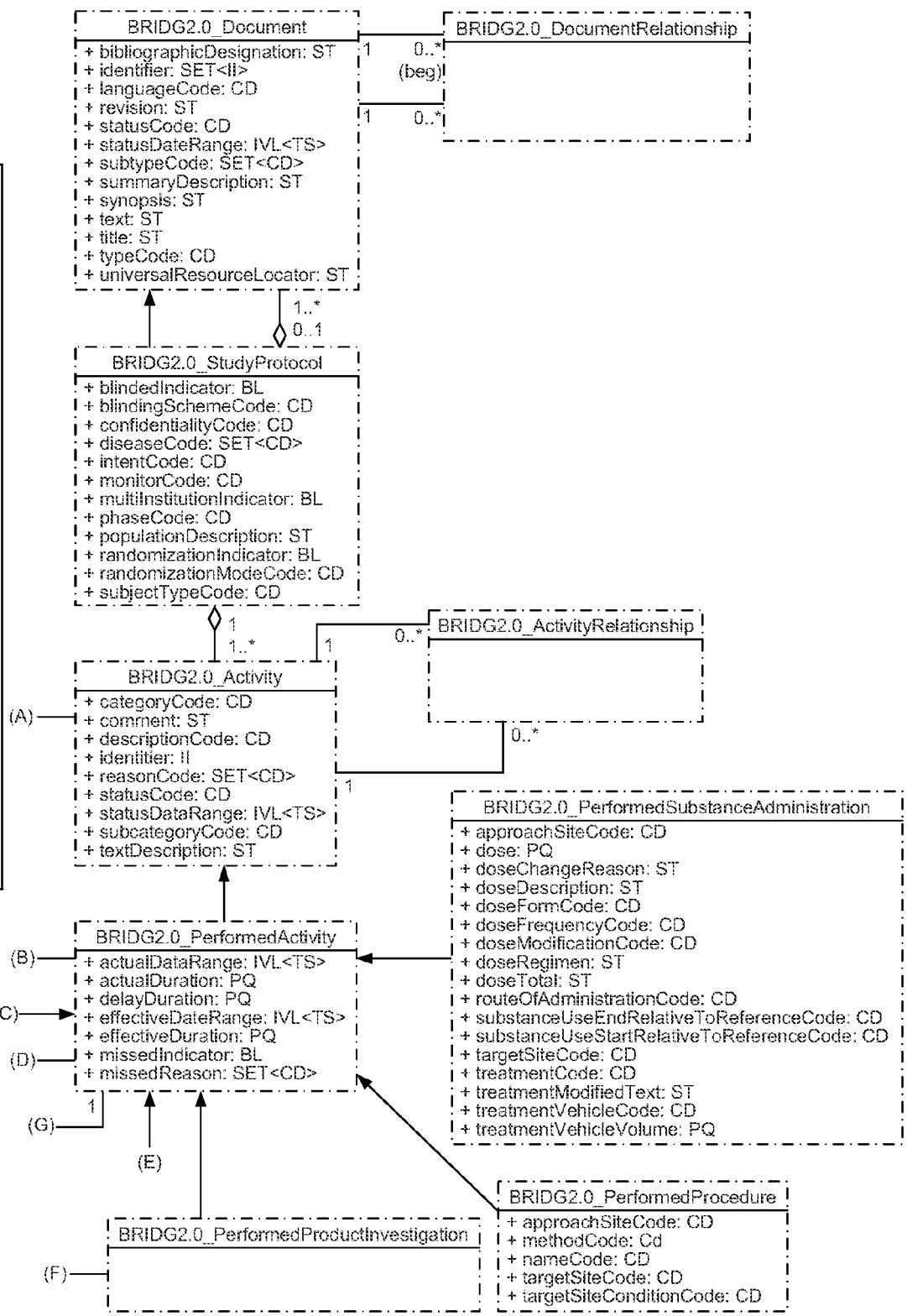
Figure 8A:
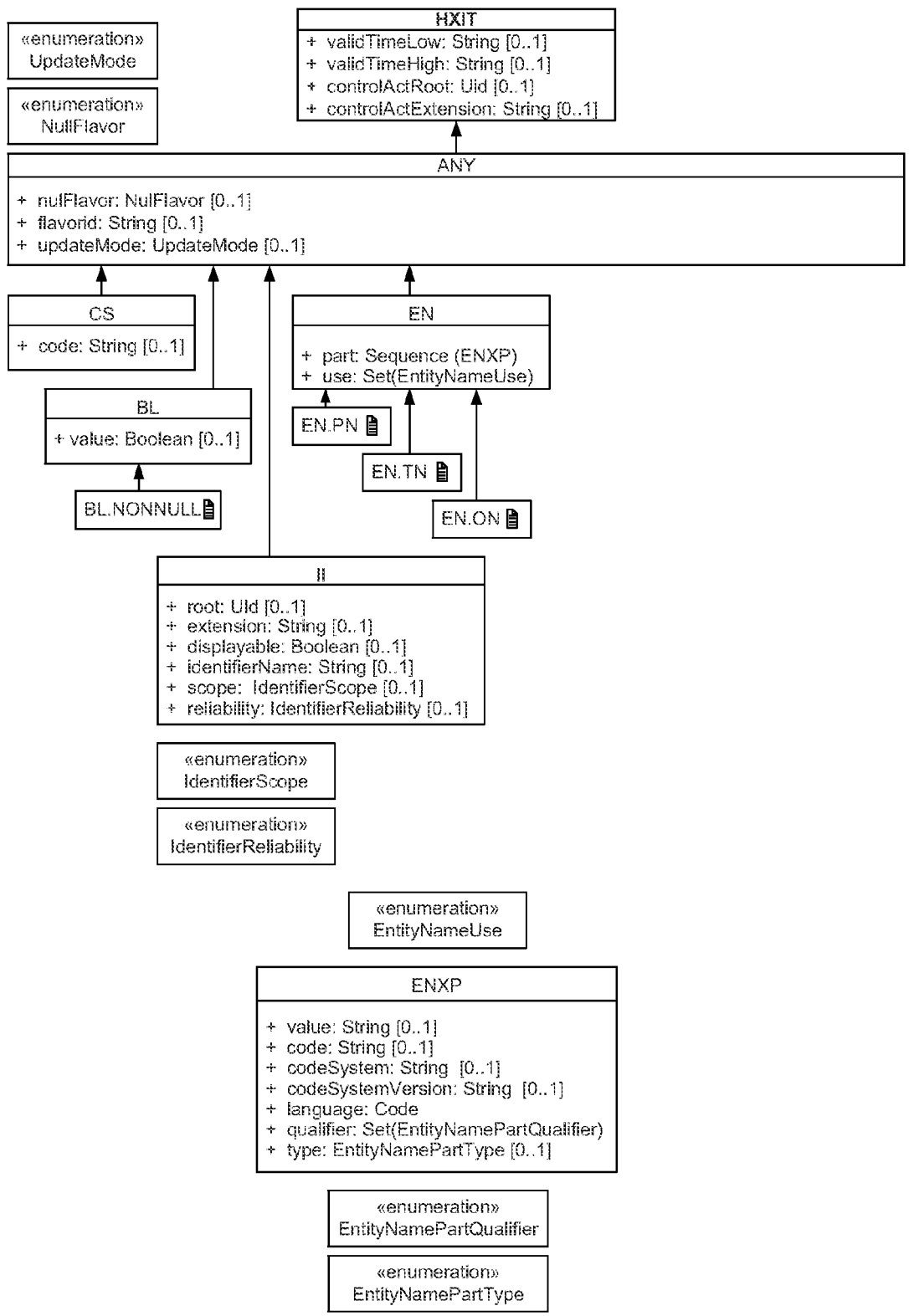
FIG. 8 depicts common ISO Healthcare data types according to an embodiment of the present invention.
Figure 8B:
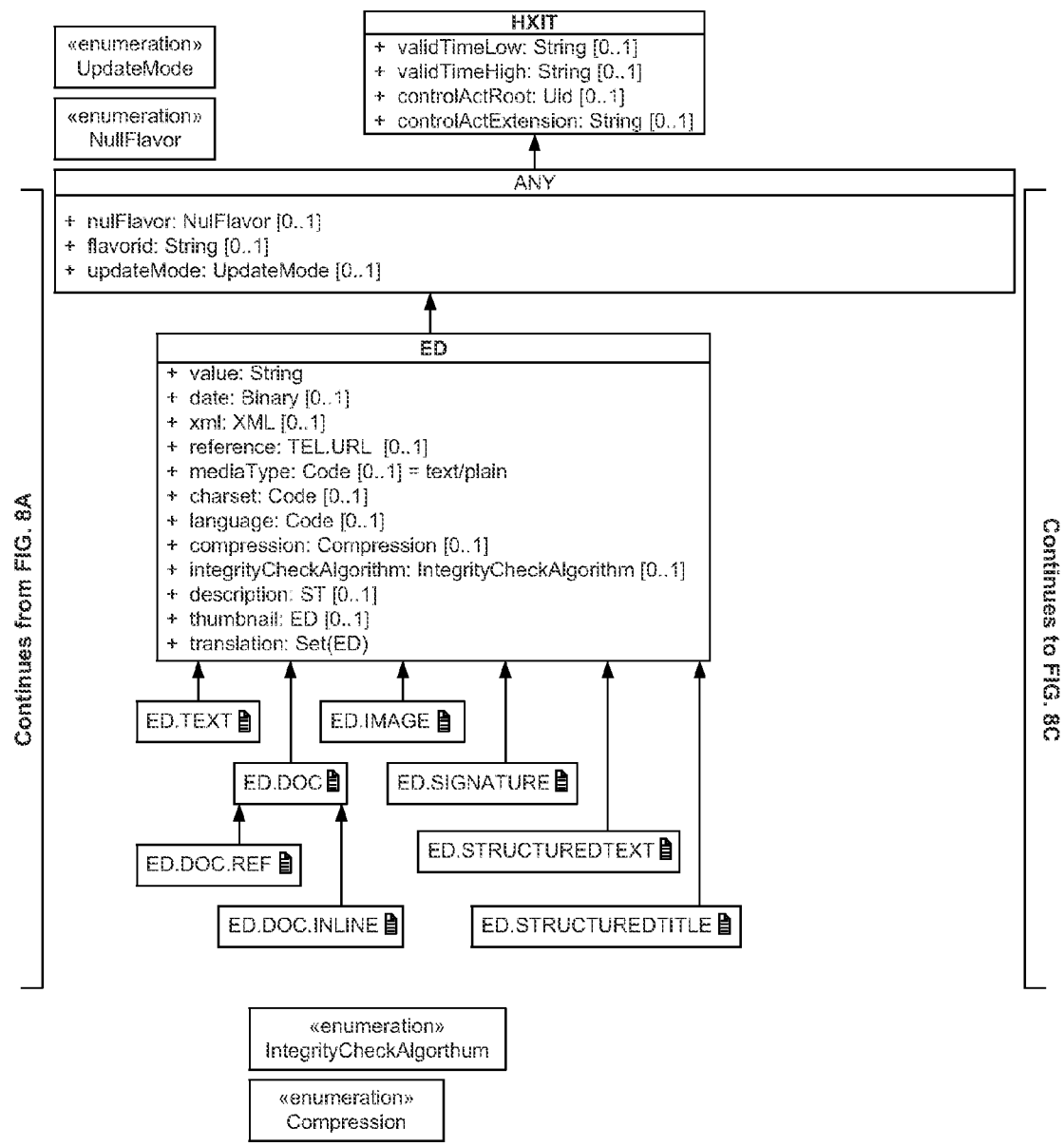
Figure 8C:
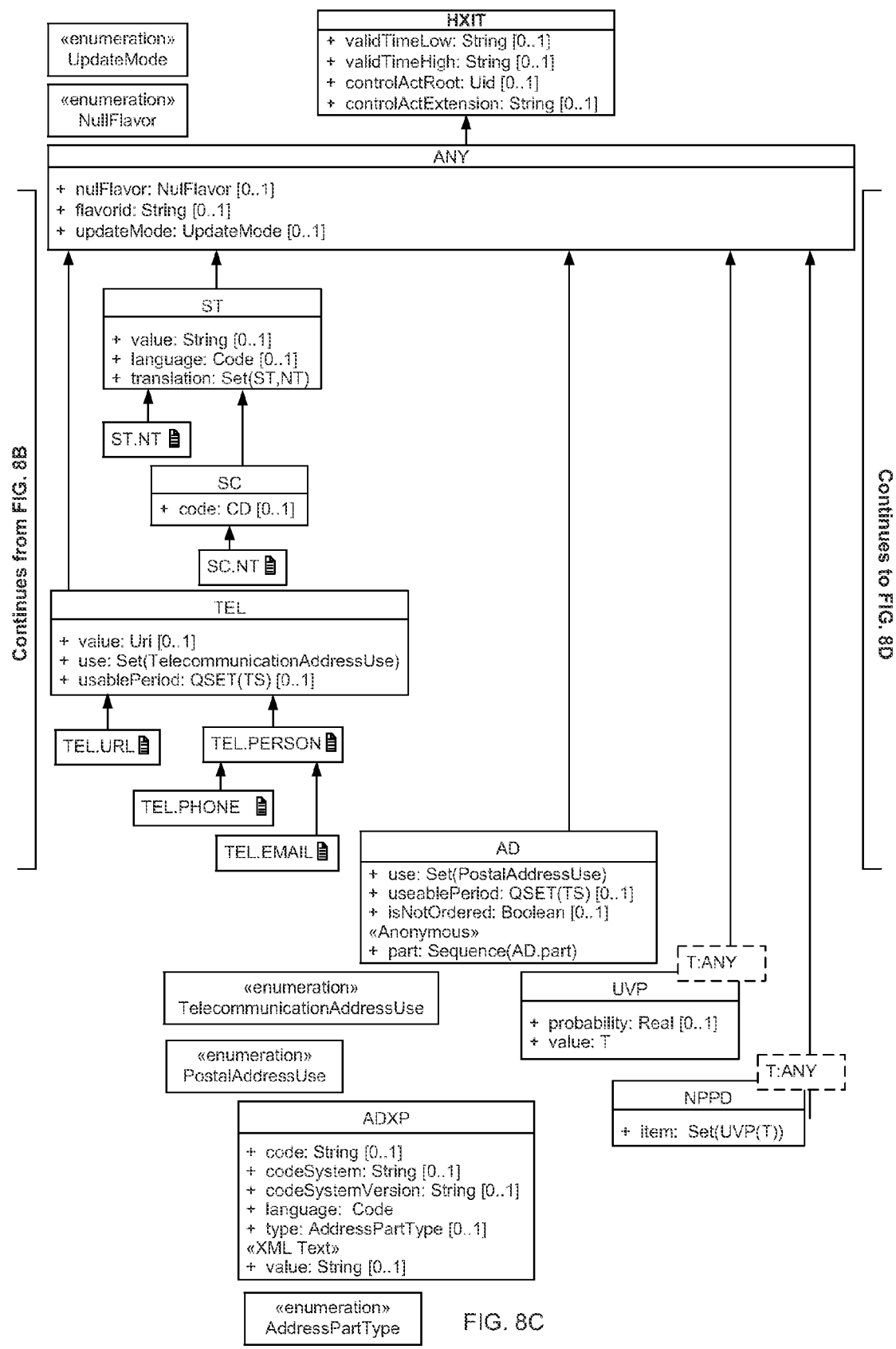
Figure 8D:
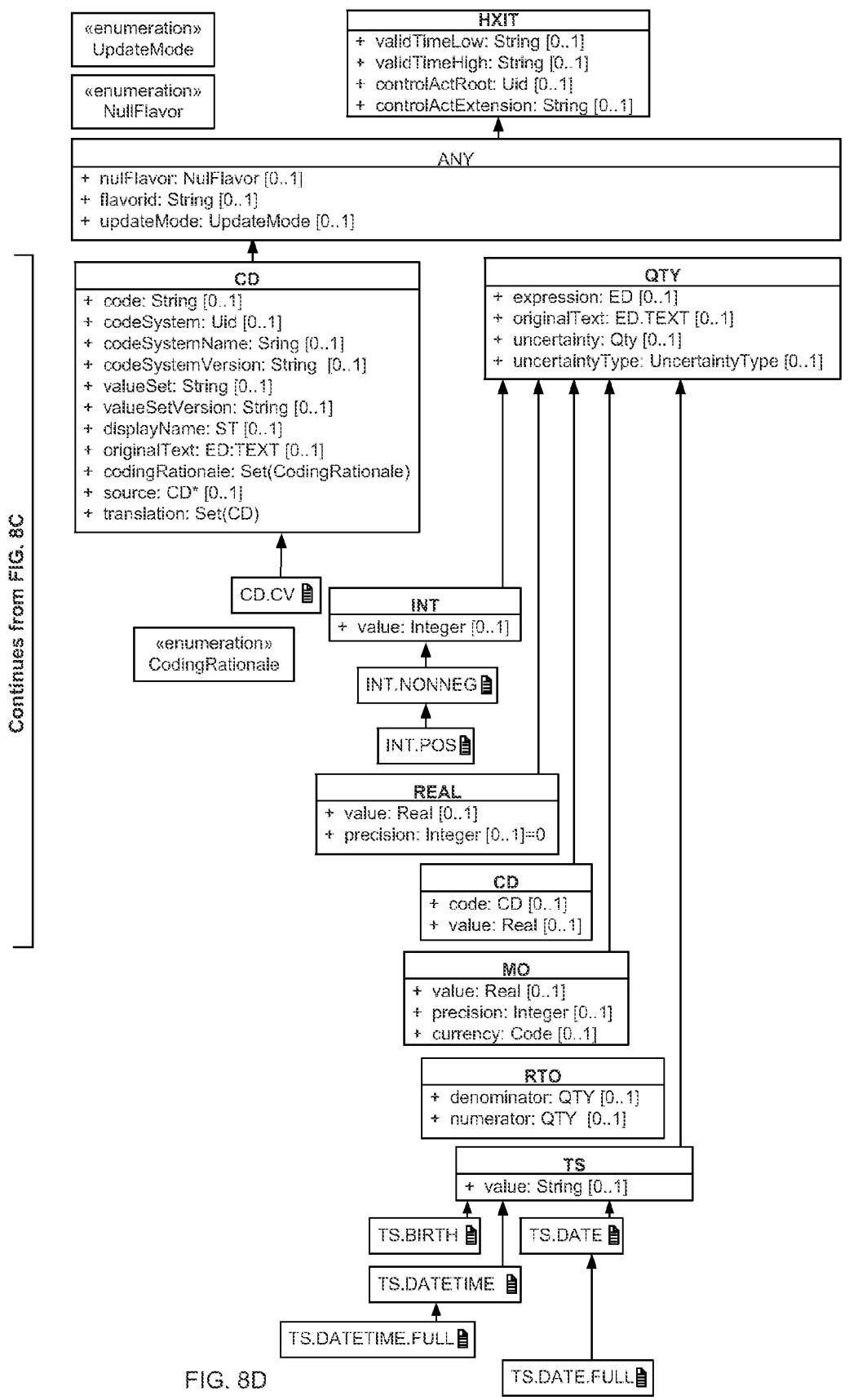
Figure 8E:
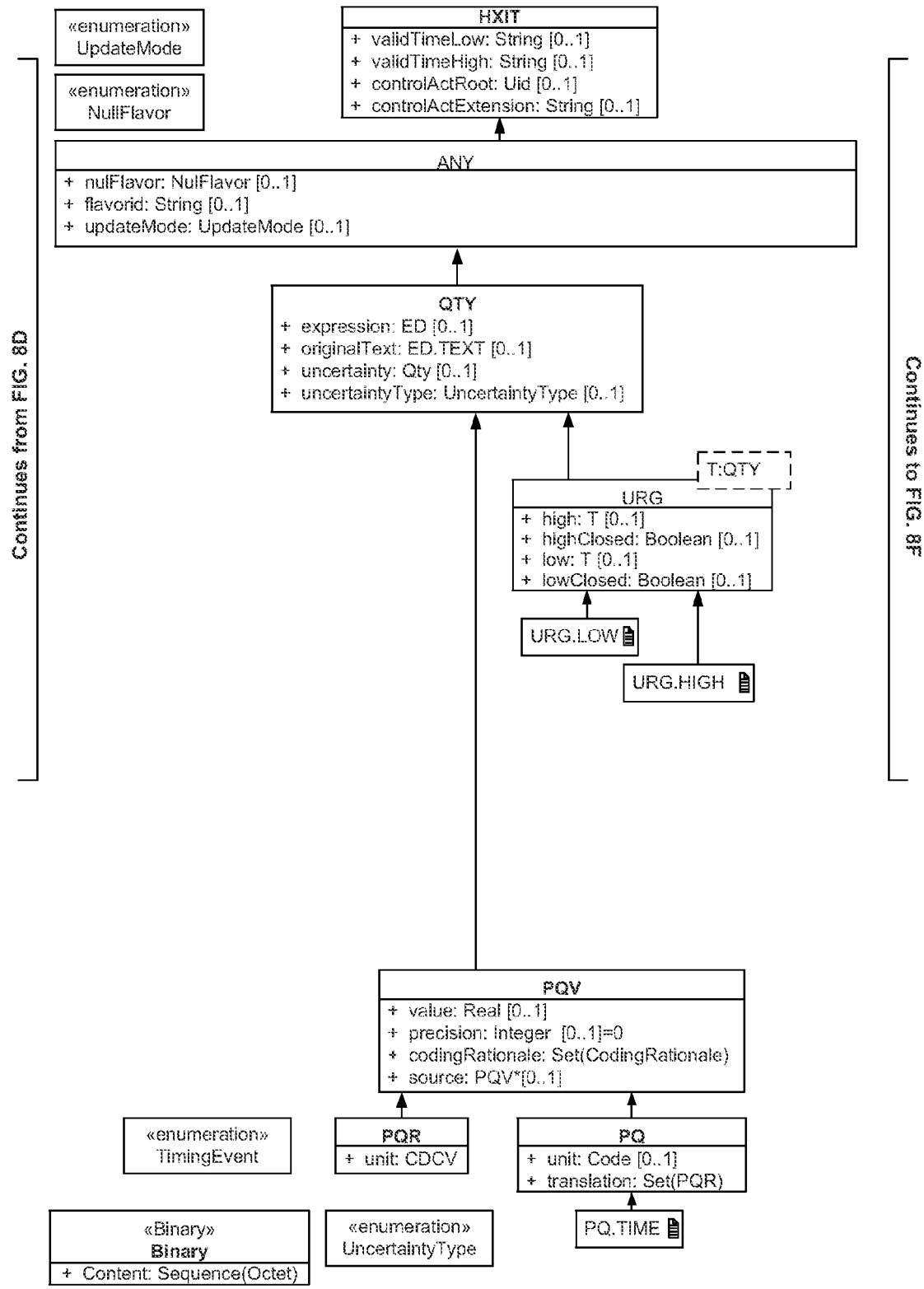
Figure 8F:
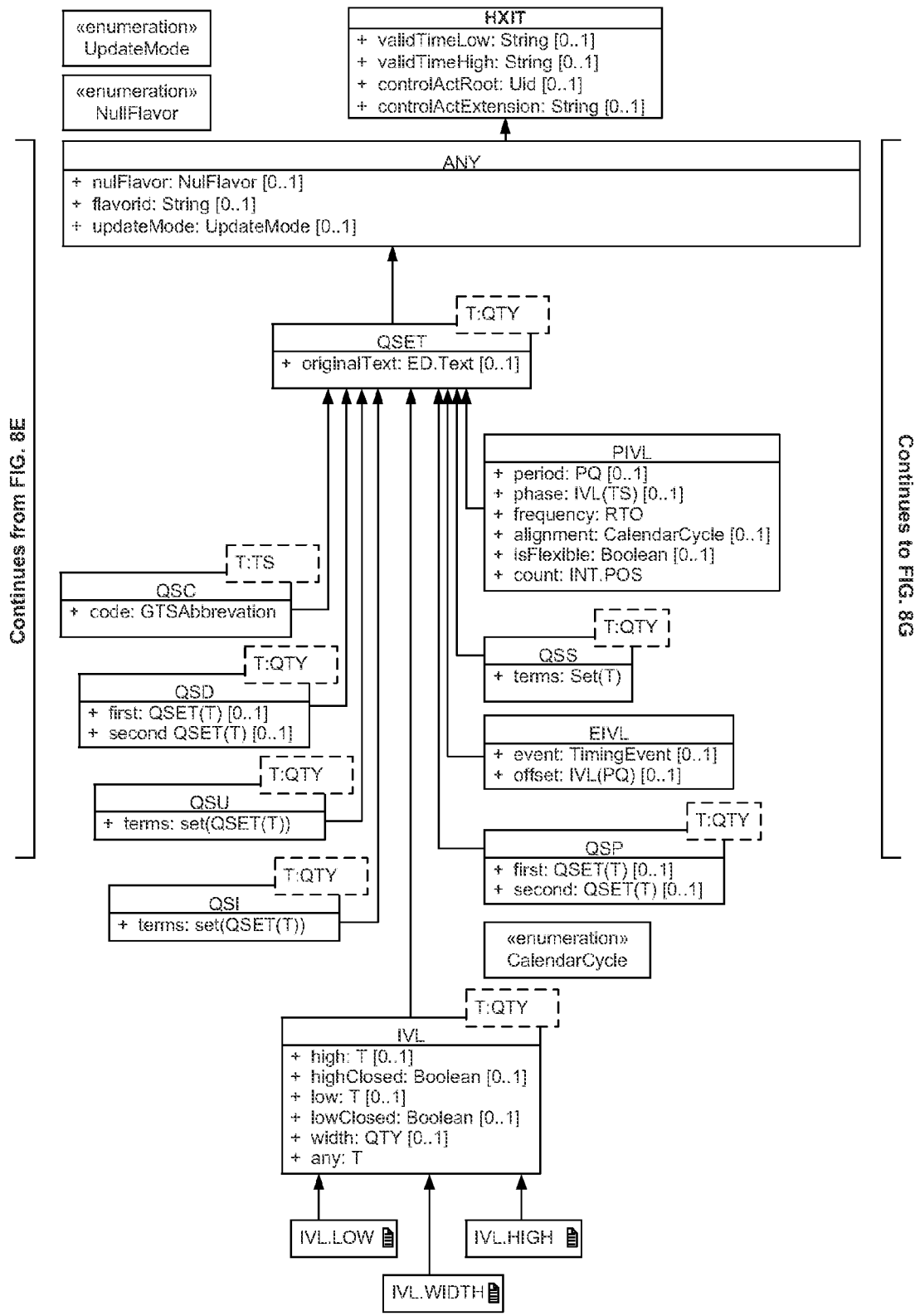
Figure 8G:
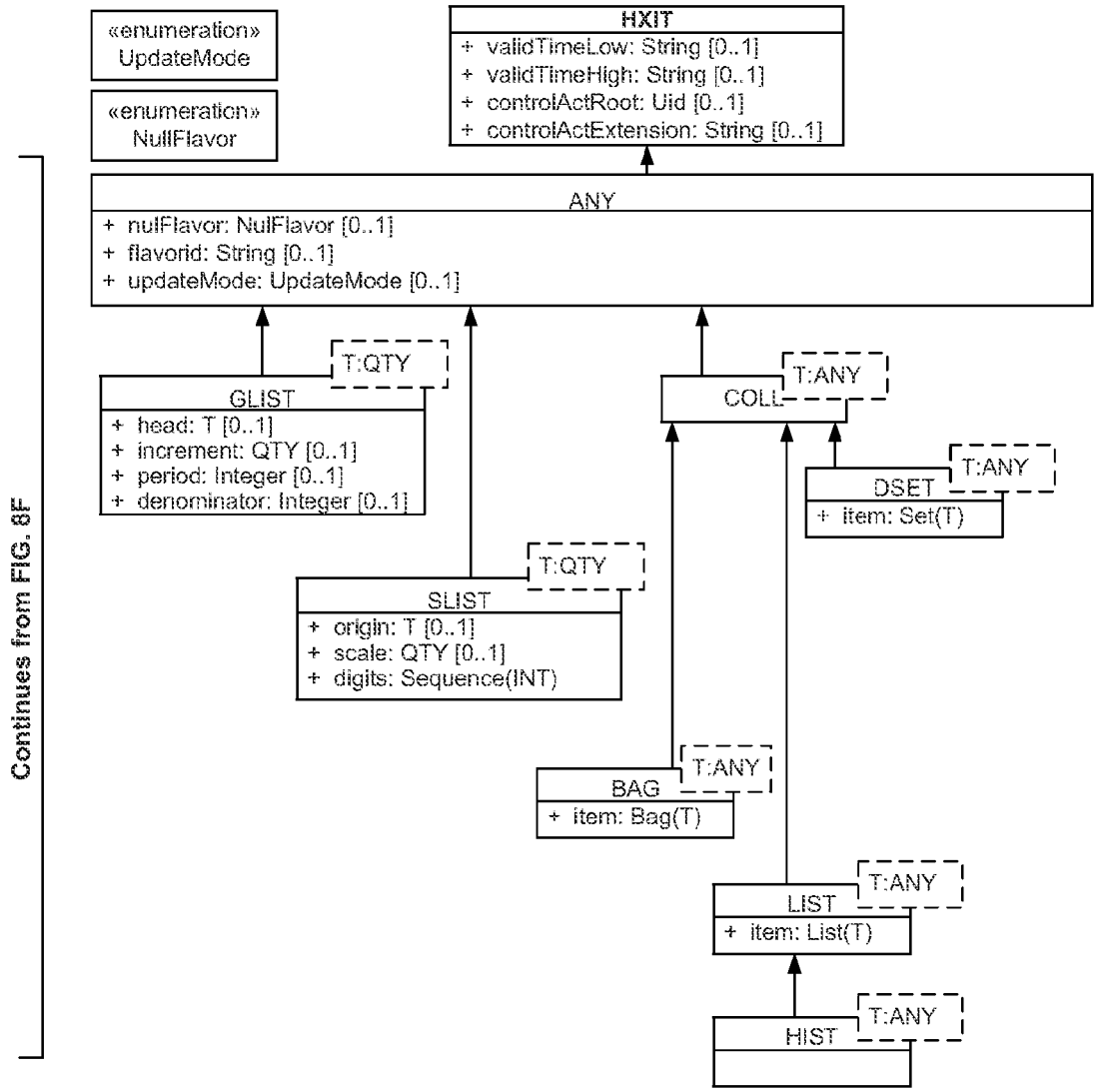

Again with respect to FIG. 5, the business rules repository uses the services of the information model management component and the terminology management component. The use of these services may also involve employing the information model repository and/or the terminology repository. For example, the business rules repository or a service of the rules management component may employ a method of the terminology query service 126 to retrieve particular information from the terminology repository. Turning now to FIG. 6, a common model across domains is depicted. The exemplary model shows an HL7 Core RIM Information Model. FIG. 7 on the other hand shows a common model in terms of the BRIDG 2.0 standard, while FIG. 8 illustrates the relationship and structure of common data types, such as the ISO Healthcare data types.

Figure 9A:
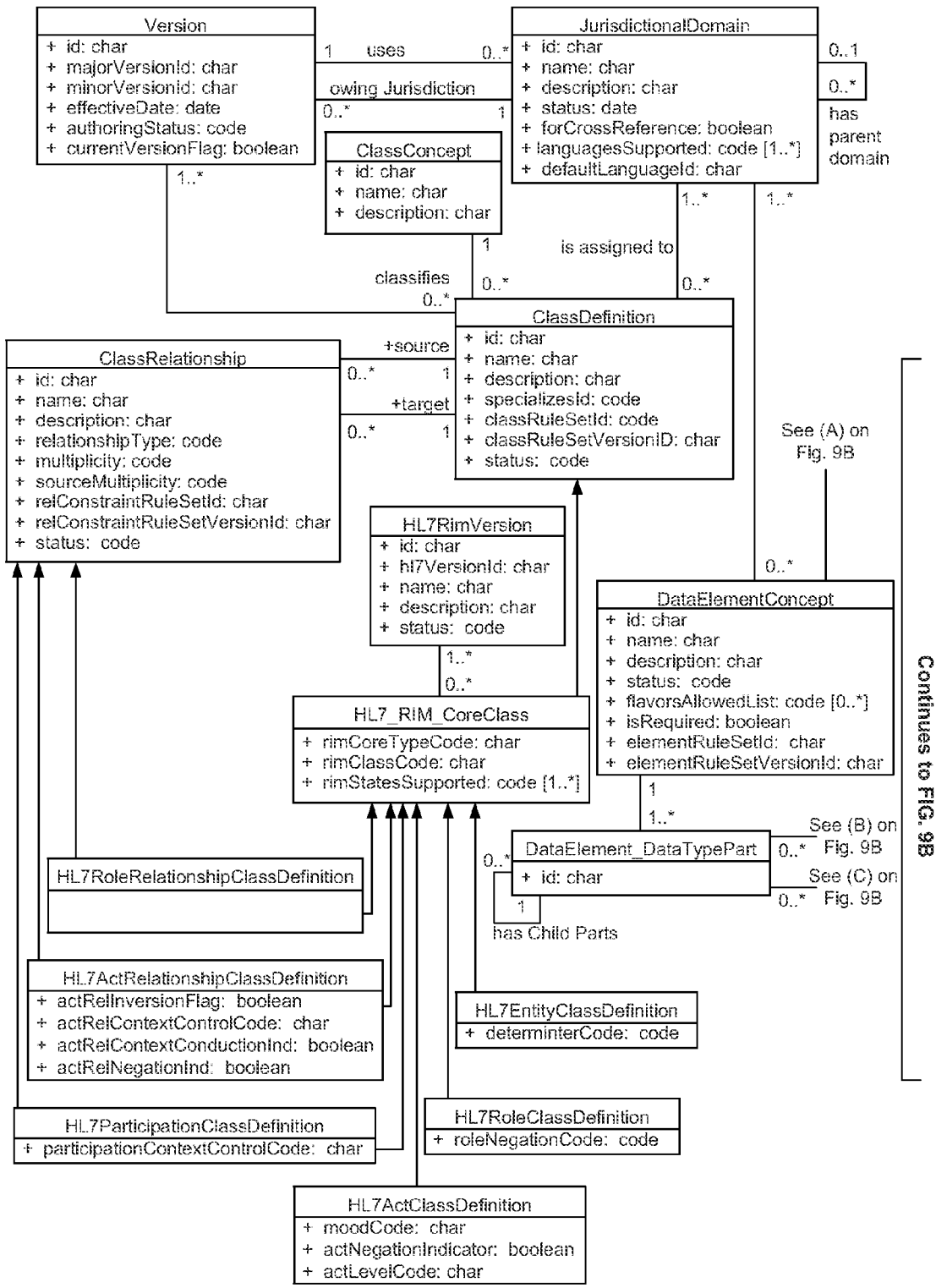
FIG. 9 depicts an information meta model in accordance with an embodiment of the present invention.
Figure 9B:
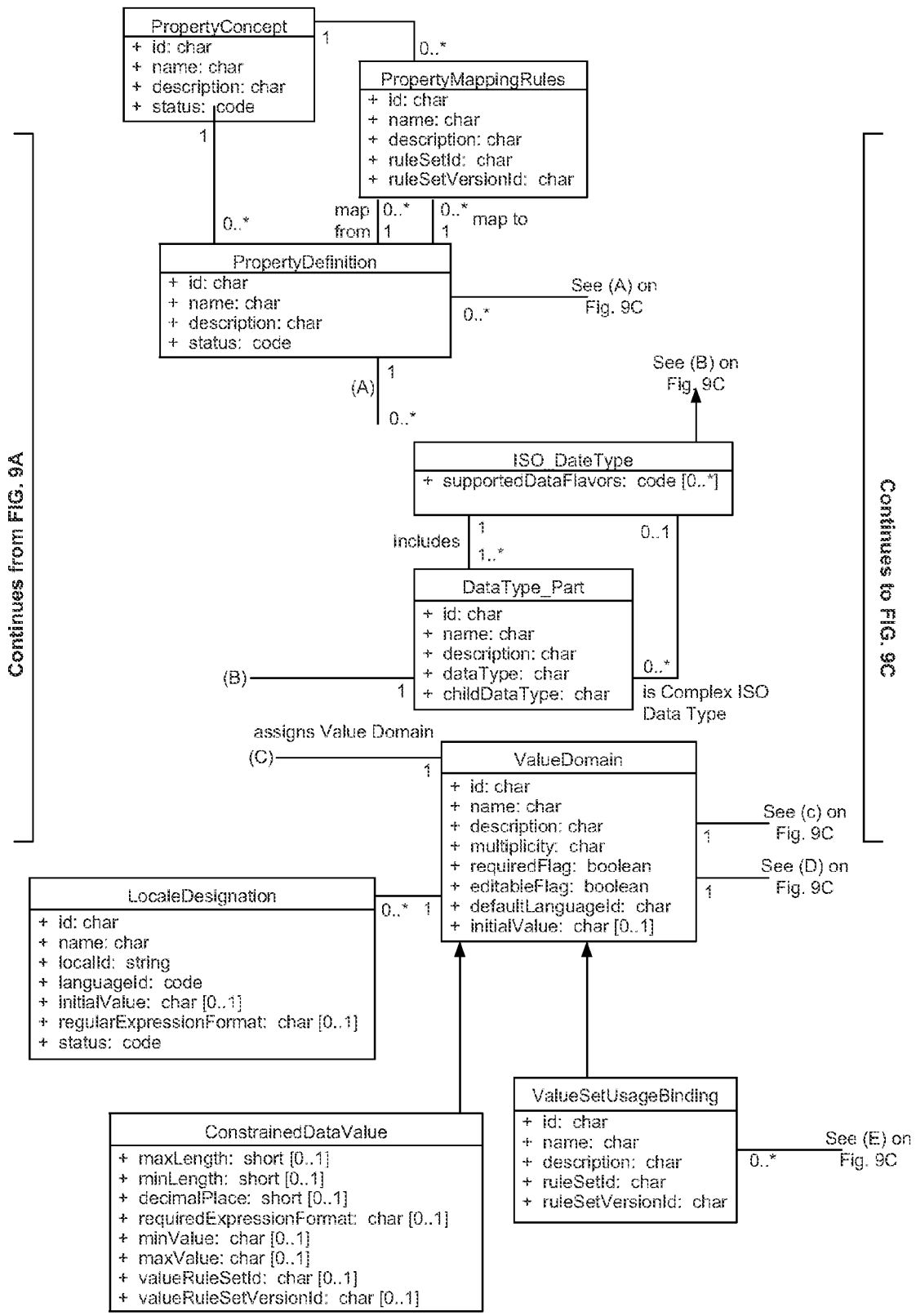
Figure 9C:
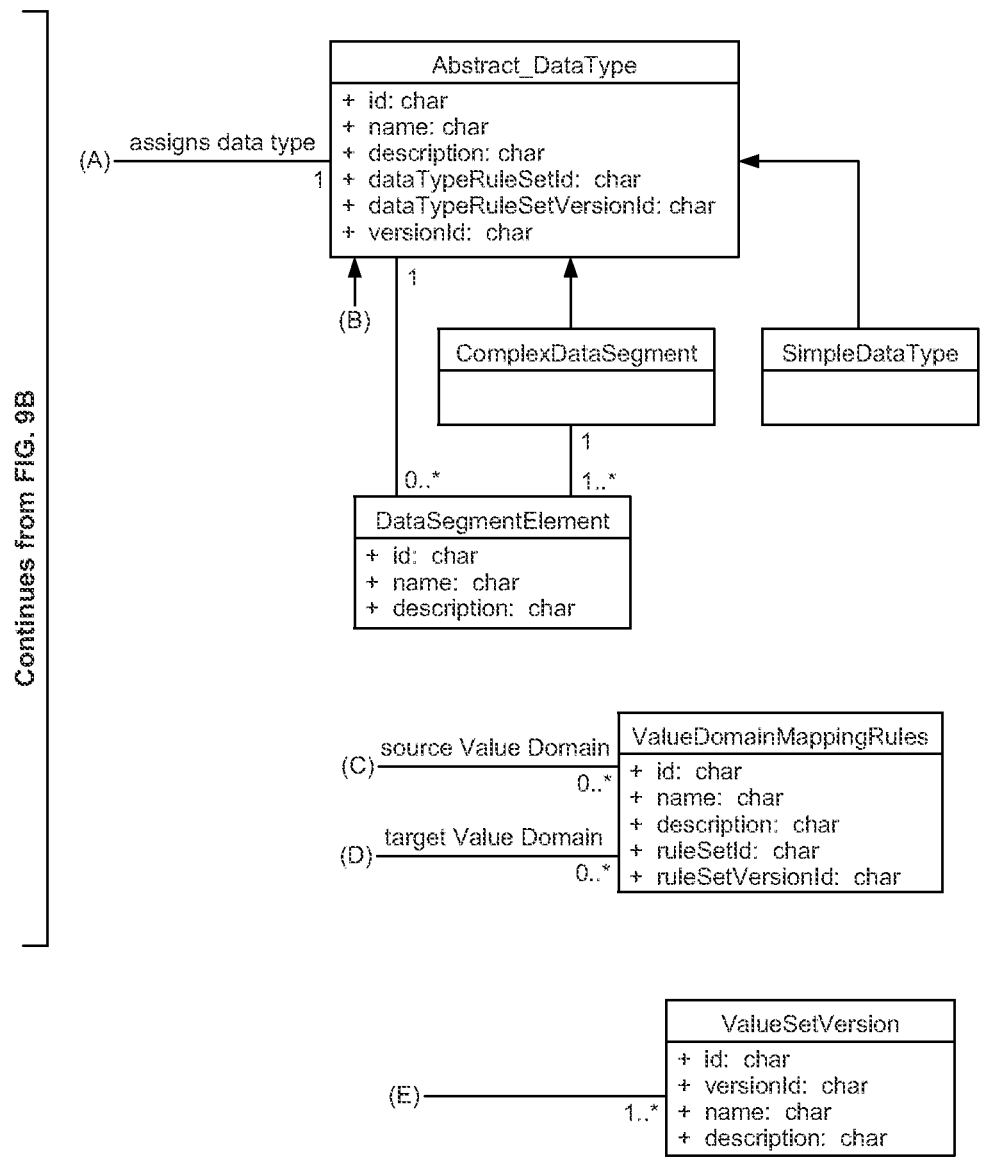

Further, FIG. 9 depicts the data structure of an information Meta model according to a preferred embodiment of the present invention. For instance, a Meta model may be implemented in the information model management component 110 of FIG. 4. It provides capabilities and characteristics, such as versioning, complex data types, domain and usage based value set binding, RIM derived classes and relationships, jurisdictional domain support for ownership and usage. The information Meta model does not represent individual concept instances, e.g. the symptom "headache" would not be represented, but the idea of the "symptom" would be (as an attribute or class). Its purpose is to support dynamic service configuration (semantic profiles) and generic data validation capabilities. It further provides a loose coupling between information model and terminologies/value sets. Thus, a clean separation of ownership can be achieved.

Figure 10:
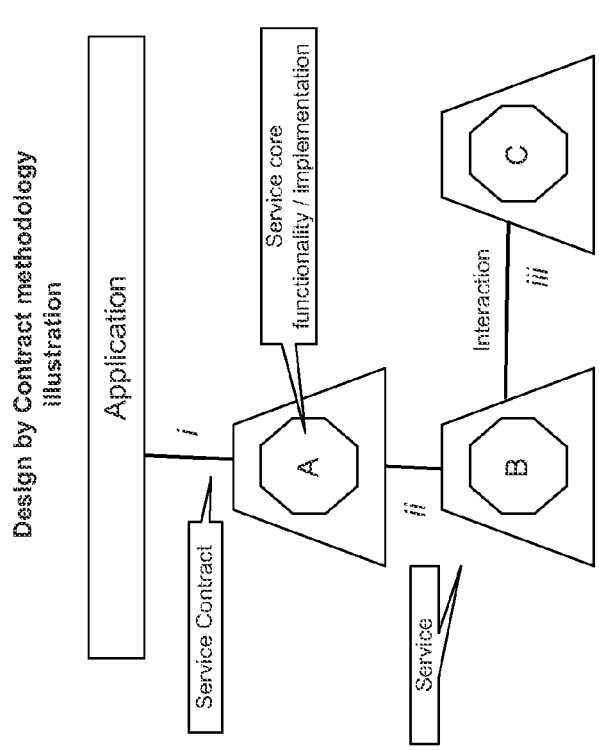
FIG. 10 depicts a data flow model in accordance with an embodiment of the present invention.

Referring now to FIG. 10, according to a preferred embodiment, the platform of the present invention is being built with predictable data flows using a so-called design-by-contract approach. Design by contract is a software construction methodology which ensures the reliable and predictable flow of data through a system, i.e. predictable system behavior. Its major paradigm is the idea that elements of a software system ("services") collaborate with each other as consumers and providers, on the basis of mutual obligations and benefits. This collaboration is guaranteed by the contract specification which enforces a certain obligation to be guaranteed on entry by any client module that calls it.

For instance, an obligation may include the routine's precondition, an obligation for the client, and a benefit for the supplier (the routine itself), as it frees it from having to handle cases outside of the precondition. The contract specification also enforces a certain property on exit, such as the routine's postcondition, an obligation for the supplier, and obviously a benefit for the client. Finally, the contract specification maintains a certain property, assumed on entry and guaranteed on exit, such as the class invariant ensuring that a predicate do not get changed to a form no allowed by the class. In addition, services build according to this method can be assembled to an Enterprise Architecture, while the implementation of the service is hidden from the rest of the system. In conclusion, the service specifications and the model describing how they dynamically interact, makes up the Enterprise Architecture design.

Figure 11:
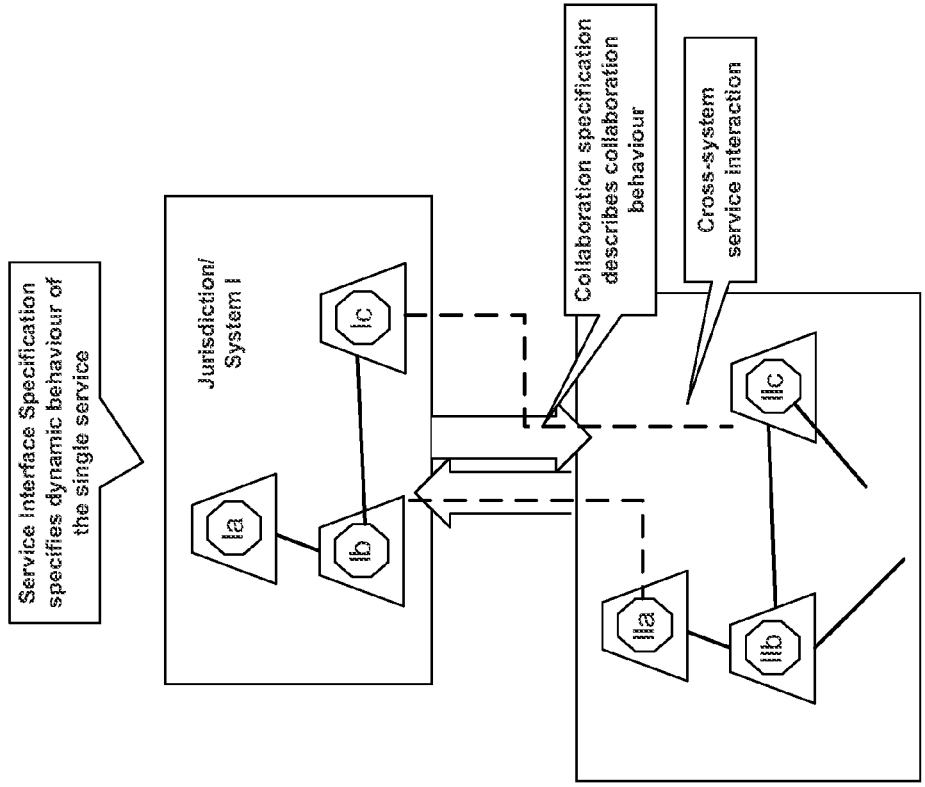
FIG. 11 illustrates a model for collaboration of distributed systems in accordance with an embodiment of the present invention.

FIG. 11 illustrates an embodiment of the present invention. A behavioural framework that forms the basis for collaboration in bigger distributed systems like Comprehensive Treatment Service Program (CTSP) is shown. The collaboration of systems is the functional cooperation and coordination of the systems and the exchange of data between them to achieve a business goal, e.g. clinical trial protocol or data exchange. A behavioural framework describes the aspects of dynamic semantics of system interaction and/or system collaboration. For example, these aspects include under which conditions the data flows, the types of parties between which the data is flowing, and interdependencies between separate data flows. Further, other aspects of control flow are those that ensure that data is flowing properly over the course of the interaction and in such a way as to support the business function after which the service specification is derived.

While service contracts define the behaviour of a single service providing functionality in collaboration, the collaboration specification (or service choreography) defines the remainder of the overall behaviours by specifying how individual behaviours (operations) are used, including sequencing and structuring of interactions. The collaboration specification contains a rigorous set of rules defined from a global viewpoint by which peer-to-peer services can interoperate with predictable/deterministic results. The behavioural framework which comprises the service choreography and the service interface specifications is essential to obtain predictable system behaviour and guarantees successful system collaboration.

Figure 12:
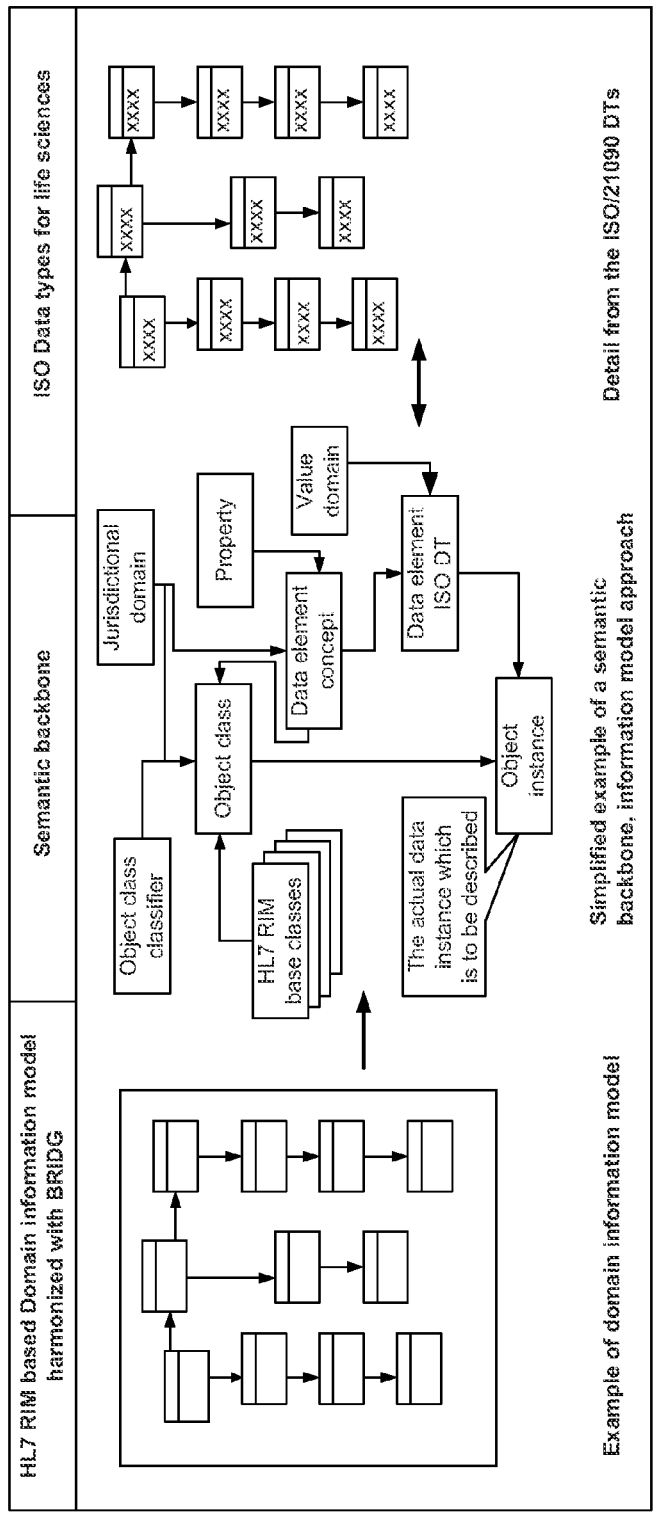
FIG. 12 illustrates the relation of a complementary information model, semantic backbone, and ISO data type layers according to an embodiment of the present invention.

Referring to FIG. 12 which illustrates how static semantics are realized by the complementary information model, semantic backbone, and ISO data type layers. In particular, the example of a domain information model is shown in the left part of FIG. 12. Domain information modeling is based on the standardized RIM—the Reference Information Model of HL7. The class diagram provides a slightly idealized, abstracted representation of the reality of the drug safety domain. Class diagrams provide rich representations of how entities (the classes) interact and relate to each other. In a preferred embodiment of the invention, the model will be harmonized with BRIDG and HL7 RIM compliant. It is to be noted that HL7 is a leading standard development organization for the Lifescience Domain. As will be outlined further below, the ISO DT standard is semantically isomorphic to HL7 Abstract Data Types R2.

Returning to FIG. 12, a simplified example of a semantic backbone according to an exemplary information model approach is shown in the middle of the Figure. In detail, the semantic backbone is used to instantiate ("fill with data") the concepts captured at the lowest level of the information model. It provides the semantic context of the concept by object/property tuples as well as standardized terms from controlled vocabularies. The actual data instantiation is done using ISO DT. The backbone can be build using information models or ontologies (not shown).

According to the right part of FIG. 12, a detail of the ISO/21090 DT is depicted. ISO Data types are classes which unambiguously define the way that concepts, like a clinical observation, must be expressed at the lowest description level. This allows a standardized storage, retrieval and machine processing of the data.

Figure 13:
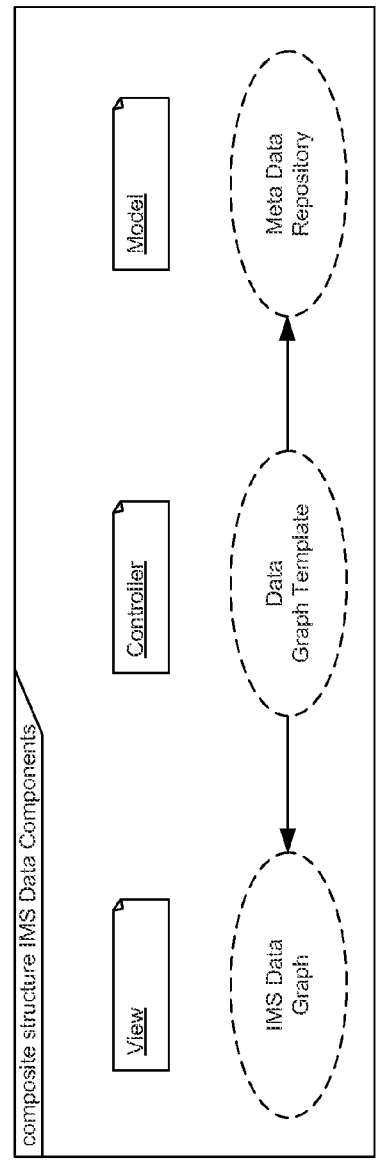
FIG. 13 depicts a composite structure of data components in accordance with an embodiment of the present invention.

With respect to FIG. 13, the core pattern of data components is illustrated according to a preferred embodiment of the present invention. The pattern can be divided into a view, controller and model element. The "view" relates to an Information Management Service (IMS) Data Graph. The IMS Data Graph may have a generic transport object capability, such as capabilities services and/or application tier. Further, the Graph may include validation and constraint rules for use within other services and applications, and may be reusable across all IMS Semantic profiles. The controller relates to a data graph template, which binds Meta Data Repository (MDR) semantics to data graphs, and which provides persistence/OR mapping.

Figure 15A:
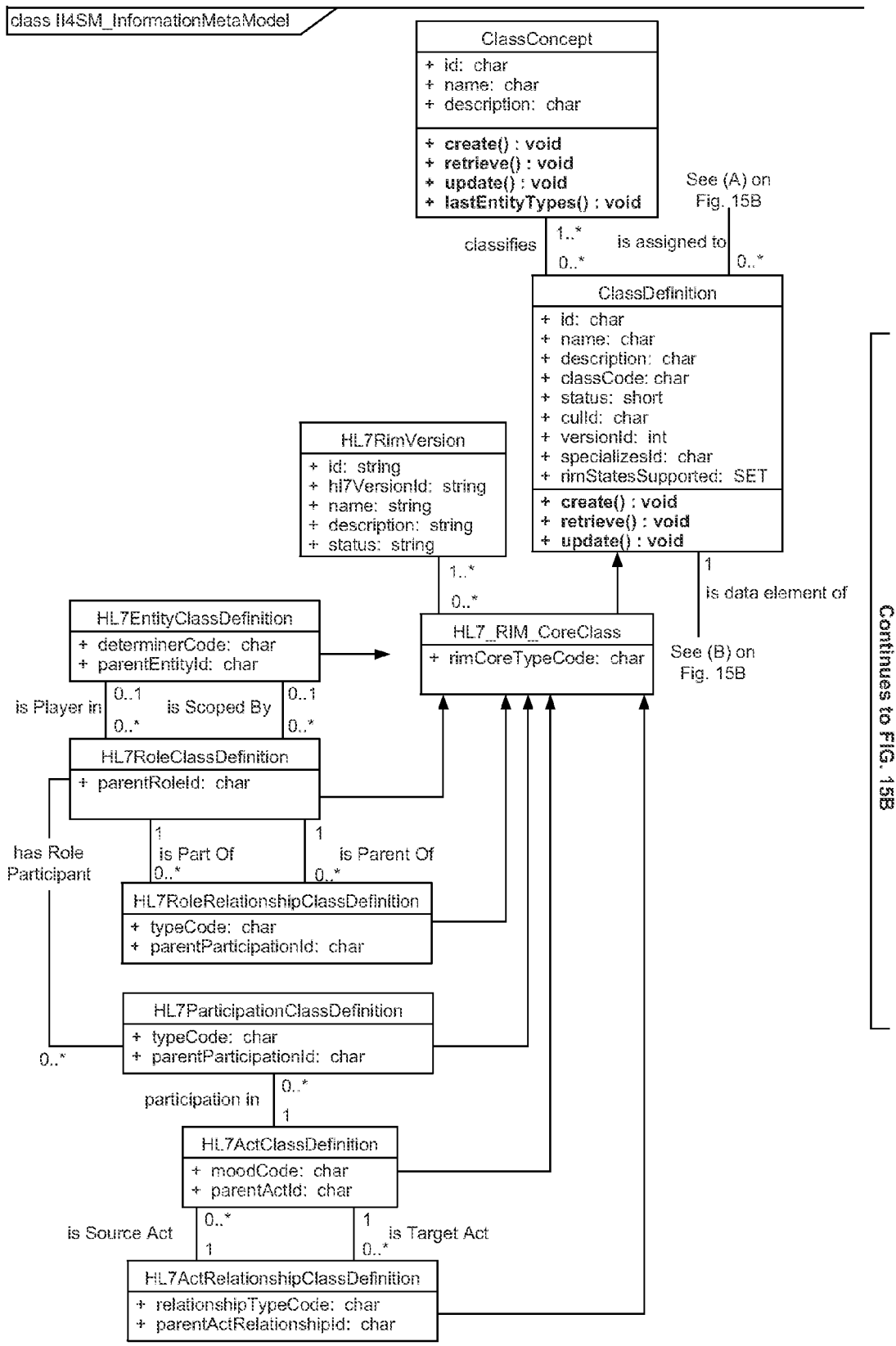
FIG. 15 depicts a model of a meta data repository according to an embodiment of the present invention.
Figure 15B:
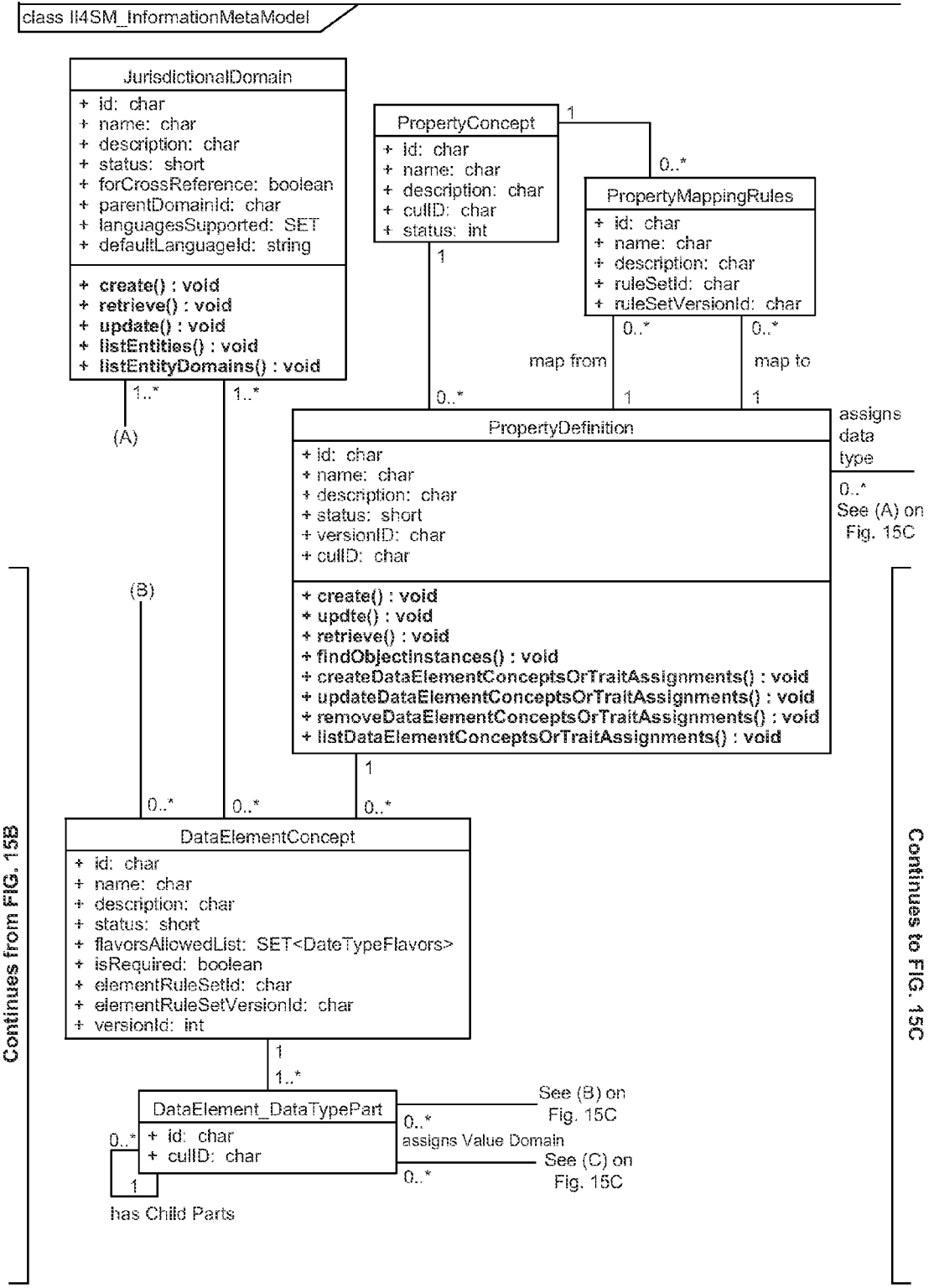
Figure 15C:
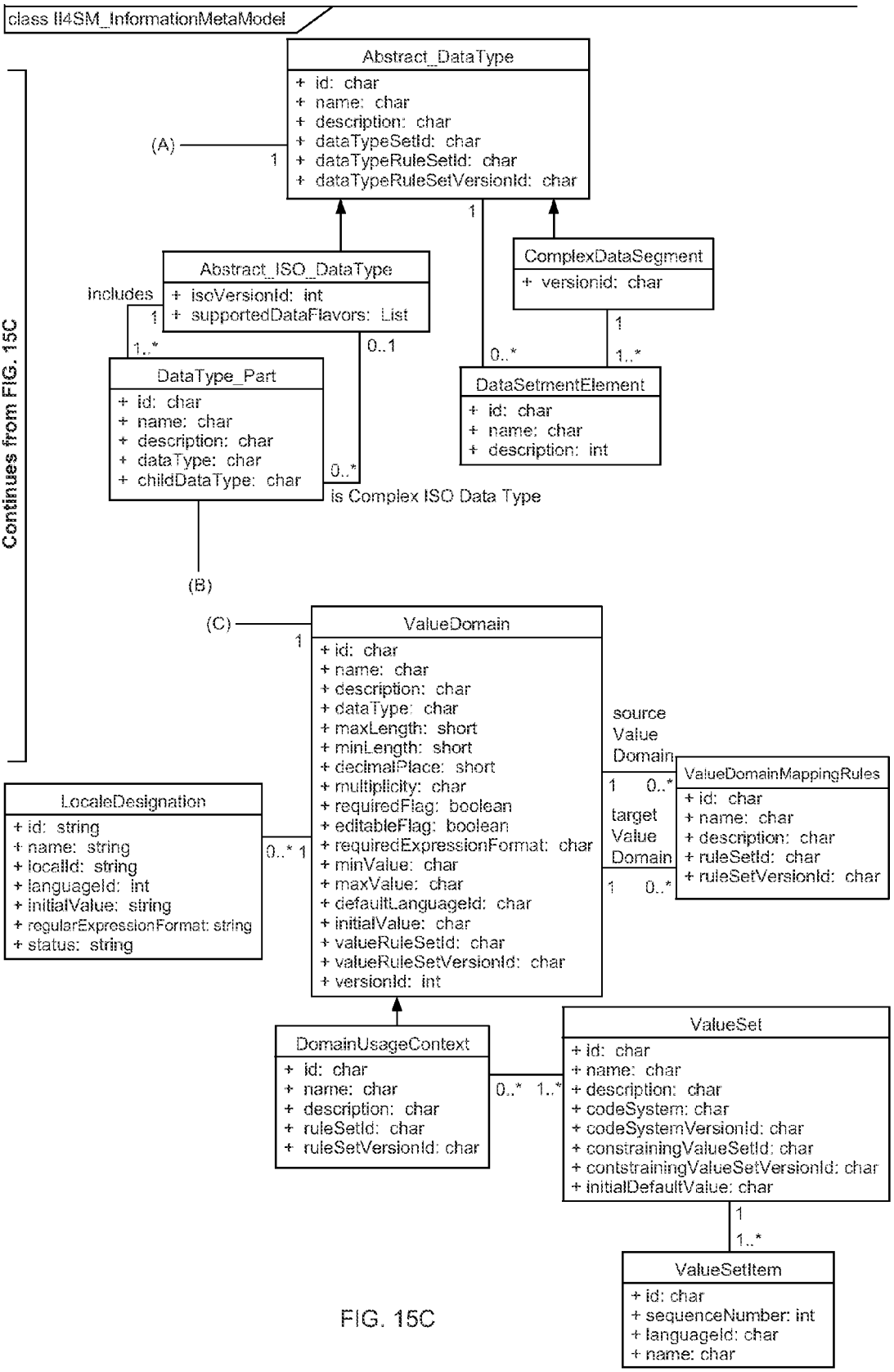

Further, the model relates to a Meta data repository that is depicted in more detail in FIG. 15. The Meta data repository includes a computable semantic interoperable class and attribute definitions, validation and constraint rules, and/or value set bindings.

The Meta data repository relates to the jurisdictional domain that represents the organizational domain context that associated classes and attributes are valid within. Further, the jurisdictional domain is similar in concept to a security domain and identifies the scope of usage of a ClassDefinition and its associated attributes (Data Elements). It may also be organizational or geographical, but does not define its characterization. The jurisdictional domain has an owner which defines policy and manages ClassDefinitions.

The Meta data repository also relates to a Class Concept which represents a specific category or concept of "thing". The Class Concept is a classifier for "thing" which binds similar types of Class Definitions of the same category, and which provides a mapping capability between different representations of Classes which represent the same concept.

The Class Definition represents a specific class definition of "thing" as a container for the Data Element Concepts (attributes). It provides a generalization/specialization hierarchy or class definitions. The Class Definition is bound to HL7 RIM Core Class Types—Entity, Role, Act, Role Relationship, Participation, Act Relationship, and is bound to versions of the HL7 RIM. Finally, it supports a sub-set of the corresponding HL7 RIM Core Class states and allowable state transitions.

The Meta data repository further relates to a Property Concept, which is similar to Class Concept, and represents a specific concept of an attribute which is not bound to a class. The Property Concept is not bound to a particular representation or data type, while it provides a mapping capability between different representations of the same attribute concept.

Further, the Meta data repository relates to a Property Definition that binds a Property Concept to a particular representation (data type). This binding allows the definition of allowable "data flavors" within the above mentioned Data Element Concept. The Data Element Concept represents the binding of a particular Property Definition to a Class Definition as a named Data Element. It contains over-rides that provide for differing control attributes per Jurisdictional Domains (i.e. required/not required), and over-rides that provide for differing value domain bindings (i.e. Value Set, language, etc.). The Data Element Concept also defines allowable "Data Flavors" for bound ISO Data type and provides Constraint Rules processing for Data Element.

The Meta data repository also relates to an item Data Type Part, which represents a component part of the Data Element complex ISO Data type. The Data Type Part associates a Value Domain for the Data Type Part, and may be a part list and hierarchy specific to an ISO Data Type.

In addition, the meta data repository relates to Domain Usage Context, Value Sets and Value Items. This specializes Value Domain for Coded Values and Terminology Value Set bindings, and encapsulates Rules around determining which Value Set to use (Value Set hierarchies, language designations, etc.). For instance, Value Sets support both Terminology Value Sets and Coded Values.

The Abstract Data Type is included to provide future extensibility to support other Data Types than HL7 ISO Data Types. Examples of future usage may be "simple" data types, such as string, boolean, int, etc. Finally the Abstract ISO Data Type represents the "Any" in the HL7 ISO Data type hierarchy.

Figure 14:
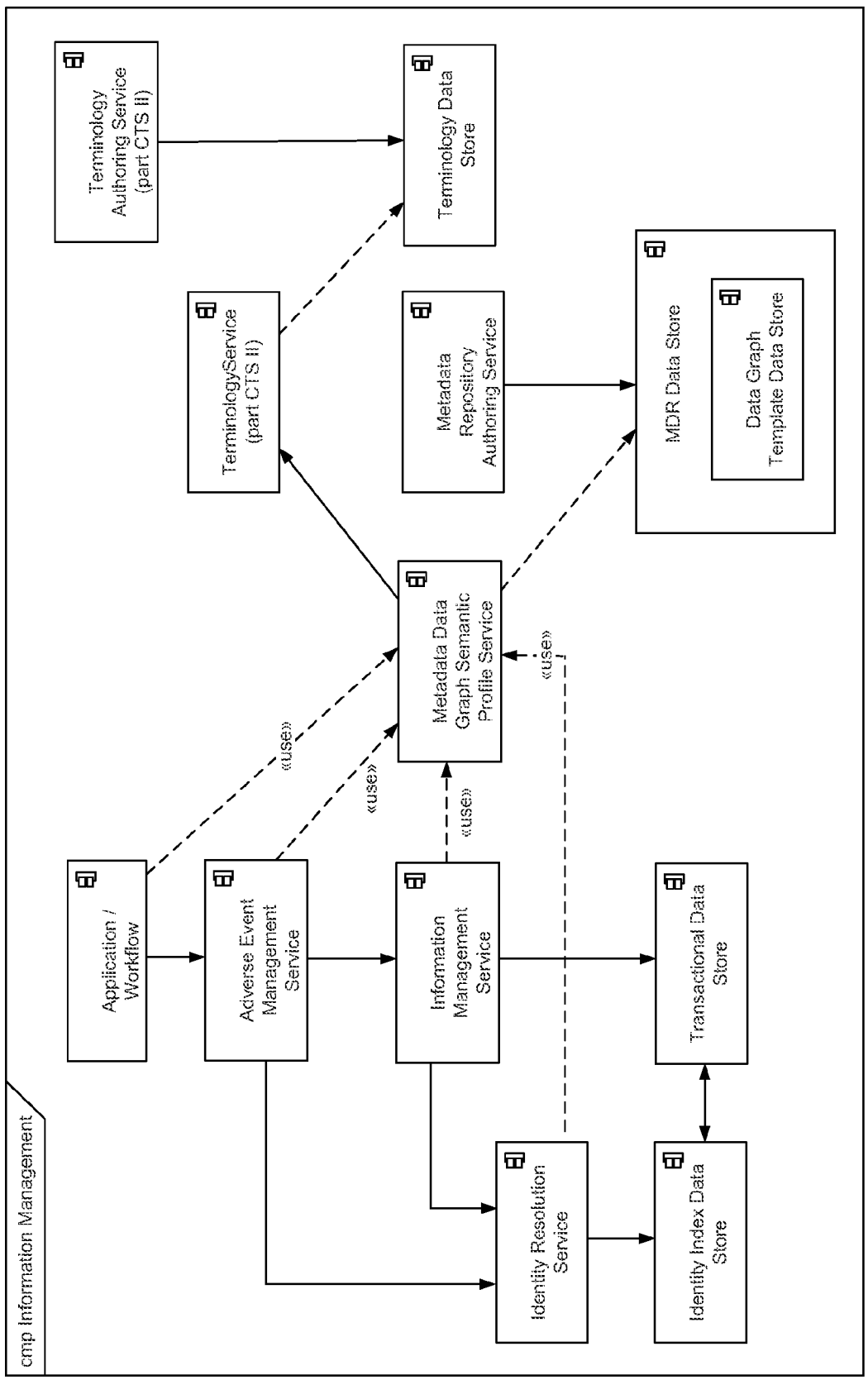
FIG. 14 depicts a services pattern for information management in accordance with an embodiment of the present invention.

Referring to FIG. 14 a services pattern according to an embodiment of the invention is illustrated.

Figure 16:
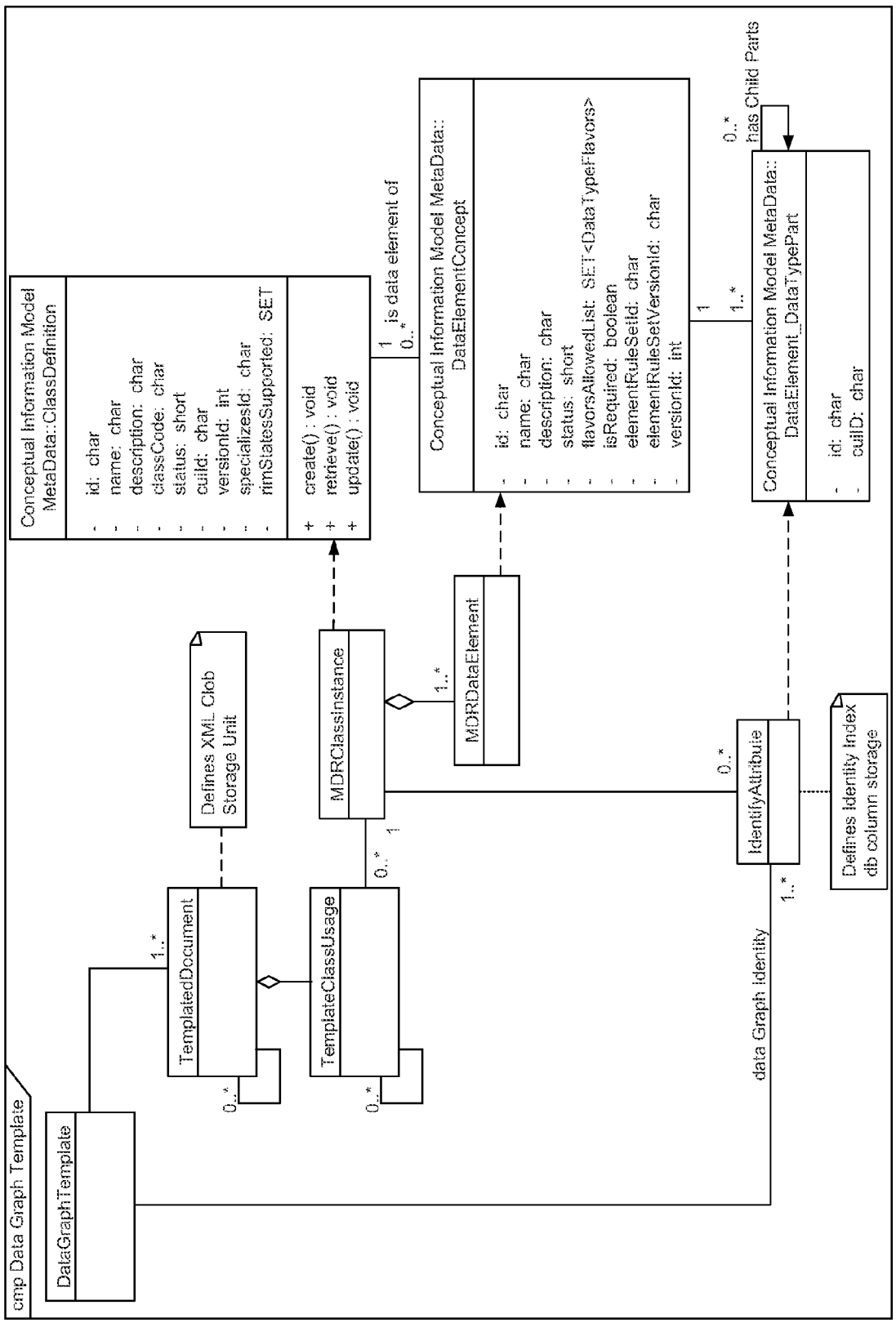
FIG. 16 illustrates a data graph template according to an embodiment of the present invention.

With respect to FIG. 16, a Data Graph Template (Meta Data Graph—MDG) is depicted that provides the controller function within the Mode-View-Controller (MVC) design pattern. For instance, it defines the model sub-set to be used within the Graph, and defines persistence mapping (OR mapping).

In more detail, the Data Graph Template defines a Template Instance Definition and a Usage Context, and controls the instantiation of an Information Management Service (IMS) Data Graph instance. Further, a templated document provides a unit of storage as XML Clob. It has a system level identity (GUID) and contains a defined graph of classes which are bound to Meta Data Repository (MDR) Class Instances. The templated document provides relationship links (link and multiplicity) to other templated documents and provides the ability to define a "Link Document" to other Templated Documents (lazy instantiation).

Moreover, MDG relates to Template Class Usage that defines a class within a Class Data Graph that is used within the Document. The Template Class Usage is bound to the MDR Class Instance (which is bound to the Class Definition in the MDR), and defines an Xpath Id representation. MDG also relates to an MDR Class instance which is a representation of a Class Definition from the MDR, while each MDR Class Definition is only represented once. The MDR Class instance provides container for identifying attributes which are used for identity and query (Identity Index tables).

Figure 17:
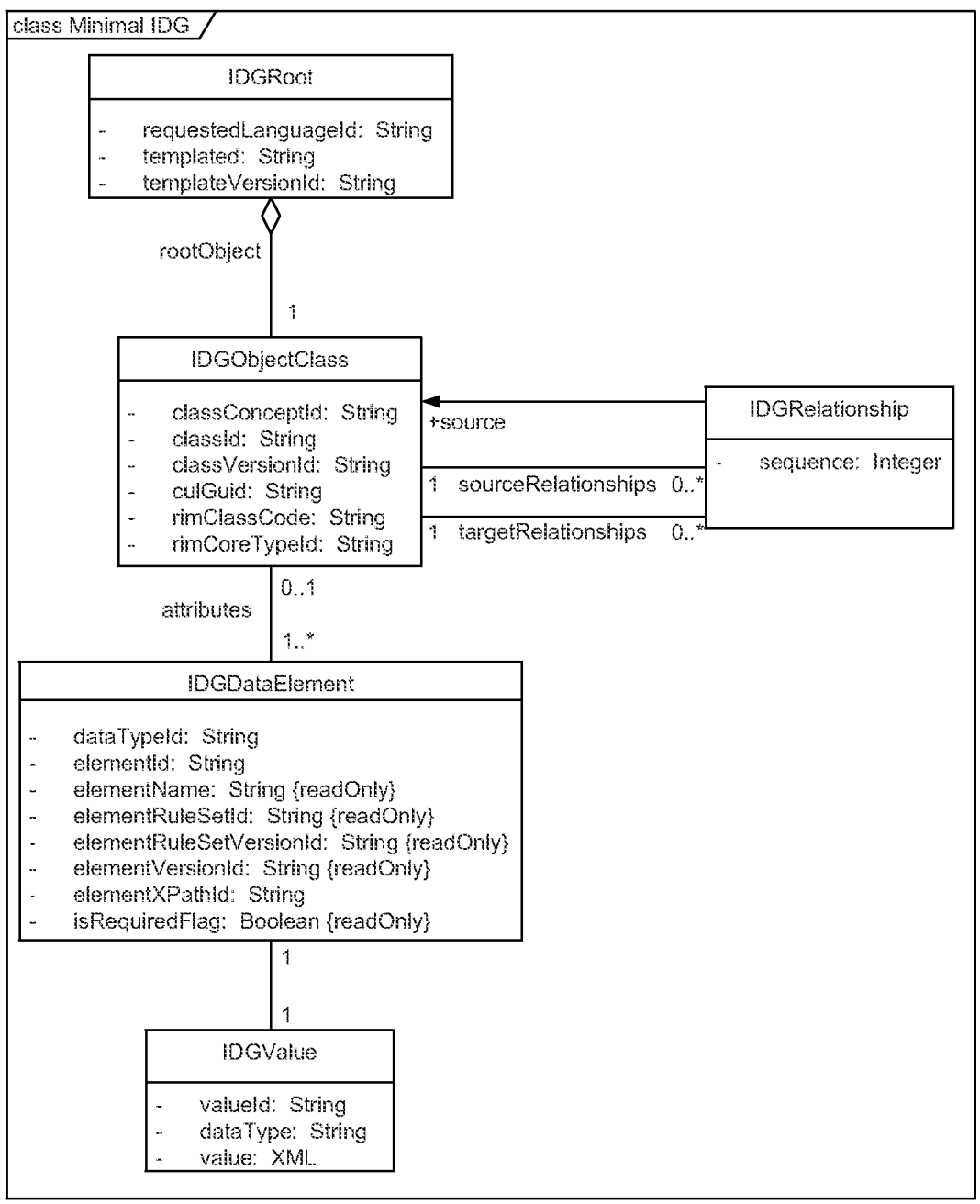
FIG. 17 depicts an information model service data graph in accordance with an embodiment of the present invention.

According to a further embodiment of the present invention, FIG. 17 illustrates a minimum IMS Data Graph (IDG), the View of MVC as depicted in FIG. 13. It is also referred to Data Graph Template which has been explained above in view of FIG. 16. The IMS Data Graph (IDG) is an instance header for a pre-defined acyclic graph of data. It implements a semantic profile. The IDG further includes an Object Class that has a Class Instance and a container for attributes. It is bound to MDR Class Definition via the Data Graph Template and includes a dirty flag for updated information. It can be identified via GUIDs and Xpath ids.

In addition, the IDG includes a Data Element that defines complex data elements (ISO data type). An ISO data type is a representation specific to each data type (may find a generalized pattern) and provides access to the parts of the data type. The IDG is bound to the MDR Data Element Concept via the Data Graph Template. Finally, it is identified via Xpath ids.

The Data Graph Template also relates to Value Domain and Value Set Usage Context Specialization. This provides a runtime value constraint process capability, bound from MDR. Value Set Usage Context provides rules for determining which Value Set to use.

Figure 18:
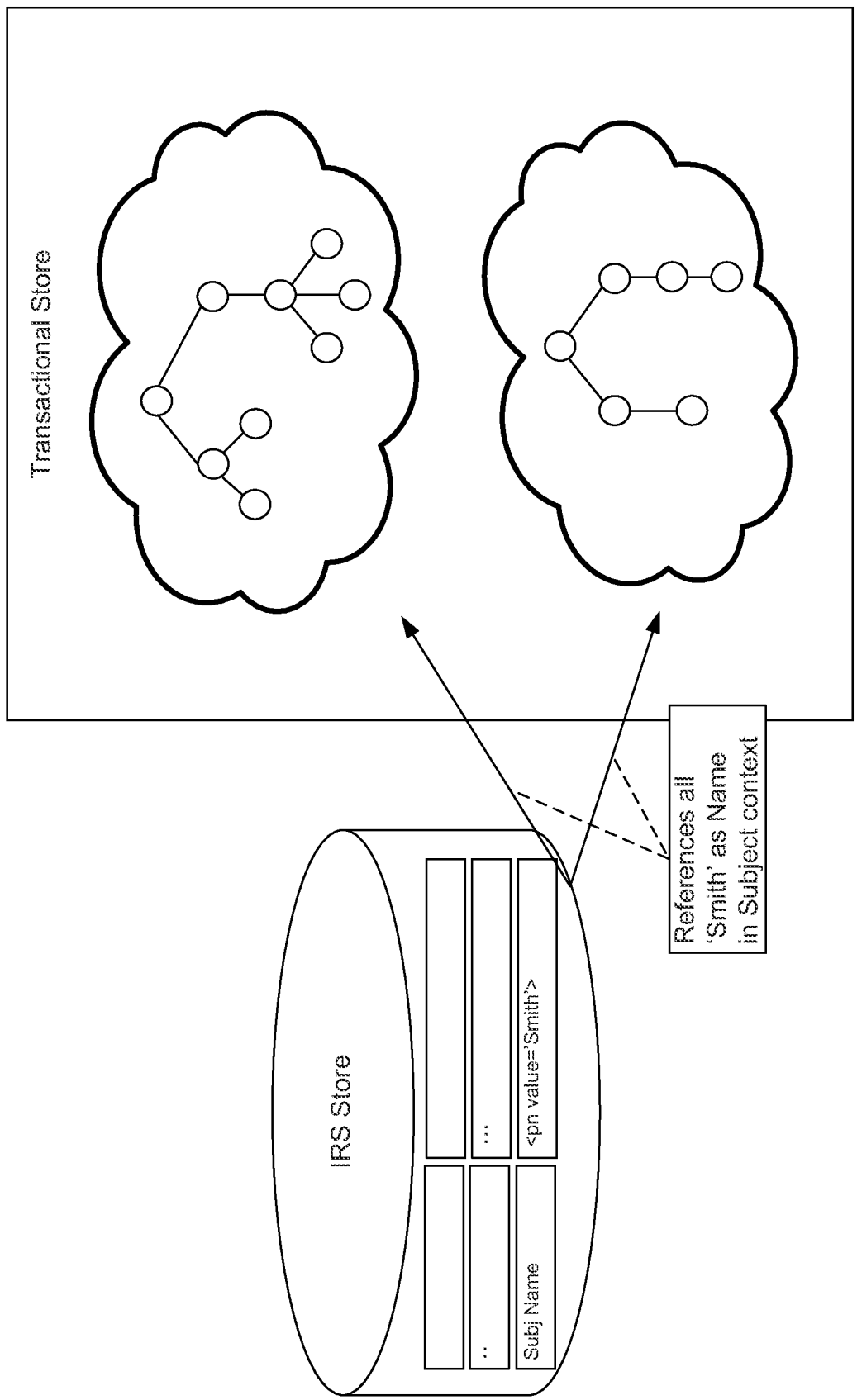
FIG. 18 depicts an example of an IRS indexing in accordance with an embodiment of the present invention.
Figure 19:
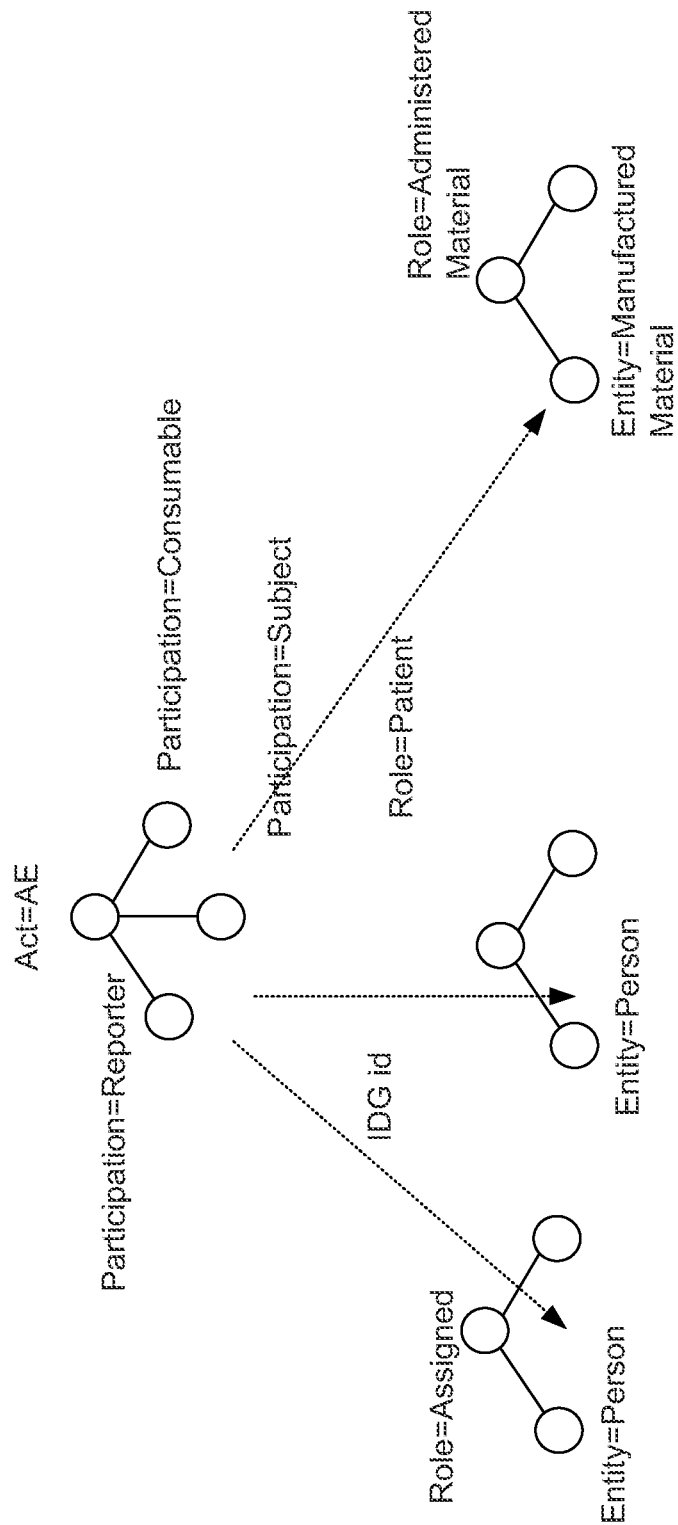
FIG. 19 illustrates an instantiation of a data graph according to an embodiment of the present invention.

Returning to the drawings, FIG. 18 shows the Identity Resolution Service (IRS) indexing details. FIG. 19 illustrates a Data Graph instantiation comprising four steps: 1) Id←Query/create Reporter; 2) Id←Query/create Subject; 3) Id←Query medicinal product; and 4) Create and populate Adverse Event (AE) (Subject Id, Reporter Id, medicinal product Id).

Figure 20:
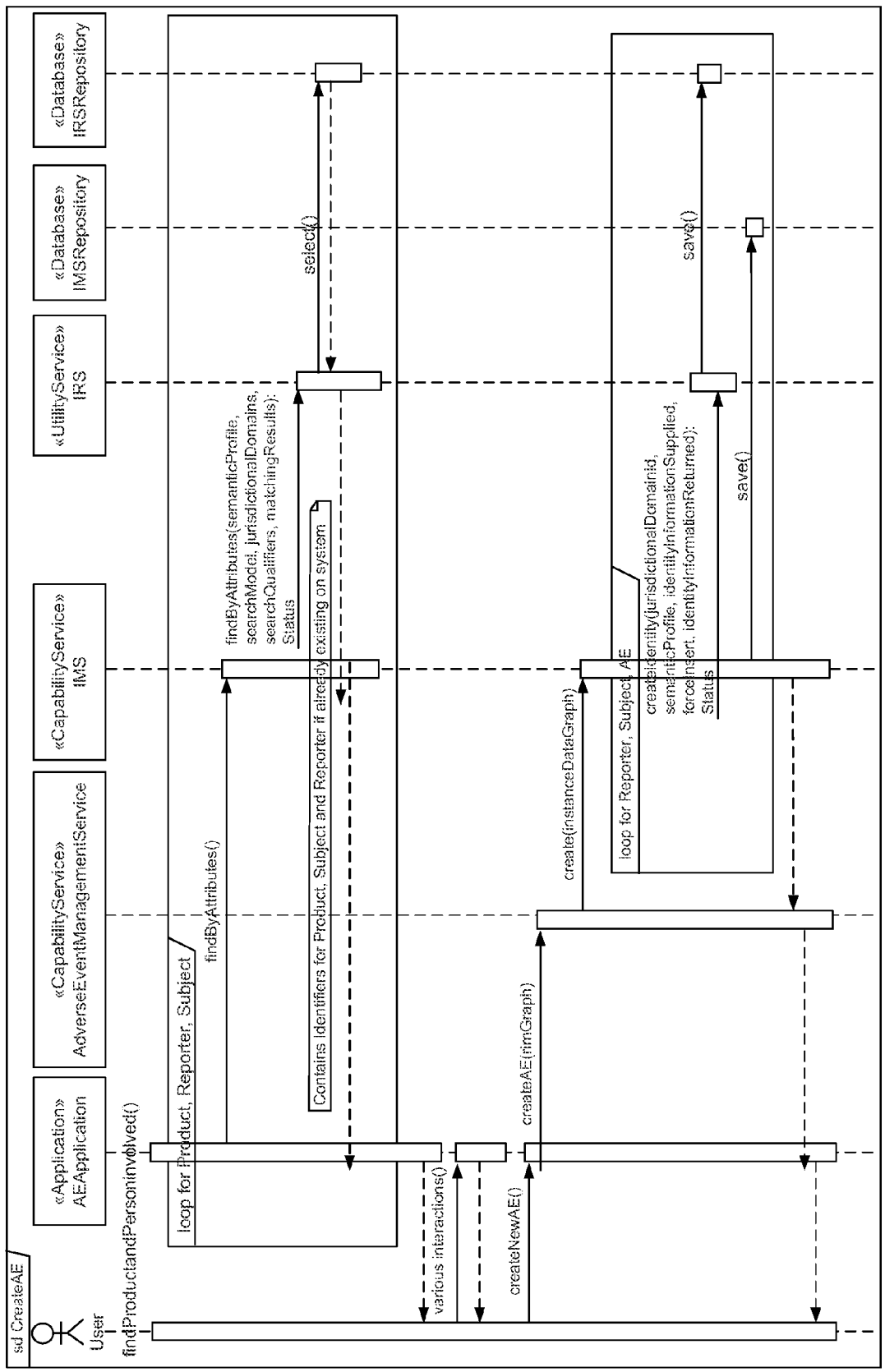
FIG. 20 illustrates a sequencing of the creation of an adverse event object according to an embodiment of the present invention.

FIG. 20 illustrates a typical sequencing for the creation of an AE, according to an embodiment of the present invention. The depicted sequencing may include processes, such as "find product/person involved", or "create a new AE". These processes involve particular components and services instantiated by the system of the present invention. These components and services include an AE-management service or an information management service (IMS). In addition, databases, such as an IMS repository and an IRS repository are employed by the processes.

Figure 21:
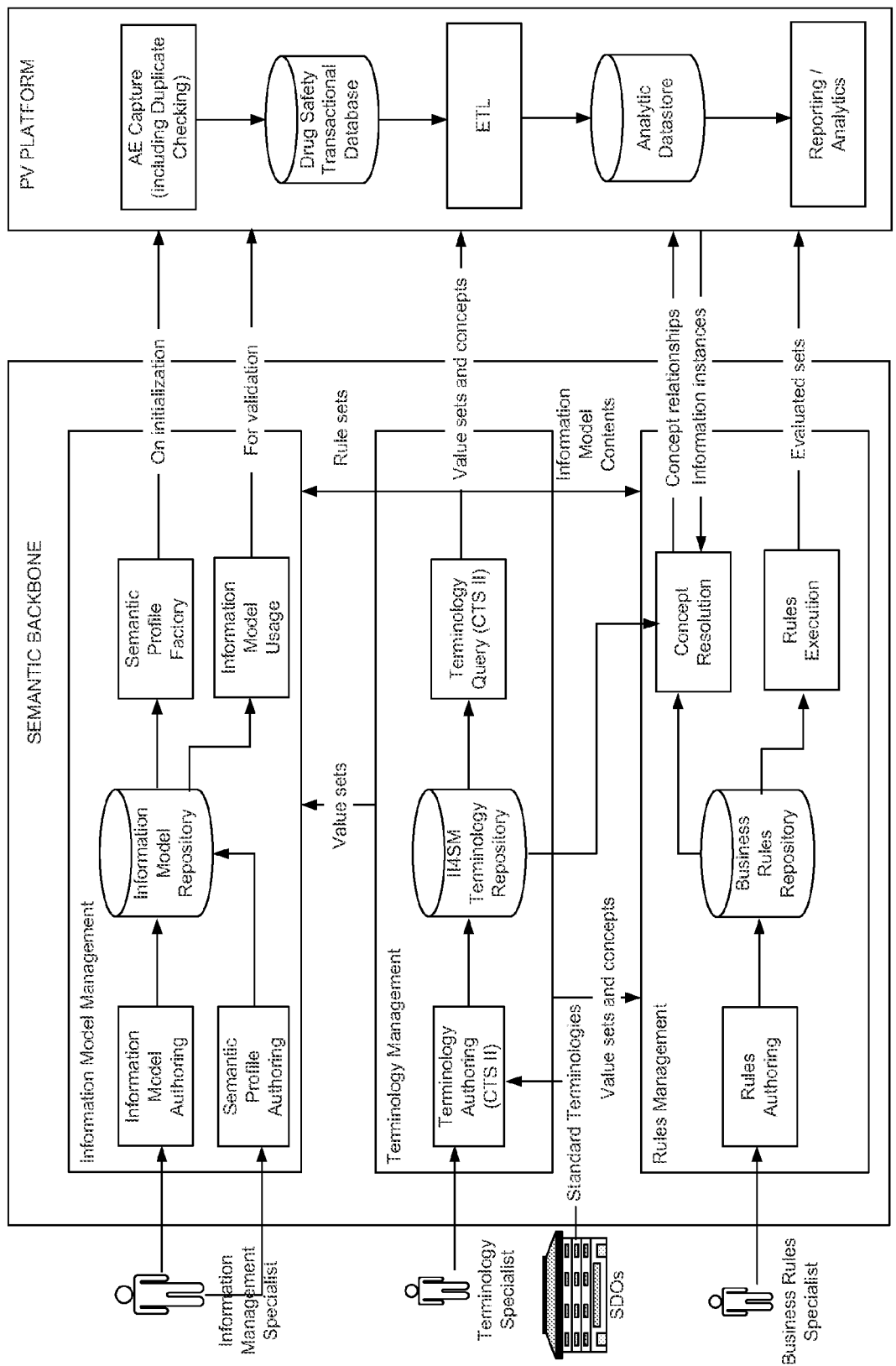
FIG. 21 depicts a further relationship between elements of the semantic backbone of FIG. 1 in accordance with another embodiment of the present invention.

Referring now to FIG. 21, a further embodiment of the present invention employs a semantic backbone as described above with respect to FIG. 4. The depicted embodiment comprises a Pharmacovigilance (PV) Platform communicating with the semantic backbone. This communication may be implemented via the interface depicted in FIG. 4. In a different embodiment, the PV Platform communicates directly with the semantic backbone and therefore provides corresponding services to connect to the services of the semantic backbone. The PV Platform includes an adverse event (AE) capture component, a drug safety transactional database, an Extract Transform and Load (ETL) component, an analytic data store, and a component for reporting and performing analytical functions.

Figure 22:
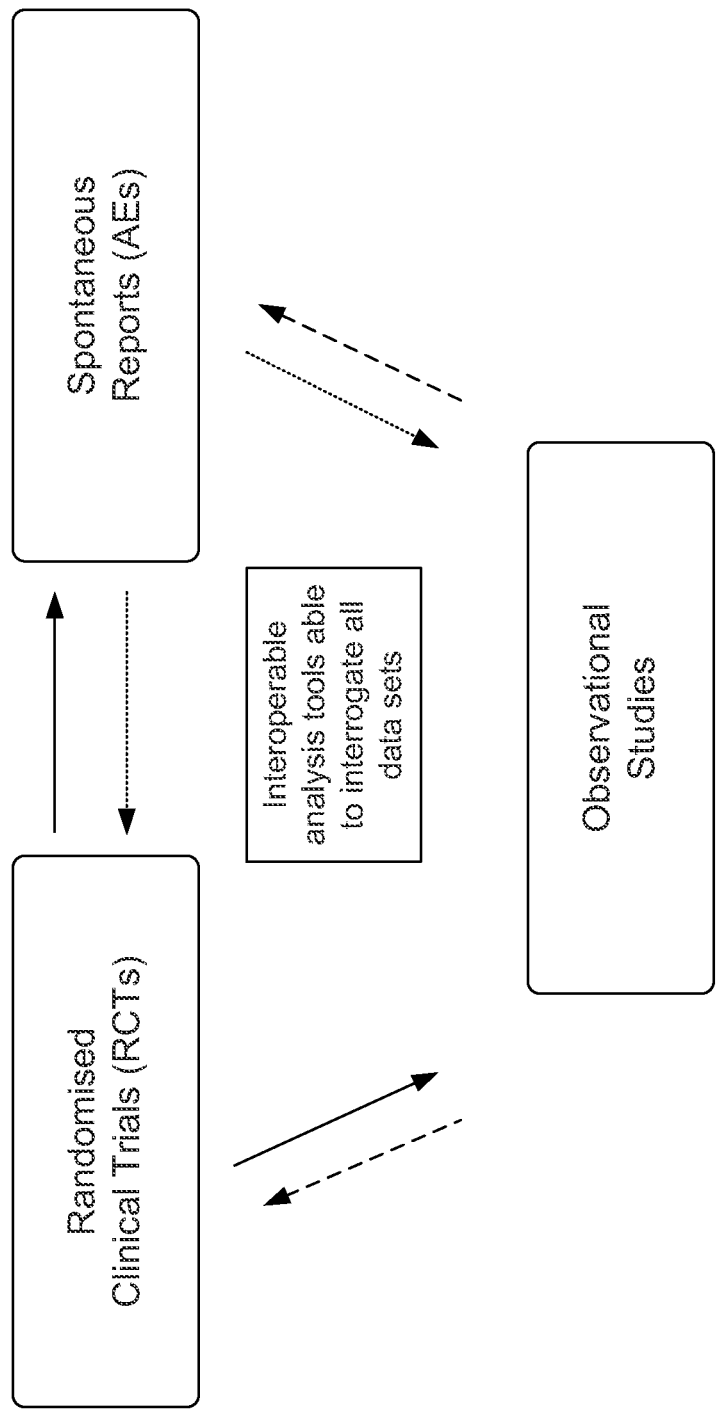
FIG. 22 illustrates the relationship of signal and safety data from different healthcare domains to be collected and evaluated by the semantic backbone of FIG. 4 according to an embodiment of the present invention.

A possible example of such a platform or other tool employing the semantic backbone is illustrated with respect to FIG. 22. For instance, signal and safety data from different healthcare domains as shown in FIG. 22 may be derived during a medicinal trial or other study. This data can be spontaneous data, such as adverse event (AE) data of a clinical trial, which has been generated from a person reporting a side effect. The data is not well structured due to the lack of medicinal knowledge of the person reporting the adverse event. As an example only, most likely the reporting person is unaware of information such as the lot number of the drug or another particular identification code of the producer. The person may not even know the name of the drug she/he has taken. In addition, data can also be derived from a clinical trial. This kind of data is usually well defined and provides a good structure with respect to evaluability. Further, a third source of data may be from observational studies. For instance, a clinic or insurance company collects and evaluates data for which the structure and evaluation goals have been defined before the study. Thus, this data is also well structured and will be in conformity with particular standards.

For example, a public health research may be carried out and the results are stored in compliance with the standard SNOMED. It is to be noted that other standards can be used. Nevertheless, conventionally most observational studies employ SNOMED. Spontaneous data, on the other hand, originates from systems using a MedDRA coding, while clinical trial data often provides its own coding technique. Although some trials are done using SNOMED, there is no uniform manner in which the clinical trial data is collected and/or evaluated.

As will be apparent for the skilled person, the present invention provides an advantageous tool when data of all three types, i.e. spontaneous, clinical trial and observational studies data, has to be queried. For instance, to run a statistical evaluation of specific adverse events with respect to a particular drug, the same evaluation has to be performed within each of the used data management systems. In the above example, the spontaneous data, the clinical trial data and/or the observational studies data needed to be analyzed using the respective conventional systems. The evaluation led to up to three different results which needed to be compared and analyzed themselves. Often, the evaluations have been performed in a manner which is not repeatable, due to missing intermediate results or suitable digital tools.

The present invention on the other hand overcomes this burdensome data handling. In detail, the semantic backbone allows to map between the different data types. For example, all data can be linked via the semantic backbone of the present invention. To evaluate certain statistics, the rules management component can be employed to request the concept of the drug producer. This concept can then be employed by the terminology management component to map between the producer specific concepts and terms and a standardized terminology. Further, since one of the above data is conventionally created using SNOMED and another one using MedDRA, the terminology management component and the information model component will be applied to map between the different standardized terminologies. As already outlined above, the components include a plurality of services, which may be implemented to perform these tasks.

Again with respect to FIG. 4, any system of the "spontaneous data system", the "clinical trial data system", and the "observational data system" can be adapted to be capable of linking to the services of the semantic backbone 100. For example, these systems can use the interface 140 to utilize the services of the backbone. Thus, the existing systems only need a minor modification to link to the semantic backbone. As a consequence, each of the systems will be capable of performing a research, query or other data evaluation over the complete pool of data. Instead of being limited to its own database, the systems have access to all relevant trial, observation or other data regarding a particular drug/medicine.

In another embodiment of the invention, a semantic "wiki" may be introduced to the system. Such a "wiki" may be a dictionary that can be adapted, supplemented and modified by any user of the system. Further, the "wiki" may articulate and represent the meaning of particular items. It also allows discovering concepts in existing standard sources and facilitates computational activities that depend on coded information. Additional advantages of a "wiki" are the reduction of ambiguity as already mentioned above (Pulse rate, pulse oximetry, pulse dose). Thus, a "wiki" will become an essential tool for organizations committed to interoperability and will support enterprise class service oriented architectures.

Further, in accordance with an embodiment of the invention, the above described system and data structures can be used for a clinical data definition process that may be developed using a semantic wiki as introduced above. This clinical data definition process can therefore be enhanced with domain content and additional tooling (for example by Tolven or OntoReason). It also enables enterprise validation. A further capability of the system of the present invention lies in the transformation of definitions into XML representations using constrained templates (Templated Reference Information Models—TRIMs). Since the present invention is available for implementation in any platform, it is completely vendor neutral.

The system of the present invention may run on a server computer, according to an embodiment of the invention. Such a server may be connected to other computer systems (clients) via any available network technology. For instance, the server can be a web-based application server, while the services described above are implemented as web services.

What we claim is:

1. A system for managing and exchanging electronic health record information, the system comprising:
   one or more client computers;
   a computer network; and
   a computable semantics and interoperability server computer communicatively coupled to the one or more client computers over the computer network, wherein the computable semantics and interoperability server computer comprises:
      a terminology management component configured for unified storing of different medical terminologies and for mapping between said different medical terminologies, wherein each medical terminology includes a value set that comprises terms and relationships between terms;
      a rules management component configured for executing conceptual rules, wherein said conceptual rules reflect hierarchies and structures of said different medical terminologies according to a particular standard;
      an information model management component configured for:
         binding to said terminology management component and said rules management component to process electronic health record information from different sources, said information model management component being configured for storing said electronic health record information comprising particular terms of said different medical terminologies, and managing one or more information models created by a model authoring component of an authoring workbench, wherein at least one of the one or more information models includes one or more information model slots; and
      a system configuration management component configured for dynamic binding of said one or more information model slots to one or more value sets via said conceptual rules, wherein each slot includes a pointer to one of said conceptual rules, and wherein said one conceptual rule includes one or more pointers to said one or more value sets;
         wherein each of said rules management component, said terminology management component, and said information model management component employs a plurality of services collaborating with each other as consumers and providers of their respective functionality, and
         wherein said terminology management component is adapted to utilize at least some of said plurality of services to return conceptual information of said different medical terminologies as requested by a service requestor to further process said electronic heath record information.

2. The system of claim 1, wherein said computable semantics and interoperability server computer further comprises:
   a rules repository being included in said rules management component, said rules repository being configured for storing said conceptual rules;
   a terminology repository being included in said terminology management component, said terminology repository being configured for storing mapping value sets; and
   an information model repository being included in said information model management component, said information model repository being configured for storing conceptual information,
      wherein said rules repository, said terminology repository and said information model repository is accessed via a direct bus connection of the computable semantics and interoperability server computer.

3. The system of claim 2, wherein said conceptual information in said information model repository are pointers to medical terminologies stored in said terminology repository.

4. The system of claim 1, said computable semantics and interoperability server computer further comprising a concept resolution service for identifying relationships between concepts and/or between terminologies associated with at least one concept of a medical terminology stored in a terminology repository.

5. The system of claim 4, wherein the concept resolution service is configured for:
   detecting and resolving differences and ambiguities between different representations of a same concept within said medical terminology or across said different medical terminologies, and
   determining if a term or said concept of said medical terminology stored in said terminology repository is in contradiction with the rest of said medical terminology.

6. The system of claim 5, wherein the rules management component provides the concept resolution service.

7. The system of claim 5, wherein the concept resolution service contains a number of algorithmic query mechanisms and ontological-based reasoners to identify and discover implicit relationships between the concepts.

8. The system of claim 5, wherein the concept resolution service contains a number of algorithmic query mechanisms and ontological-based reasoners to identify and discover implicit relationships between concepts, and wherein a reasoning process includes a learning capability to persist implied relationships so that future queries can be resolved with increased efficiency.

9. The system of claim 1, wherein a service to said terminology management component allows to execute said conceptual rules, wherein said conceptual rules define at least one concept of said available different medical terminologies.

10. The system of claim 9, wherein at least said different medical terminologies, such as Systematized Nomenclature of Medicine (SNOMED), Medical Dictionary for Regulatory Activities (MedDRA), International Statistical Classification of Diseases and Related Health Problems (ICD-10) and Anatomical Therapeutic Chemical Classification System (ATC) are preconfigured.

11. The system of claim 1, wherein a service employed by said terminology management component is a medical product management service for creating and maintaining identification information identifying terminologies associated with a medical product.

12. The system of claim 11, wherein said medical product management service further maps between medical product terms and said particular terms of different medical terminologies stored in said information model management component.

13. The system of claim 1, wherein the system is preconfigured to handle common standards for electronic health records such as Clinical Data Interchange Standards Consortium, CDISC, Health Level Seven, HL7, Reference Information Model, RIM, Biomedical Research Integrated Domain Group, BRIDG model, and ISO-21090 data types.

14. The system of claim 1, wherein said information model management component comprises a service configured for loading said electronic health record information to an information model repository.

15. The system of claim 1, wherein said terminology management component comprises a service for querying concepts of terminologies and their attributes stored in a terminology repository.

16. The system of claim 1, wherein said terminology management component registers for events of said rules management component and/or said information model management component, each of said events being triggered by a service of said rules management component and/or by a service of said information model management component.

17. The system of claim 1, wherein said mapping between said different medical terminologies comprises a mapping between a pair of nodes, one from a first ontology and one from a second ontology.

18. The system of claim 17, wherein said mapping is a mapping between said different medical terminologies comprising at least one of SNOMED terminology and MedDRA terminology.

19. The system of claim 1, wherein said computable semantics and interoperability server computer comprises an ontology management component, which comprises the terminology management component.

20. The system of claim 1, wherein said computable semantics and interoperability server computer comprises an ontology management component, which manages at least one ontology and mappings between members of different ontologies, where each of the ontologies include at least one code system and at least one terminology.

21. The system of claim 1, wherein said computable semantics and interoperability server computer further provides the ability to manage and use information in the form of ontologies and comprises a reasoning engine to reason across those ontologies to draw interferences, which uses pre-defined axioms and assertions in those ontologies to establish new facts without the need to define explicit rules.

22. The system of claim 1, wherein said computable semantics and interoperability server computer further comprises an authoring tool for authoring of terminologies and ontologies.

23. The system of claim 22, wherein the authoring tool allows the definition of an ontology and the managing of the content of an ontology, wherein the content is stored in a Tbox and Abox.

24. The system of claim 1, wherein the authoring workbench provides an integrated tooling environment for definition and management of information models, rules, processes, rule-based terminology binding, and system configuration data.

25. The system of claim 1, wherein a particular value set or sub-set of a terminology and/or ontology can be bound to the information model slot.

* * * * *